(12) United States Patent
Karla et al.

(10) Patent No.: US 10,413,199 B2
(45) Date of Patent: Sep. 17, 2019

(54) CONNECTORS FOR MEDICAL EQUIPMENT

(71) Applicant: Welch Allyn, Inc., Skaneateles Falls, NY (US)

(72) Inventors: Sean R. Karla, Syracuse, NY (US); Raymond A. Lia, Auburn, NY (US); Scott A. Martin, Camillus, NY (US); Robert L. Vivenzio, Auburn, NY (US); Thaddeus J. Wawro, Auburn, NY (US); Chris R. Roberts, Skaneateles, NY (US); Jeffrey J. Perkins, Tully, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 0 days.

(21) Appl. No.: 16/228,113

(22) Filed: Dec. 20, 2018

(65) Prior Publication Data

US 2019/0125200 A1 May 2, 2019

Related U.S. Application Data

(63) Continuation of application No. 16/179,304, filed on Nov. 2, 2018.
(Continued)

(51) Int. Cl.
*A61B 5/021* (2006.01)
*A61B 5/022* (2006.01)

(52) U.S. Cl.
CPC .......... *A61B 5/02141* (2013.01); *A61B 5/022* (2013.01); *A61B 2560/0406* (2013.01); *A61B 2560/0443* (2013.01); *F16L 2201/44* (2013.01)

(58) Field of Classification Search
CPC ................ A61B 5/02141; A61B 5/022; A61B 2560/0443; A61B 2560/0406; F16L 2201/44
(Continued)

(56) References Cited

U.S. PATENT DOCUMENTS

| 1,106,341 A | 8/1914 | Bristol |
| 1,328,876 A | 1/1920 | Hill |

(Continued)

FOREIGN PATENT DOCUMENTS

| CA | 2100854 | 1/1994 |
| CN | 203736183 | 7/2014 |

(Continued)

OTHER PUBLICATIONS

Canadian Office Action dated Jan. 30, 2015 for Canadian patent application No. 2622633, 3 pages.
(Continued)

*Primary Examiner* — Zachary T Dragicevich
(74) *Attorney, Agent, or Firm* — Lee & Hayes, P.C.

(57) ABSTRACT

An adapter includes a substantially rigid body having a distal portion, a proximal portion, a central opening formed at least in part by an inner wall of the body, and a longitudinal axis extending substantially centrally through the opening. The distal portion includes an annular ring having a top surface and a ridge disposed opposite the top surface, the ridge extending substantially perpendicular to the longitudinal axis. The distal. The adapter also includes a seal configured to form a substantially fluid-tight seal with a surface of a fitting removably attachable to the adapter.

30 Claims, 26 Drawing Sheets

Related U.S. Application Data

(60) Provisional application No. 62/580,679, filed on Nov. 2, 2017.

(58) Field of Classification Search
USPC .................................. 600/490; 285/201, 305
See application file for complete search history.

(56) References Cited

U.S. PATENT DOCUMENTS

| | | |
|---|---|---|
| 1,377,032 A | 5/1921 | Starling et al. |
| 2,087,494 A | 7/1937 | Annin |
| 2,199,408 A | 5/1940 | Liberte |
| 2,341,137 A | 2/1944 | Damron |
| 2,564,669 A | 8/1951 | Brady |
| 2,636,394 A | 4/1953 | Melchior |
| 2,678,040 A | 5/1954 | Poole et al. |
| 2,714,379 A | 8/1955 | Raines |
| 3,279,459 A | 10/1966 | Schenker |
| 3,603,304 A | 9/1971 | Maier |
| 3,606,880 A | 9/1971 | Ogle, Jr. |
| 3,633,567 A | 1/1972 | Samoff |
| 3,635,214 A | 1/1972 | Rand et al. |
| 3,659,592 A | 5/1972 | Natkanski |
| 3,756,239 A | 9/1973 | Smythe |
| 3,757,772 A | 9/1973 | Goldblat et al. |
| 3,760,795 A | 9/1973 | Adelhed |
| 3,773,036 A | 11/1973 | Weyer |
| 3,797,315 A | 3/1974 | Halpern |
| 3,805,618 A | 4/1974 | Csaposs et al. |
| 3,874,242 A | 4/1975 | Csaposs et al. |
| 3,906,937 A | 9/1975 | Aronson |
| D244,879 S | 6/1977 | Manno |
| 4,036,061 A | 7/1977 | Speidel |
| 4,036,216 A | 7/1977 | Ramsey, III |
| 4,040,298 A | 8/1977 | Lee et al. |
| 4,198,031 A | 4/1980 | Ezekiel et al. |
| 4,248,241 A | 2/1981 | Tacchi |
| 4,255,970 A | 3/1981 | Van Pottelberg |
| D269,905 S | 7/1983 | Tamm |
| 4,501,271 A | 2/1985 | Clifton et al. |
| 4,535,938 A | 8/1985 | Lindabury, Sr. |
| 4,543,824 A | 10/1985 | Marterer |
| 4,549,550 A | 10/1985 | Kami |
| 4,605,010 A | 8/1986 | McEwen |
| 4,653,506 A | 3/1987 | Romanovskaya |
| 4,685,336 A | 8/1987 | Lee |
| 4,726,382 A | 2/1988 | Boehmer et al. |
| 4,726,686 A | 2/1988 | Wolf et al. |
| 4,802,370 A | 2/1989 | Eernisse et al. |
| 4,844,512 A | 7/1989 | Gahwiler |
| 4,896,676 A | 1/1990 | Sasaki |
| 4,920,971 A | 5/1990 | Blessinger |
| 4,967,758 A | 11/1990 | Masciarotte |
| 4,979,953 A | 12/1990 | Spence |
| 5,003,981 A | 4/1991 | Kankkunen et al. |
| 5,025,792 A | 6/1991 | Hon et al. |
| 5,047,021 A | 9/1991 | Utterberg |
| 5,048,533 A | 9/1991 | Muz |
| 5,101,830 A | 4/1992 | Duffy et al. |
| 5,137,024 A | 8/1992 | Souma |
| 5,179,957 A | 1/1993 | Williams |
| 5,181,422 A | 1/1993 | Leonard et al. |
| 5,220,925 A | 6/1993 | Hishida |
| 5,228,448 A | 7/1993 | Byrd |
| 5,275,444 A | 1/1994 | Wythoff |
| 5,320,169 A | 6/1994 | Delatorre |
| 5,392,782 A | 2/1995 | Garrett |
| D356,155 S | 3/1995 | Caven |
| 5,396,894 A | 3/1995 | Eide et al. |
| 5,400,787 A | 3/1995 | Marandos |
| 5,411,518 A | 5/1995 | Goldstein et al. |
| 5,413,582 A | 5/1995 | Eaton |
| 5,424,598 A | 6/1995 | Corbett |
| 5,511,552 A | 4/1996 | Johnson |
| 5,513,534 A | 5/1996 | Brechbuhl et al. |
| 5,513,643 A | 5/1996 | Suite |
| 5,626,142 A | 5/1997 | Marks |
| 5,649,954 A | 7/1997 | McEwen |
| 5,660,182 A | 8/1997 | Kuroshaki et al. |
| 5,678,558 A | 10/1997 | Johnson |
| 5,690,672 A | 11/1997 | Cohen |
| 5,746,213 A | 5/1998 | Marks |
| 5,753,821 A | 5/1998 | Chou |
| 5,819,739 A | 10/1998 | Levavi et al. |
| 5,882,515 A | 3/1999 | Lacy et al. |
| 5,904,655 A | 5/1999 | Brackett |
| 5,937,885 A | 8/1999 | Sampson |
| 5,966,829 A | 10/1999 | Lia et al. |
| 6,036,718 A | 3/2000 | Ledford et al. |
| 6,082,170 A | 7/2000 | Lia et al. |
| 6,095,983 A | 8/2000 | Wawro |
| 6,120,458 A | 9/2000 | Lia et al. |
| 6,152,880 A | 11/2000 | Okada |
| 6,168,566 B1 | 1/2001 | Lia et al. |
| 6,189,558 B1 | 2/2001 | Traylor |
| 6,213,953 B1 | 4/2001 | Reeves |
| 6,234,972 B1 | 5/2001 | Lia et al. |
| 6,245,023 B1 | 6/2001 | Clemmons |
| 6,245,024 B1 | 6/2001 | Montagnino et al. |
| 6,334,025 B1 | 12/2001 | Yamagami |
| 6,346,084 B1 | 2/2002 | Schnell et al. |
| 6,394,977 B1 | 5/2002 | Taylor et al. |
| 6,422,086 B1 | 7/2002 | Dromms et al. |
| 6,475,153 B1 | 11/2002 | Khair et al. |
| 6,481,291 B1 | 11/2002 | Lia et al. |
| 6,506,162 B1 | 1/2003 | Tseng |
| 6,525,238 B2 | 2/2003 | Corrales |
| 6,551,249 B2 | 4/2003 | Ashida et al. |
| 6,578,428 B1 | 6/2003 | Dromms et al. |
| 6,615,666 B1 | 9/2003 | Lia et al. |
| 6,616,666 B1 | 9/2003 | Michelson |
| 6,682,547 B2 | 1/2004 | McEwen et al. |
| 6,746,406 B2 | 6/2004 | Lia et al. |
| 6,796,186 B2 | 9/2004 | Lia et al. |
| D532,519 S | 11/2006 | Aujla et al. |
| 7,722,542 B2 | 5/2010 | Lia et al. |
| 2001/0005777 A1 | 6/2001 | Nakagawa et al. |
| 2002/0099297 A1 | 7/2002 | Nakagawa et al. |
| 2002/0156382 A1 | 10/2002 | Freund et al. |
| 2003/0036690 A1 | 2/2003 | Geddes et al. |
| 2004/0083816 A1 | 5/2004 | Lia et al. |
| 2004/0092831 A1 | 5/2004 | Hood, Jr. |
| 2004/0181156 A1 | 9/2004 | Kingsford et al. |
| 2006/0089668 A1 | 4/2006 | Warburton |
| 2006/0217618 A1 | 9/2006 | Lia et al. |
| 2007/0135836 A1 | 6/2007 | McEwen et al. |
| 2007/0244506 A1 | 10/2007 | McEwen et al. |
| 2008/0058720 A1* | 3/2008 | Spohn ................ A61B 5/02141 |
| 2009/0124911 A1* | 5/2009 | Lin ........................ A61B 5/022 |
| | | 600/490 |
| 2012/0010455 A1 | 1/2012 | Reichenbach et al. |
| 2012/0042971 A1* | 2/2012 | Py |
| 2013/0331716 A1 | 12/2013 | Wawro et al. |
| 2016/0183816 A1 | 6/2016 | Wawro et al. |
| 2016/0367156 A1 | 12/2016 | Wawro et al. |
| 2017/0284582 A1 | 10/2017 | Lombardi et al. |

FOREIGN PATENT DOCUMENTS

| | | |
|---|---|---|
| DE | 591564 | 1/1934 |
| EP | 0591564 | 10/1992 |
| EP | 0705563 | 4/1996 |
| EP | 1945096 | 7/2008 |
| EP | 1992281 | 11/2008 |
| FR | 2592297 | 7/1987 |
| GB | 740181 | 11/1955 |
| KR | 1020080084863 | 9/2008 |
| WO | WO 0022983 | 4/2000 |
| WO | WO 0040941 | 7/2000 |
| WO | WO 02/26128 | 4/2002 |
| WO | WO2007/035271 | 3/2007 |

(56) References Cited

FOREIGN PATENT DOCUMENTS

OTHER PUBLICATIONS

European Office Action dated Jan. 2, 2017 for European Patent Application No. 06790195.9, a counterpart foreign application of the U.S. Pat. No. 8,535,233, 5 pages.
European Office Action dated Jan. 2, 2017 for European patent application No. 12158917.0, a counterpart foreign application of U.S. Pat. No. 8,535,233, 5 pages.
European Office Action dated Oct. 5, 2015 for European Patent Application No. 06790195.9, a counterpart foreign application of the U.S. Pat. No. 8,535,233, 5 pages.
European Office Action dated Nov. 27, 2017 for European patent application No. 12158917.0, a counterpart foreign application of U.S. Pat. No. 8,535,233, 6 pages.
Extended European Search Report dated Jul. 17, 2015 for European Patent Application No. 12158917.0, 7 pages.
European Search Report for for EP Application No. 067901959, dated Oct. 30, 2009, 11 pages.
International Search Report and Written Opinion from PCT/US2006/34909 dated Feb. 5, 2007, 8 pages.
International Search Report Corresponding to PCT/US2007/016828, dated Jan. 18, 2008, 9 pages.
Office Action for U.S. Appl. No. 15/188,439, dated Jan. 24, 2019, Wawro, "Blood Pressure Measuring Apparatus", 7 pages.
Office Action for U.S. Appl. No. 14/790,873, dated Oct. 2, 2017, Wawro, "Blood Pressure Measuring Apparatus", 11 pages.
Office Action for U.S. Appl. No. 14/790,873, dated May 9, 2018, Wawro, "Blood Pressure Measuring Apparatus", 16 pages.
Operating Instruction Manual, Welch Allyn Drua Shock Integrated Aneroid Sphygmomanometer, pp. 1-7, 2001.
"Plastics Plus, Inc. Biodegradable Solution PPI BD-0701", published Oct. 2008, 8 pages.
"Socket", The American Heritage Dictionary of the English Language, Houghton Mifflin Company 2003, retrieved Nov. 7, 2007 from <<http://wwwcredoreference.com/entry/4133272, 1 page.
PCT Search Report and Written Opinion dated Mar. 6, 2019, for PCT Application No. PCT/US2018/058988, 11 pages.

\* cited by examiner

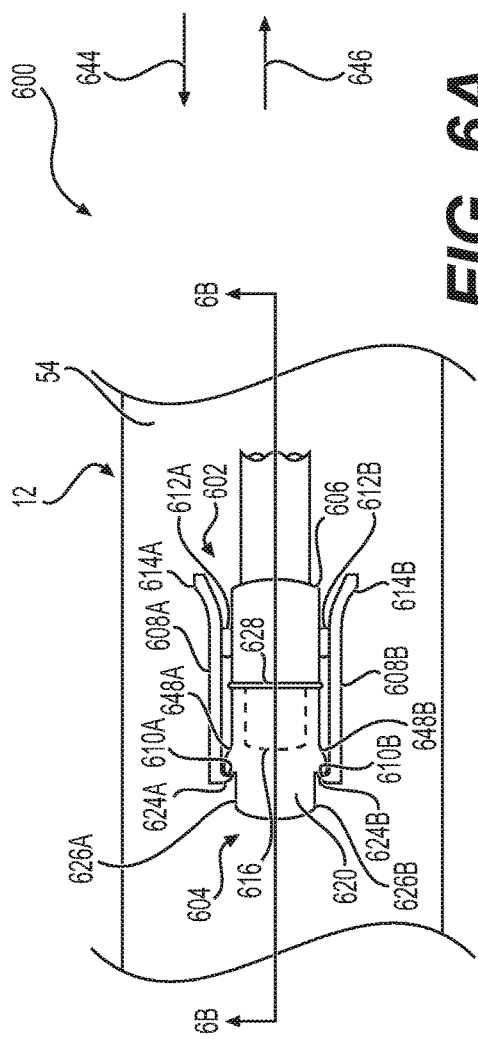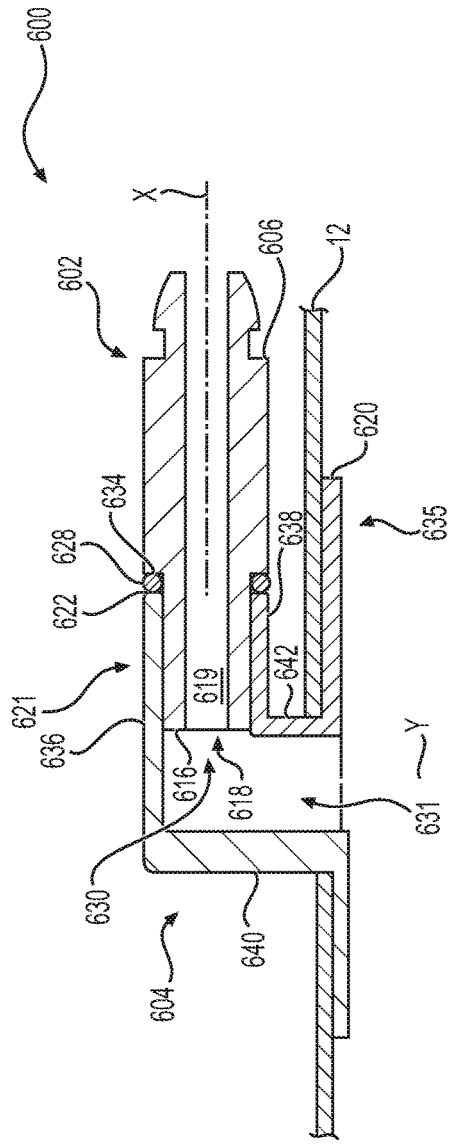

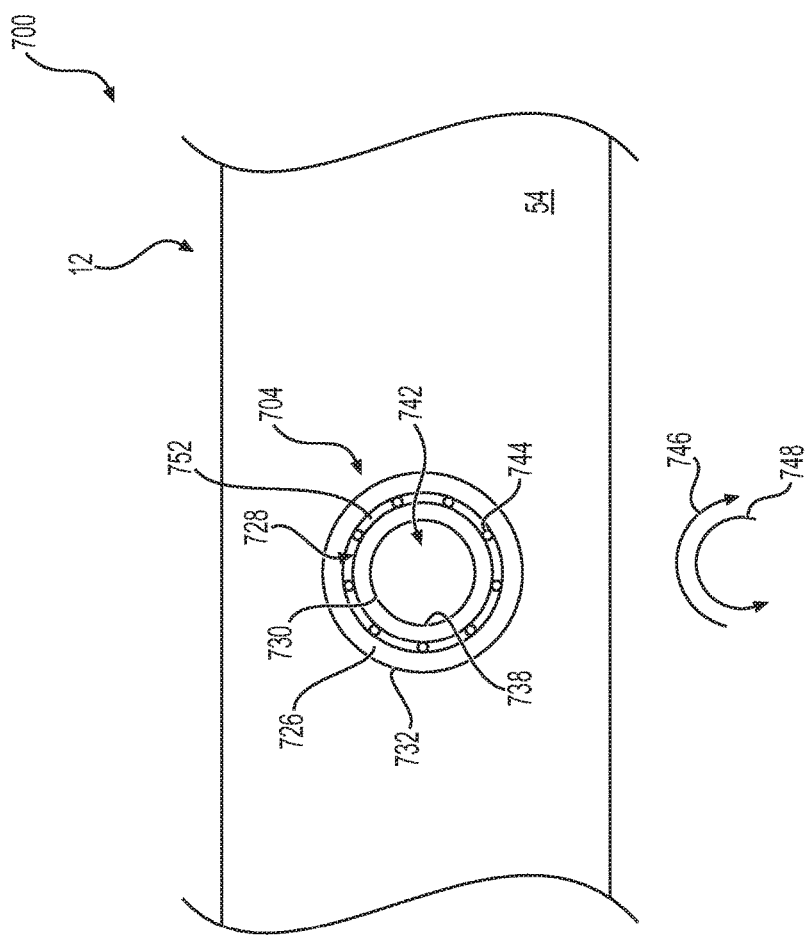

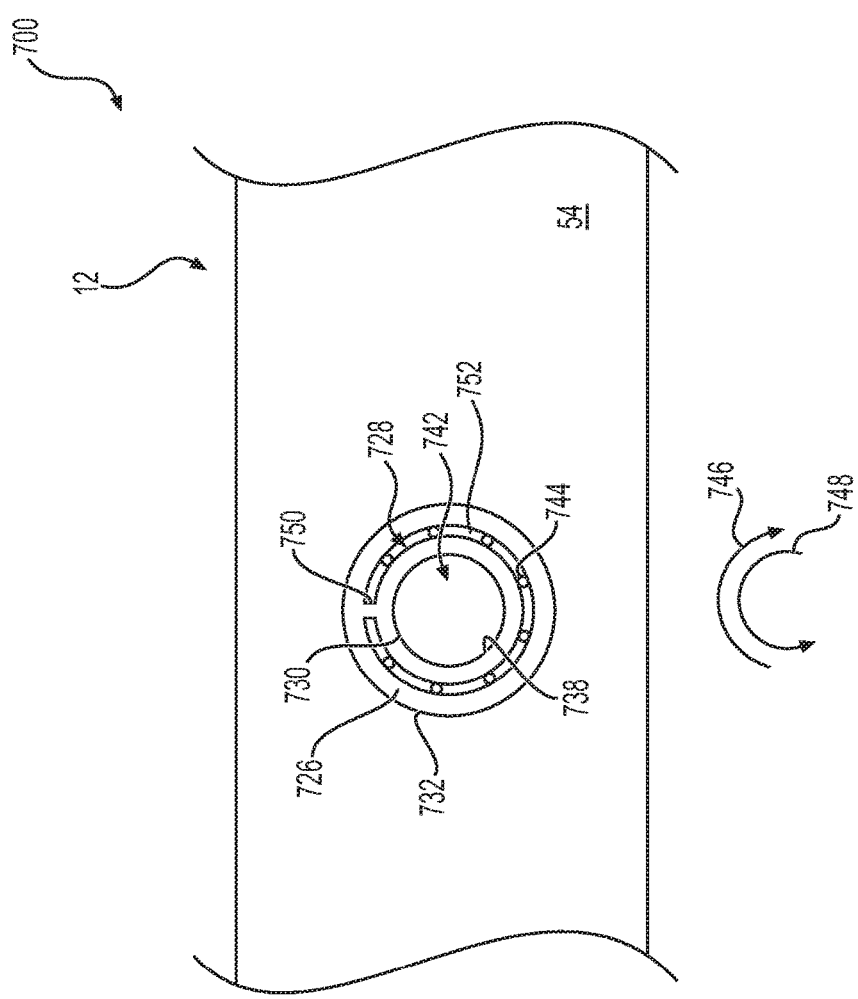

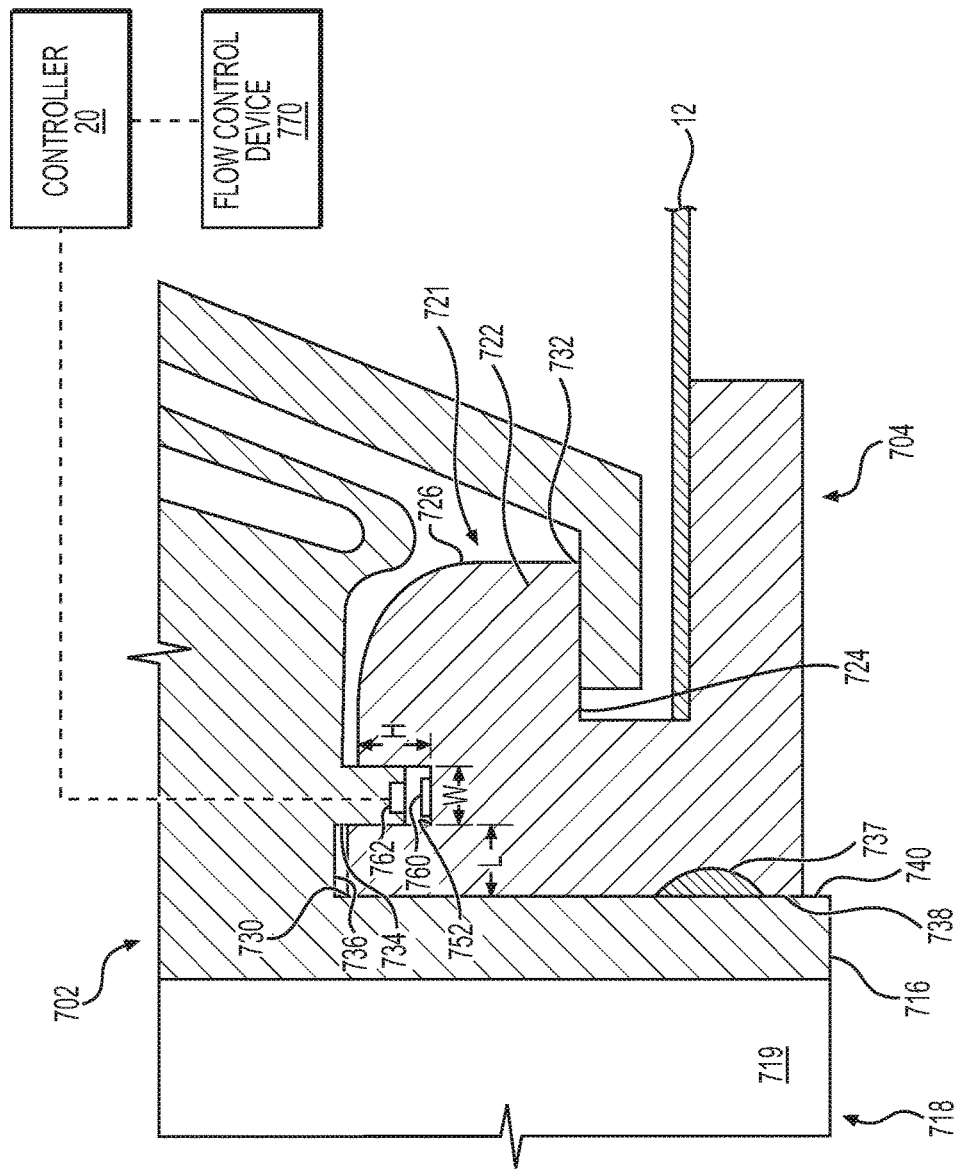

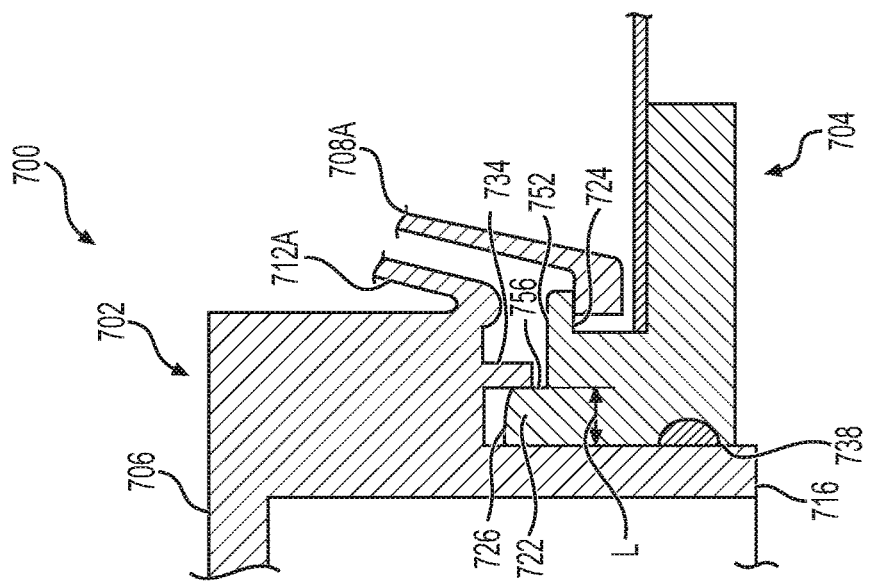
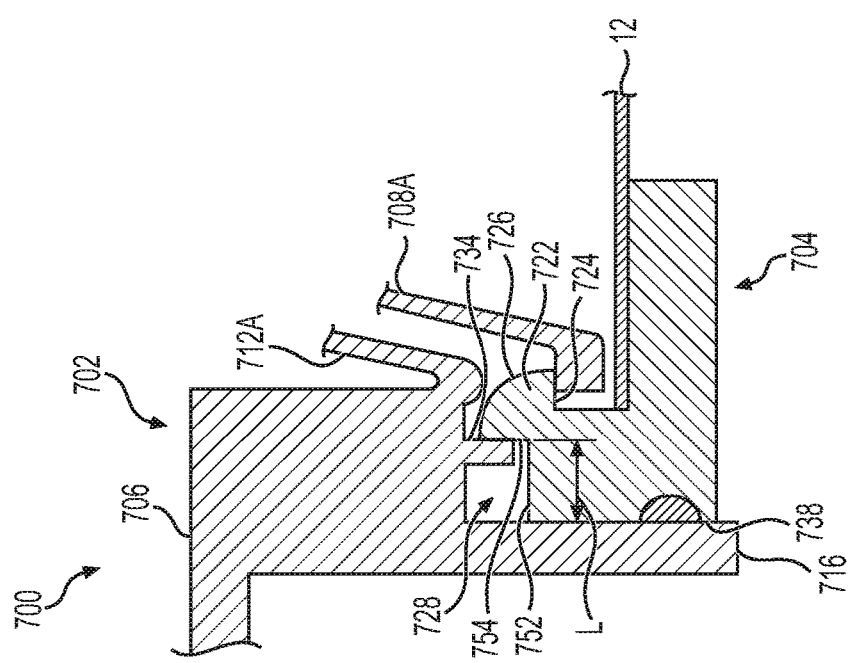

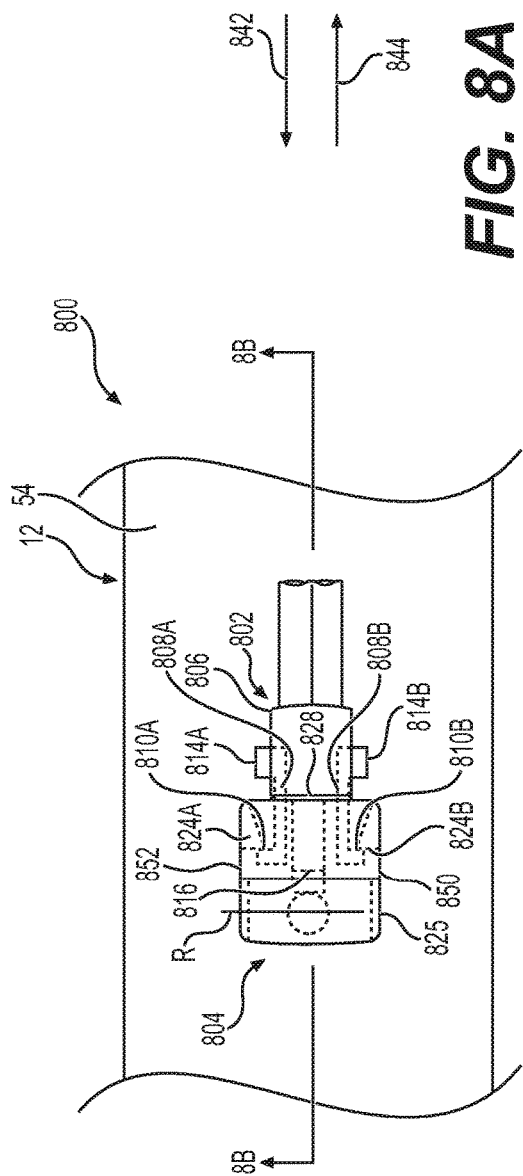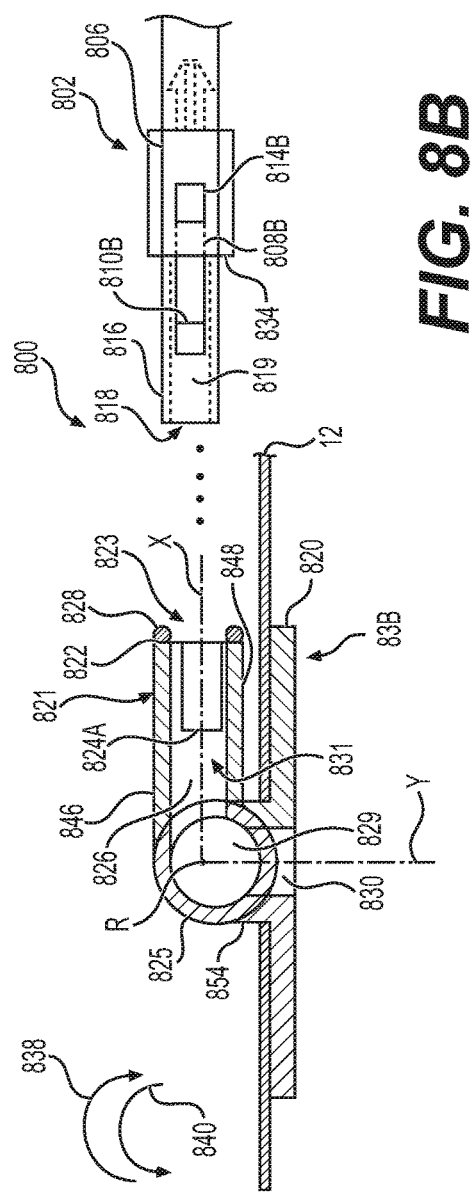

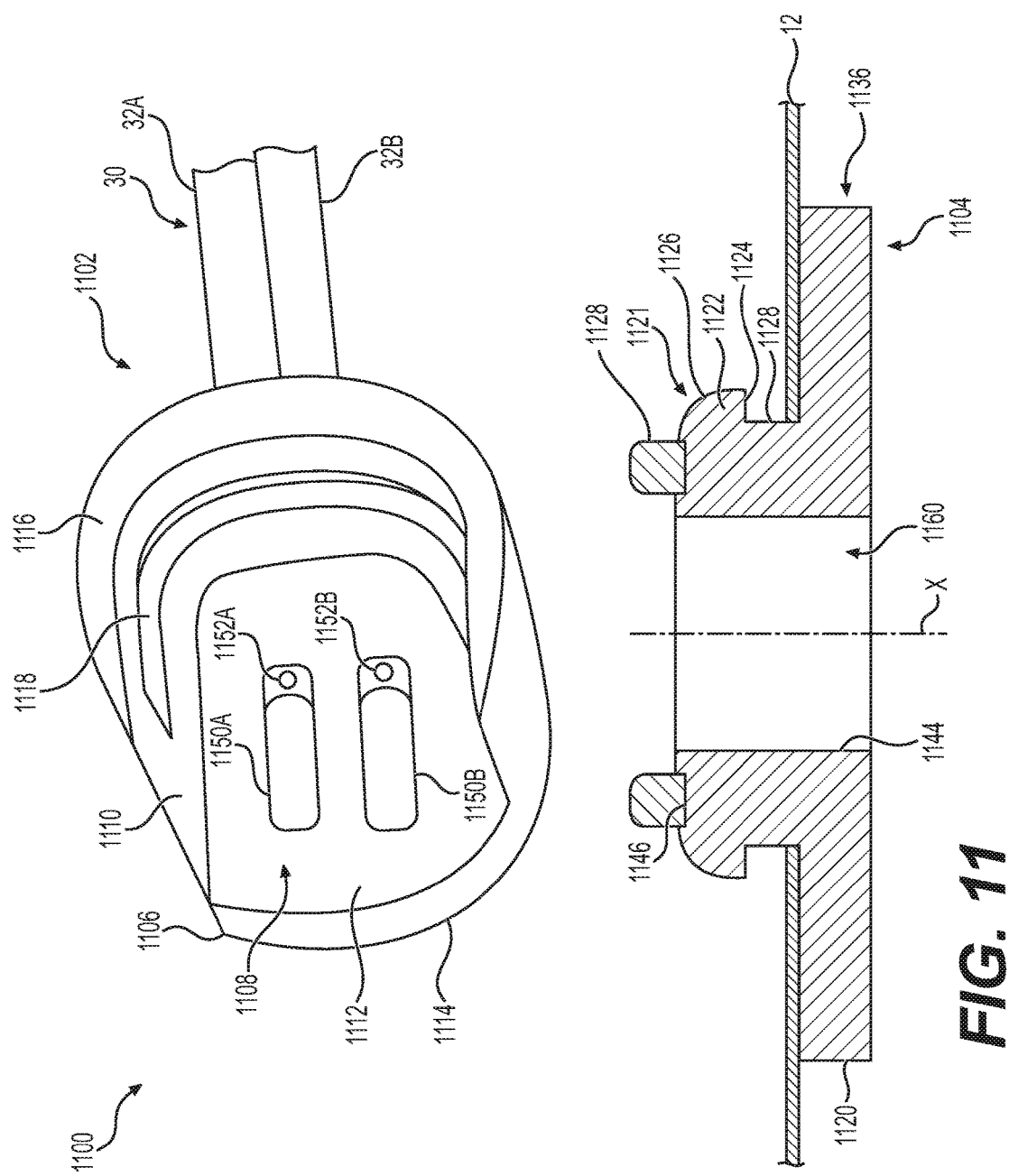

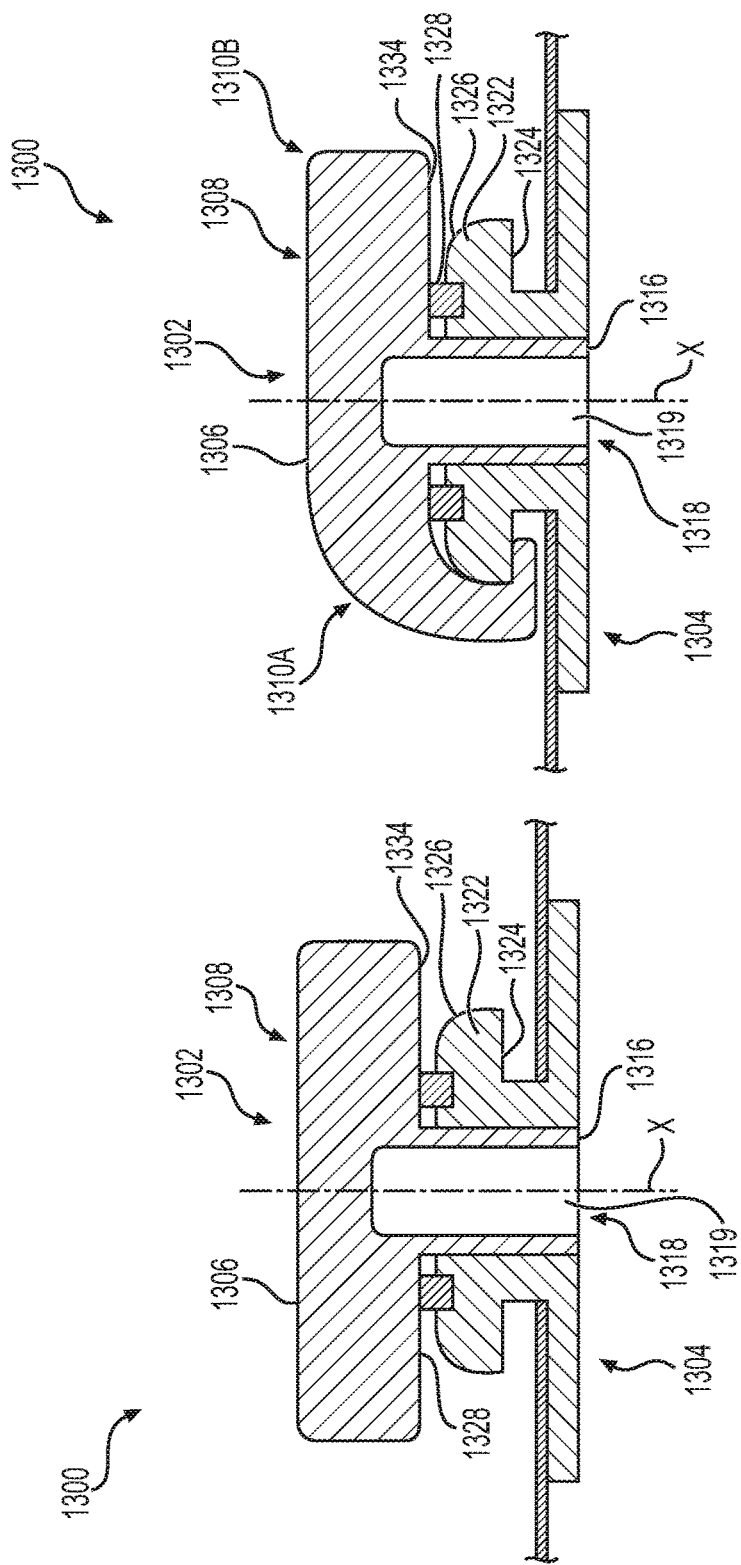

CONNECTORS FOR MEDICAL EQUIPMENT

CROSS-REFERENCE TO RELATED APPLICATIONS

The present application is a continuation of U.S. application Ser. No. 16/179,304, filed Nov. 2, 2018, which is a nonprovisional application of U.S. Provisional Application No. 62/580,679, filed Nov. 2, 2017, the entire disclosures of which are incorporated herein by reference.

TECHNICAL FIELD

This application is directed to medical equipment, and in particular, to connectors for use with medical equipment configured to determine hemodynamic parameters associated with a patient.

BACKGROUND

Some non-invasive patient monitoring devices are configured to inflate a cuff to a pressure above a patient's systolic blood pressure in order to occlude arterial blood flow in the limb on which the cuff is disposed. Once above systole, the cuff can be deflated, and the systolic and diastolic pressures of the patient can be calculated based on measurements made during cuff deflation.

In situations in which the patient's blood pressure and/or other hemodynamic parameters may be monitored over extended periods, it may be desirable to leave the cuff disposed about the patient's limb even when the cuff is not being used to obtain measurements. In such examples, it is common for the patient to be transferred between several different locations of the healthcare facility to receive care, and different cuff inflation devices or other patient monitoring system components may be connected to the cuff at each of the different locations in order to obtain hemodynamic parameter measurements at such locations. Accordingly, there is a need for reliable and universally compatible means for temporarily fluidly connecting the cuff with different patient monitoring systems disposed at various locations throughout the healthcare facility.

The various example embodiments of the present disclosure are directed toward overcoming one or more of the deficiencies associated with known cuff connection devices.

SUMMARY

In an example embodiment of the present disclosure, a blood pressure cuff adapter includes a substantially rigid body having a distal portion, a proximal portion, a central opening formed at least in part by an inner wall of the body, and a longitudinal axis extending substantially centrally through the opening. The distal portion includes an annular ring having a top surface and a ridge disposed opposite the top surface, the ridge extending substantially perpendicular to the longitudinal axis. The adapter also includes a seal disposed on the top surface of the ring. The seal is configured to form a substantially fluid-tight seal with a surface of a fitting removably attachable to the adapter.

In another example embodiment of the present disclosure, a blood pressure cuff adapter includes a substantially rigid body, the body having a distal portion having a first fluid passage, a first longitudinal axis extending substantially centrally through the first fluid passage, a second fluid passage, a second longitudinal axis extending substantially centrally through the second fluid passage, the first longitudinal axis extending substantially perpendicular to the second longitudinal axis, and a proximal portion fluidly connected to the distal portion. The distal portion includes a ring forming an opening of the distal portion about the first longitudinal axis, the opening configured to accept at least part of a fitting removably attachable to the adapter. The distal portion also includes a ridge formed on a side surface of the distal portion. The distal portion further includes a seal disposed on the ring, the seal configured to form a substantially fluid-tight seal with a surface of the fitting.

In a further example embodiment of the present disclosure, a blood pressure cuff adapter includes a substantially rigid body having a distal portion, a proximal portion, a substantially cylindrical inner wall forming a central opening of the body, the inner wall extending from the distal portion to the proximal portion, and a longitudinal axis extending substantially centrally through the opening. The distal portion includes an annular ring having a top surface and a groove, the groove extending at least partly around the longitudinal axis and being configured to accept a corresponding member of a fitting removably attachable to the adapter. The distal portion also includes a ridge disposed opposite the top surface, the ridge extending substantially perpendicular to the longitudinal axis. The adapter further includes a seal disposed adjacent to the inner wall, the seal configured to form a substantially fluid-tight seal with the fitting.

In another example embodiment, a blood pressure cuff adapter includes a substantially rigid body having a distal portion, a proximal portion, a central opening, and a longitudinal axis extending substantially centrally through the opening. The distal portion includes an annular ring having a top surface and a ridge disposed opposite the top surface, the ridge extending substantially perpendicular to the longitudinal axis. The adapter also includes an annular groove formed by the top surface of the ring, the groove configured to mate with a seal of a fitting removably attachable to the adapter.

BRIEF DESCRIPTION OF THE DRAWINGS

FIG. 6a is a top view of a further example blood pressure cuff adapter and an example fitting removably attached to the adapter.

FIG. 6b is cross-sectional view of the blood pressure cuff adapter and fitting shown in FIG. 6a.

FIG. 7b is a top view of the example blood pressure cuff adapter shown in FIG. 7a.

FIG. 7c is a top view of another example blood pressure cuff adapter.

FIG. 7e is a partial cross-sectional view of an example fitting removably attached to an example blood pressure cuff adapter.

FIG. 7f is another partial cross-sectional view of an example fitting removably attached to an example blood pressure cuff adapter.

FIG. 7g is a further partial cross-sectional view of an example fitting removably attached to an example blood pressure cuff adapter.

FIG. 8a is a top view of a further example blood pressure cuff adapter and an example fitting removably attached to the adapter.

FIG. 8b is cross-sectional view of the blood pressure cuff adapter and fitting shown in FIG. 8a.

FIG. 11 illustrates a cross-sectional view of another example blood pressure cuff adapter and an isometric view of another example fitting configured to mate with the adapter.

FIG. 13a is a cross-sectional view of yet another example blood pressure cuff adapter and an example fitting removably attached to the adapter.

FIG. 13b is another cross-sectional view of the blood pressure cuff adapter and fitting shown in FIG. 13a.

DETAILED DESCRIPTION

Figure 1:
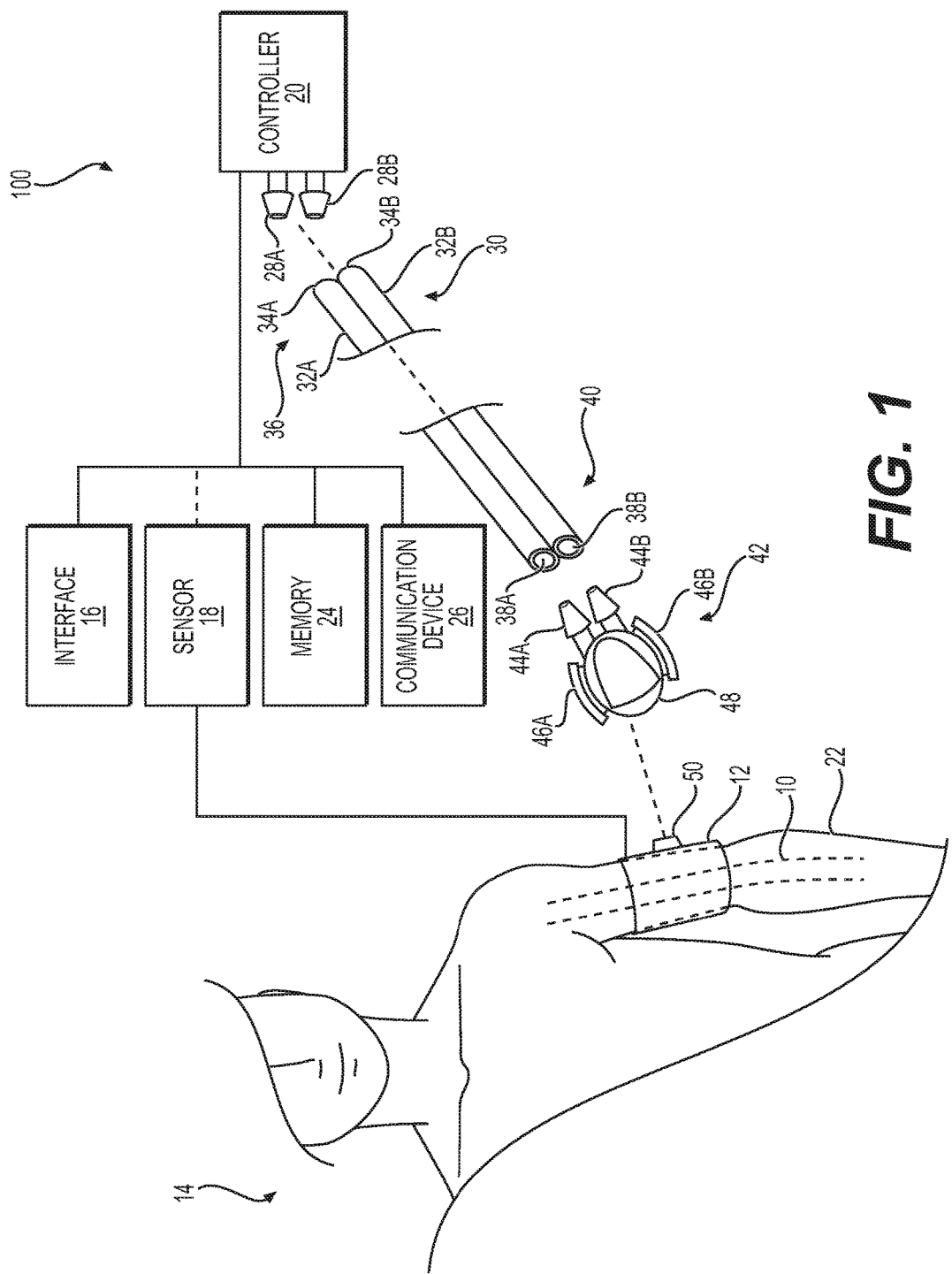
FIG. 1 includes a partial schematic illustration of a patient monitoring system according to an example embodiment of the present disclosure.

FIG. 1 illustrates a patient monitoring system 100, according to an example embodiment of the present disclosure. The system 100 can be configured to monitor a patient, and in some embodiments, to determine a hemodynamic parameter of the patient. As used herein, the term "hemodynamic parameter" can include an indication of cardiac or vascular health, such as, for example, an indication of cardiac, circulatory, or vascular functionality. Specifically, a hemodynamic parameter can include a heart rate, a blood pressure, a vessel compliance, a saturation of hemoglobin with oxygen in arterial blood (i.e., an $SpO_2$ measurement), an aortic index, an augmentation index, reflected wave ratio, or an indication of treatment. Blood pressure can include systolic, suprasystolic, diastolic, or mean atrial pressure. It is understood that such blood pressures may be represented as a systolic blood pressure over a diastolic blood pressure, and that a mean or average blood pressure may be represented as an average systolic blood pressure over an average diastolic blood pressure. Moreover, an indication of treatment can include a parameter reflecting the affect of a drug treatment, or one or more treatments of a disease state.

The system 100 can include a cuff 12 configured to at least to partially occlude the movement of blood through a blood vessel 10 of a patient 14 such as an artery, vein, or the like. In some embodiments, the cuff 12 can be configured to completely occlude an artery of patient 14. In any of the embodiments described herein, however, the system 100 may be tuned and/or otherwise configured to determine one or more hemodynamic parameters of the patient 14, such as a blood pressure of the patient 14, without completely occluding the blood vessel 10. In such embodiments, the system 100, and/or components thereof, may determine the blood pressure of the patient 14 before the cuff 12 is inflated to a pressure associated with complete occlusion of the blood vessel 10 and/or before a systolic blood pressure of the patient 14 is reached. Although shown in FIG. 1 surrounding an arm 22 of the patient 14, the cuff 12 may be adapted for placement on (i.e., around) any suitable body part of patient 14, including, for example, a wrist, a finger, an upper thigh, an ankle, or any other like limb or body part. In addition, one or more cuffs 12 could be placed at different locations about the patient 14 for use with the system 100.

The cuff 12 can include one or more bladders or other like inflatable devices, and the pressure or volume within the cuff 12 may be controlled by any known inflation device (not shown). Such inflation devices can include a pump or similar device configured to controllably inflate and/or deflate the inflatable device of the cuff 12. For example, such inflation devices could supply the cuff 12 with a fluid to increase the pressure or volume of the cuff 12. In other embodiments, one or more inflation devices could include mechanical, electrical, or chemical devices configured to occlusion of the blood vessel 10 via the cuff 12. Such inflation devices may comprise a component of the system 100 and may be included within and/or operably connected to, for example, a controller 20 of the system 100. In some embodiments, such inflation devices can inflate the cuff 12 to or towards a target inflation pressure, and may be configured to generally maintain the cuff 12 at any desired inflation pressure for a desired period of time. In some embodiments, the target inflation pressure may be less than or equal to the systolic pressure of the patient 14. Alternatively, in further embodiments the target pressure may be greater than the systolic pressure of the patient 14. In example embodiments, the system 100 may determine the blood pressure of the patient 14 without inflating the cuff to the systolic pressure. Accordingly, even in embodiments in which algorithms, controllers, and/or other components of the system 100 employ a target inflation pressure that is equal to or greater than the systolic pressure, the system 100 may discontinue inflation of the cuff 12 at an inflation pressure less than such a target inflation pressure. Although such embodiments may use a target inflation pressure equal to or greater than the systolic pressure, discontinuing inflation of the cuff 100 at a pressure below such a target inflation pressure may avoid patient discomfort during blood pressure determination.

The system 100 can further include a sensor 18 configured to receive a signal associated with the patient 14. In some embodiments, the sensor 18 can be configured to receive a signal associated with an at least partially occluded vessel 10 of the patient 14. Such an input signal can arise from blood movement through the partially occluded vessel 10 or from a signal associated with an occluded blood vessel 10. The sensor 18 could sample multiple times at various intervals. In yet other embodiments, the sensor 18 could provide an indication of blood vessel movement, such as, for example, oscillations arising from vascular expansion or contraction. For example, the sensor 18 could be configured to detect a pressure or volume of cuff 12 that may vary periodically with the cyclic expansion and contraction of the blood vessel 10 of the patient 14. In particular, the sensor 18 could determine a blood pressure, various pulses of blood through the blood vessel 10, an oxygen saturation of the blood, or any other hemodynamic parameter associated with the patient 14 using an auscultation, oscillometric, or other known measurement method.

In some embodiments, the sensor 18 could detect a volume or a pressure associated with cuff 12. For example, the sensor 18 could include a pressure transducer or other like pressure sensor, and may be located within, on, or about the cuff 12 or other parts of the system 100. In such embodiments, the sensor 18 may be configured to sense, measure, detect, monitor, calculate, and/or otherwise "determine" one or more blood pressure pulses associated with the patient 14. Each blood pressure "pulse" may be indicative of, for example, the movement of blood through the blood vessel 10 by the heart of the patient 14 during systole, and the number of such pulses per minute may comprise the heart rate of the patient 14.

The controller 20 may comprise and/or otherwise include one or more processors, microprocessors, programmable logic controllers, and/or other like components configured to control one or more operations of the cuff 12, the cuff inflation devices, the sensor 18, and/or other components of the system 100 connected to the controller 20. For example, the controller 20 can control inflation and/or deflation of the cuff 12 via control of the inflation devices described above.

In some embodiments, the controller 20 can sense, measure, detect, monitor, calculate, and/or otherwise determine a blood pressure of the patient 14 based on one or more of the hemodynamic parameters determined by the sensor 18. This determination may be based on one or more output signals received from sensor 18, as described above. In some embodiments, the controller 20 may also include one or more sensors, similar to the sensor 18, configured to sense, measure, detect, monitor, calculate, and/or otherwise determine one or more blood pressure pulses associated with the patient 14, a pressure or volume of cuff 12, and/or any of the other hemodynamic parameters described herein. The controller 20 may also control inflation of cuff 12 (via one or more of the inflation devices described herein) toward a target inflation pressure, or generally maintaining inflation of cuff 12 at about the target pressure. Such a target inflation pressure may be a pressure that is greater than, equal to, or less than, for example, a systolic pressure of the patient 14 and/or the mean arterial pressure of the patient. For example, as noted above, the system 100 may determine the blood pressure of the patient 14 without inflating the cuff to the systolic pressure. Accordingly, even in embodiments in which the controller 20 employs a target inflation pressure that is equal to or greater than the systolic pressure for purposes of cuff inflation, algorithms of the controller 20 may discontinue inflation of the cuff 12 at an inflation pressure less than such a target inflation pressure. Despite the use of such example target inflation pressures, the controller 20 may determine the blood pressure of the patient 14 without completely occluding the blood vessel 10.

Although not shown in FIG. 1, in additional example embodiments, the system 100 can optionally include a signal analysis module. For example, the signal analysis module may be configured to analyze one or more signals received from the sensor 18 using one or more processors of the controller 20. For example, the signal analysis module can include one or more filters configured to filter a signal associated with the sensor 18 or the controller 20. Such filters can include band-pass, high-pass, or low-pass filters.

As illustrated in FIG. 1, the system 100 may also include a memory 24 operably connected to the controller 20. The memory 24 may include, for example, a hard drive, a thumb drive, and/or any other like fixed or removable storage device known in the art. Such memory 24 may comprise random access memory, read-only memory, transient memory, non-transient memory, and/or any other like information storage means. In such embodiments, the memory 24 may be configured to store signals, data, values, curves, thresholds, and/or any other like information received from the sensor 18. The memory 24 may also be configured to store signals, data, values, thresholds, curves, and/or any other like information determined by the controller 20 during the various operations described herein. For example, the memory 24 may be configured to store one or more pressure pulses, pulse profiles, pulse heights, pulse curves, target inflation pressures, pressure thresholds, and/or other like information. Additionally, the memory 24 may be configured to store one or more algorithms, protocols and/or other like programs associated with calculating and/or otherwise determining the blood pressure of the patient 14. Additionally, the memory 24 may be configured to store one or more sets of values corresponding to points on one or more pulse curves. Such information may be recalled and/or otherwise utilized by the controller 20 during one or more blood pressure determination methods described herein.

The system 100 can further include a user interface 16 configured to provide communication to the patient 14 or one or more operators. For example, the user interface 16 could include a display configured to communicate and/or otherwise output one or more hemodynamic parameters. The user interface 16 may further include one or more speakers or other like audio devices configured to communicate and/or otherwise output information to the patient 14 and/or a user operator of the system 100. In further embodiments, the system 100 may include one or more transmitters, network devices, routers, Bluetooth® devices, WiFi® devices, radio devices, and/or other like communication device 26 configured to transmit data to a remote location and/or to a remote device. In such embodiments, the communication device 26 may enable the transmission of information to or from the controller 20. It is understood, that such communication devices 26 may facilitate the transmission of such information via wired or wireless means. For example, in any of the embodiments described herein, one or more components of the system 100, such as the controller 20, may be disposed remote from a remainder of the components of the system 100. In such embodiments, for example, the controller 20 may be disposed in a different location of a healthcare facility than the cuff 12, user interface 16, or other components of the system 100. Alternatively, in further embodiments, the controller 20 may be in a first healthcare facility and a remainder of the components of the system 100 may be located in a second healthcare facility different from the first facility. In such embodiments, the various components of the system 100 may be in communication and/or otherwise operably connected via the communication devices 26 described herein.

In addition to the components outlined above, the system 100 may include various other component, such as, for example, a power source and/or a user input device. One or more components described herein may be combined or may be separate independent components of the system. Moreover, the various components of the system 100 could be integrated into a single processing unit or may operate as separate processors. In operation, one or more processors can be configured to operate in conjunction with one or more software programs to provide the functionality of the system 100. For example, one or more of the components described above with respect to the system 100 may include one or more hardware components and/or one or more software components configured to control operation of such components and/or of the system 100.

The system 100 of the present disclosure may also include one or more components configured to fluidly connect the cuff 12 with the controller 20, and in particular, with one or more inflation devices operably connected to the controller 20. For example, the controller 20 may include first and second connectors 28a, 28b fluidly coupled to one or more of the inflation devices described herein. The first and second connectors 28a, 28b may comprise male barbs or other like connectors defining a respective lumen through which pressurized air or other fluids may pass from the inflation devices to tubing 30 fluidly connected to the one or more connectors 28a, 28b. For example, the tubing 30 may comprise dual-lumen tubing having first and second connected conduit sections 32a, 32b sharing a substantially smooth integrated outer surface. In such embodiments, an orifice 34a of the first section 32a at a proximal end 36 of the tubing 30 may be configured to form a substantially fluid-tight connection with the first connector 28a. Similarly, an orifice 34b of the second section 32b at the proximal end 36 of the tubing 30 may be configured to form a substantially fluid-tight connection with the second connector 28b. Alternatively, in other embodiments, the tubing 30 may comprise single-lumen tubing, and a first section of the single-lumen tubing may be configured to form a substantially fluid-tight connection with the first connector 28a while a second section of the single-lumen tubing 30 may be configured to form a substantially fluid-tight connection with the second connector 28b. For ease of discussion, the tubing 30 shall be described herein as dual-lumen tubing unless otherwise noted. In any of the embodiments described herein, the tubing 30 may comprise a flexible, durable, medically approved material such as a thermoplastic elastomer, and the tubing 30 may be made from processes including extrusion molding.

The first section 32a of the tubing 30 may also include an orifice 38a at a distal end 40 of the tubing 30, and the second section 32b may include a similar orifice 38b at the distal end 40. The orifices 38a, 38b may be configured to form a substantially fluid-tight connection with a fitting 42 of the present disclosure. As will be described in greater detail below, the fitting 42 may have various different configurations, and any of the fittings described herein may be employed by the system 100 in order to assist in fluidly connecting the cuff 12 with the controller 20 and/or other components of the system 100. In some examples, the fitting 42 may comprise a dual-shaft connector (e.g., a connector having two shafts configured to mate with dual lumen tubing 30), while in other examples, the fitting 42 may comprise a single-shaft connector. For ease of discussion, the fitting 42 shall be described herein as dual-shaft connector unless otherwise noted.

The fitting 42 may include, for example, first and second shafts 44a, 44b, and a proximal end portion of the first shaft 44a may be configured to form a substantially fluid-tight connection with the first section 32a of the tubing 30, while a proximal end portion of the second shaft 44b may be configured to form a substantially fluid-tight connection with the second section 32b of the tubing 30. In particular, a barb or other like connector may be formed at proximal end portions of the first and second shafts 44a, 44b, and such barbs may be inserted into the respective orifices 38a, 38b of the tubing 30 to form such a substantially fluid-tight connection between the fitting 42 and the tubing 30. In some examples, the barbs formed at each of the proximal end portions may be substantially similar to and/or the same as the first and second connectors 28a, 28b described above. The first and second shafts 44a, 44b may define respective lumens passing therethrough and configured to fluidly connect, the tubing 30 with, for example, the cuff 12 via one or more adapters 50 of the cuff 12. For example, as will be described in greater detail below, the fitting 42 may be removably attachable to a corresponding adapter 50 of the cuff 12, and a substantially fluid tight seal may be formed between the fitting 42 and such an adapter 50 when the fitting 50 is removably attached to the adapter. The fitting 42 may include one or more grips 46a, 46b connected to a body 48 of the fitting 42, and such grips 46a, 46b may be configured to assist in removably attaching the fitting 42 to the adapter 50. It is understood that when the fitting 42 is removably attached to the blood pressure cuff adapter 50, the fitting 42 may be fluidly connected to the adapter 50 and/or to the cuff 12. Thus, when the fitting 42 is removably attached to the blood pressure cuff adapter 50, the fitting 42 may be configured to direct pressurized air or other fluids to the cuff 12, via the adapter 50, to assist in at least partially inflating the cuff 12.

Figure 2:
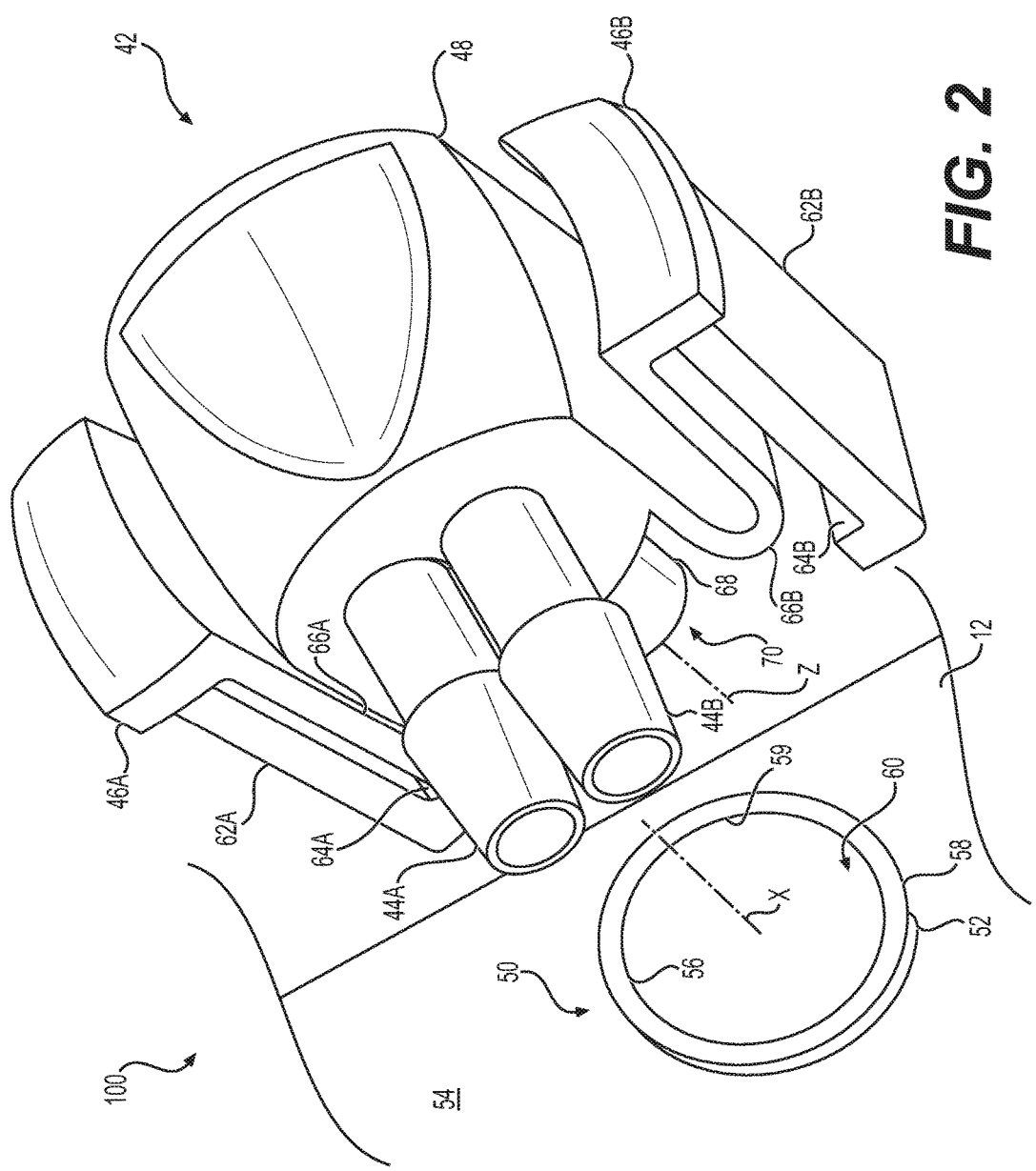
FIG. 2 is an isometric view of an example blood pressure cuff adapter and an example fitting of the present disclosure.

FIG. 2 illustrates the example fitting 42 and the example blood pressure cuff adapter 50 of FIG. 1 in greater detail. As shown in FIG. 2, in an example system 100 or other environment, the grips 46a, 46b of the fitting 42 may extend from the body 48, and at least part of the fitting 42 coupling the grips 46a, 46b to the body 48 may be relatively flexible. For example, the body 48 may be made from a first substantially rigid material, and such a material may include, for example, one or more metals, alloys, plastics, polymers, or other materials. Such materials may include, for example, polyethylene, polypropylene, and/or other medically approved materials. In such examples, the grips 46a, 46b may be connected to the body 48 via respective first and second stands 66a, 66b extending from the body 48. In some examples, the stands 66a, 66b may be made from any of the materials described above with respect to the body 48, while in other examples, one or more of the stands 66a, 66b may be made from a material that is relatively more flexible than the material used to form the body 48. In any such examples, the shape, size, materials, and/or other configuration of the stands 66a, 66b may provide for movement of the respective grips 46a, 46b relative to the body 48 when force is applied to the respective grips 46a, 46b by a user of the fitting 42. Such movement may enable the fitting 42 to be removably attached to the blood pressure cuff adapter 50, and may also enable the fitting 42 to be detached from the adapter 50. For example, the fitting 42 may include one or more arms 62a, 62b extending from a respective grip 46a, 46b and/or from a respective stand 66a, 66b. In such examples, a first arm 62a may extend substantially perpendicularly from the first grip 46a, and a second arm 62b may extend substantially perpendicularly from the second grip 46b. The first and second arms 62a, 62b may include respective first and second shelves 64a, 64b extending substantially parallel to the respective grips 46a, 46b. As can be seen from FIG. 2, the first and second shelves 64a, 64b may also extend substantially perpendicularly from the respective arms 62a, 62b. In particular, such first and second shelves 64a, 64b may include one or more surfaces (e.g., a top surface, a bottom surface opposite the top surface, a side surface, etc.), extending substantially perpendicularly from the respective arms 62a, 62b, and such surfaces may be configured to mate with a corresponding surface of the adapter 50 in order to removably attach the fitting 42 to the adapter. The fitting 42 may also include one or more extensions, passages, and/or other like channels 68 extending from the body 48. In some examples, such as the example shown in FIG. 2, the channel 68 may extend substantially along a longitudinal axis Z of the fitting 42, and the longitudinal axis Z may extend substantially centrally through the channel 68. As will be described in further detail below, in some examples, the channel 68 may form at least part of a central fluid passage extending through at least part of the fitting 42. The channel 68 may also form an opening 70 configured to permit the passage of air or other fluids into the cuff 12 via the fitting 42 (e.g., via the central passage of the fitting 42), and/or to otherwise fluidly connect the fitting 42 with the cuff 12 when the fitting 42 is removably attached to the adapter 50.

As shown in FIG. 2, in some examples the adapter 50 may include a substantially rigid body 52 that is at least partly connected to the cuff 12. For example, the body 52 may include a distal portion extending outwardly from a top or outer surface 54 of the cuff 12. The body 52 may also include a proximal portion embedded within the cuff 12 and/or extending inwardly from the outer surface 54. In some examples, the proximal portion of the body 52 may extend at least partly along and/or may be connected to an inner surface of the cuff 12 disposed opposite the outer surface 54. Alternatively, in any of the example embodiments described herein the adapter 50 may be fluidly connected to the cuff 12 via one or more lengths of tubing 30 and/or other components of the system 100. For instance, in such examples a length of tubing 30 may be fluidly connected to an internal bladder and/or other inflatable portion of the cuff 12, and the length of tubing 30 may extend outwardly from the bladder and/or other inflatable portion by any desired distance (e.g., one foot, 18 inches, two feet, etc.). In such examples, the adapter 50 may be fluidly, removably, permanently, and/or otherwise connected to an end of the tubing 30 opposite the cuff 12, and the adapter 50 may be configured to facilitate a removable and/or releasable connection with the fitting 42 at a location spaced from the cuff 12.

With continued reference to FIG. 2, the body 54 may be made from any of the materials described above with respect to, for example, the fitting 42. In some examples, the adapter 50 may be made from more than one such material. For example, one or more components or other parts of the distal portion may be made from a first material, and one or more components or other parts of the proximal portion may be made from a second material different from the first material. In such examples, the use of such first and second materials may result in the various components or other parts of the body 52 having different rigidities, durabilities, sealing characteristics, and/or other properties. For example, a ridge 58 or other part of the body 52 mating with the shelves 64a, 64b of the fitting 42 may be made from a first relatively rigid material to assist in securely removably attaching the fitting 42 to the adapter 50. In such examples, at least part of a ring 56 (e.g., a top surface and/or an inner wall of the ring 56) or other part of the body 52 forming a substantially fluid-tight seal with a corresponding surface of the fitting 42 may be made from a second relatively flexible material different from the first material to assist in forming such a substantially fluid-tight seal.

In any of the examples described herein, the body 52 of the adapter 50 may also include a central opening 60 at least partially formed by an inner wall 59 of the body 52. For example, the inner wall 59 may comprise a substantially cylindrical inner wall, and the inner wall 59 may define a central fluid passage of the adapter 50 configured to accept air or other fluids delivered to the cuff 12 via the fitting 42. In such examples, the inner wall 59 may have any shape, size, diameter, and/or other configuration such that the inner wall 59 may accept at least part of the channel 68 therein. For example, a substantially cylindrical inner wall 59 may define a substantially circular opening 60 through which at least part of the channel 68 may pass when the fitting 42 is removably attached to the adapter 50. In this way, at least part of the channel 68 may extend into and/or may otherwise be disposed within the inner wall 59, via the opening, when the fitting 42 is removably attached to the adapter 50. In any of the examples described herein, the body 52 may further include a longitudinal axis X, and in such examples, the longitudinal axis X may extend substantially centrally through the opening 60 and/or through the substantially cylindrical inner wall 59. As will be described in greater detail below, in any of the examples described herein the ring 56 formed by the body 52 may comprise a substantially annular ring, flange, and/or other portion of the adapter 50, and the ring 56 may include a top surface disposed opposite the proximal portion of the body 52. In such examples, the ridge 58 may be disposed opposite the top surface of the ring 56 an, in some examples, the ridge 58 may comprise at least part of a bottom surface of the ring 56. At least part of the ridge 58 and/or at least another part of the bottom surface of the ring 56 may be configured to mate with the shelves 64a, 64b of the fitting 42 to assist in retaining the fitting 42 and/or otherwise removably attaching the fitting 42 to the adapter 50. In some examples, at least part of the ridge 58 and/or at least another part of the bottom surface of the ring 56 may extend substantially perpendicular to the longitudinal axis X of the body 52.

Figure 3:
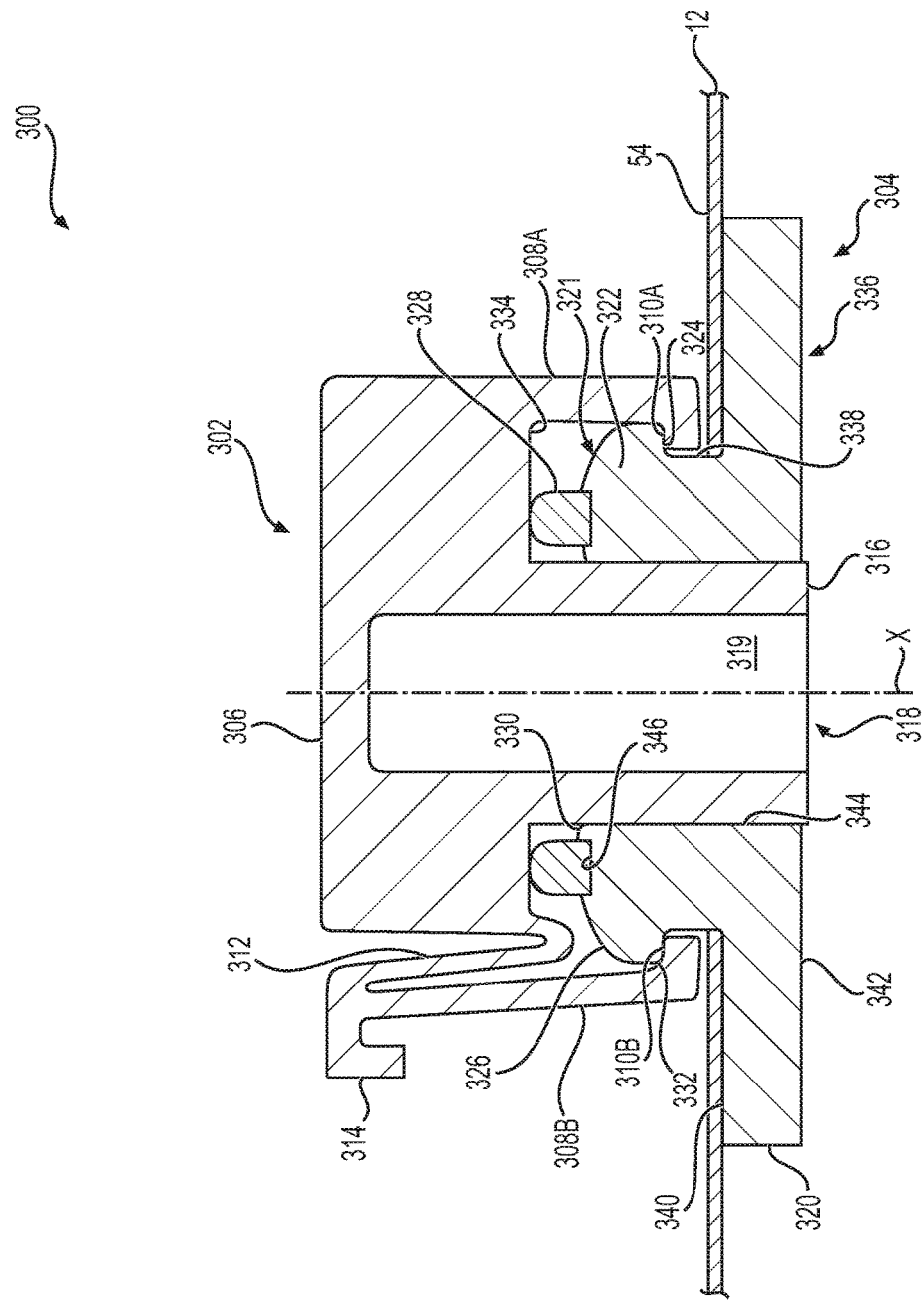
FIG. 3 is a cross-sectional view of an example blood pressure cuff adapter and an example fitting removably attached to the adapter.

As shown in FIG. 3, an example system 300 or other environment may include a fitting 302 and/or a blood pressure cuff adapter 304, and in such systems, the example fitting 302 may be removably attachable to such an adapter 304. The fitting 302 and/or the adapter 304 may include various structures and/or other components configured to assist in forming such a removable connection, and one or more such components may also assist in forming a substantially fluid-tight seal between the fitting 302 and the adapter 304 when the fitting 302 is removably attached to the adapter 304. In example embodiments, any of the structures, functions, and/or other aspects of the fitting 42 described herein with respect to FIGS. 1 and 2 may be included in the fitting 302 and/or in any of the other example fittings described herein. Likewise, any of the structures, functions, and/or other aspects of the adapter 50 described herein with respect to FIGS. 1 and 2 may be included in the adapter 304 and/or in any of the other example blood pressure cuff adapters described herein. Further, one or more of the structures, functions, and/or features of the fitting 302, and/or of the adapter 304, may be incorporated into any of the fittings or adapters of the present disclosure.

In the example system 300, the fitting 302 may include a substantially rigid body 306, and one or more arms 308a, 308b extending from the body 306. The first and second arms 308a, 308b may also include respective shelves 310a, 310b formed at respective distal ends of the arms 308a, 308b. At least one of the arms 308a, 308b and/or at least one of the shelves 310a, 310b may be substantially similar to and/or the same as the arms 62a, 62b and/or the shelves 64a, 64b described above. For example, the arm 308b may be movably connected to the body 306 via at least one stand 312 extending from the body 306. As can be seen from FIG. 3, the first and second shelves 310a, 310b may extend substantially perpendicularly from the respective arms 308a, 308b. In particular, such first and second shelves 310a, 310b may include one or more surfaces (e.g., a top surface, a bottom surface opposite the top surface, a side surface, etc.), extending substantially perpendicularly from the respective arms 308a, 308b, and such surfaces may be configured to mate with a corresponding surface of the adapter 304 in order to removably attach the fitting 302 to the adapter 304.

At least one of the body 306, stands 312, arms 308a, 308b, shelves 310a, 310b, and/or other components of the fitting 302 may be made from any of the materials described above with respect to the body 48. In any such examples, the shape, size, materials, and/or other configuration of the stand 312 may provide for movement of the corresponding shelf 310b relative to the body 306 when force is applied to a grip 314 associated with the stand 312. Such movement may enable the fitting 302 to be removably attached to the blood pressure cuff adapter 304, and may also enable the fitting 302 to be detached from the adapter 304. For example, in the system 300 the arm 308a and/or the shelf 310a may remain substantially stationary relative to the body 306 when the fitting 302 is removably attached to and/or detached from the blood pressure cuff adapter 304.

The fitting 302 may also include one or more extensions, passages, and/or other like channels 316 extending from the body 306. In some examples, the channel 316 may extend substantially along the longitudinal axis Z (FIG. 2) of the fitting 302, and the longitudinal axis Z may extend substantially centrally through the channel 316. The channel 316 may form an opening 318 configured to permit the passage of air or other fluids into the cuff 12 via the fitting 302, and/or to otherwise fluidly connect the fitting 302 with the cuff 12, when the fitting 302 is removably attached to the adapter 304. The fitting 302 may further include a central fluid passage 319 extending at least partially through the body 306. For example, the channel 316 may form at least part of the central fluid passage 319, and the longitudinal axis Z (FIG. 2) may extend substantially centrally through at least part of the central passage 319. In such examples, the opening 318 of the channel 316 may comprise an opening of the central passage 319.

As noted above with respect to the adapter 50 of FIG. 2, the adapter 304 may include a substantially rigid body 320 that is at least partly connected to the cuff 12. For example, the body 320 may include a distal portion 321 extending outwardly from the outer surface 54 of the cuff 12. The body 320 may also include a proximal portion 336 embedded within the cuff 12 and/or extending inwardly from the outer surface 54. In some examples, a top surface 340 of the proximal portion 336 may extend at least partly along and/or may be connected to an inner surface of the cuff 12 disposed opposite the outer surface 54. The body 320 of the adapter 304 may be made from any of the materials described above with respect to, for example, the fitting 42. In some examples, the adapter 304 may be made from more than one such material. For example, one or more components or other parts of the distal portion 321 may be made from a first material, and one or more components or other parts of the proximal portion 336 may be made from a second material different from the first material. As noted above with respect to the adapter 50 of FIG. 2, in such examples, the use of such first and second materials may result in the various components or other parts of the body 320 having different rigidities, durabilities, sealing characteristics, and/or other properties.

The distal portion 321 of the adapter 304 may include an annular ring 322 having a top surface 326 and a ridge 324 disposed opposite the top surface 326. The ridge 324 may comprise at least part of a bottom surface of the ring 322. In such examples, at least part of the ridge 324 and/or at least another part of the bottom surface of the ring 322 may be configured to mate with the shelves 310a, 310b of the fitting 302 to assist in retaining the fitting 302 and/or otherwise removably attaching the fitting 302 to the adapter 304. In some examples, at least part of the ridge 324 and/or at least another part of the bottom surface of the ring 322 may extend substantially perpendicular to a longitudinal axis X of the body 320. Additionally, the adapter 304 may include a substantially cylindrical sidewall 338 extending from the ridge 324 to the top surface 340 of the proximal portion 336. Such a sidewall 338 may space the ridge 324 from the top surface 340 such that the shelves 310a, 310b of the fitting 302 may have room to mate with the ridge 324 beneath the ring 322.

The top surface 326 of the ring 322 may be substantially convex, substantially concave, substantially curved, substantially tapered, and/or any other configuration in order to assist in removably attaching the fitting 302 to the adapter 304. In some examples, the top surface 326 of the ring 322 may comprise a convex surface extending radially away from the longitudinal axis X of the body 320 from a distal end (e.g., a radially innermost end) 330 of the top surface 326 to a proximal end (e.g., a radially outermost end) 332 of the top surface 326. In such examples, the curved top surface 326 may comprise a camming surface along which at least part of the arm 308b and/or other components of the fitting 302 may slide as the fitting 302 is removably attached to the adapter 304.

The system 300 may also include one or more O-rings, gaskets, and/or other seals 328 configured to form a substantially fluid-tight seal between the fitting 302 and the adapter 304 when the fitting 302 is removably attached to the adapter 304. For example, in any of the example embodiments described herein, at least one seal 328 may be attached to, adhered to, embedded substantially within, formed integrally with, and/or otherwise connected to either an outer surface 334 of the fitting 302 or to the top surface 326 of the ring 326 to facilitate forming such a fluid-tight seal. In the example system 300 of FIG. 3, at least part (e.g., a base) of the seal 328 may be disposed within an annular groove 346 formed by the top surface 326 of the ring 322. In such examples, the seal 328 may engage the outer surface 334 of the fitting 302 to form a substantially fluid-tight seal with the fitting 302 when the fitting 302 is removably attached to the adapter 304. Alternatively, in any of the example embodiments described herein, the seal 328 may be attached to, adhered to, embedded substantially within, formed integrally with, and/or otherwise connected to the outer surface 334 of the fitting 302, and may be configured to engage the top surface 326 to form such a substantially fluid-tight seal. In example embodiments in which the seal 328 is formed integrally with the adapter 304, the seal 328 may comprise, for example, a relatively flexible and/or a relatively thin portion of the ring 322. Alternatively, in example embodiments in which the seal 328 is formed integrally with the fitting 302, the seal 328 may comprise a relatively flexible and/or a relatively thin portion of the outer surface 334. In still further example embodiments, the seal 328 may be separable from (e.g., removably attached to) either the fitting 302 or the adapter 304. In such examples, the seal 328 may be press fit within, dove-tailed within, and/or otherwise at least partly disposed within a groove 346, channel, and/or other structure formed by either the fitting 302 or the adapter 304 to facilitate such removable attachment thereto.

Further, the body 320 of the adapter 304 may also include a central opening (as shown more clearly in FIG. 2) at least partially formed by an inner wall 344 of the body 320. For example, the inner wall 344 of the body 320 may comprise a substantially cylindrical inner wall, and the inner wall 344 may define a central fluid passage of the adapter 304 configured to accept air or other fluids delivered to the cuff 12 via the fitting 302. In such examples, the inner wall 344 may have any shape, size, diameter, and/or other configuration such that the inner wall 344 may accept at least part of the channel 316 therein. For example, at least part of the channel 316 may pass through the central opening of the inner wall 344, proximate the distal end 330 of the top surface 326, when the fitting 302 is removably attached to the adapter 304. The inner wall 344 may extend from the distal end 330 of the top surface 326 to a bottom surface 342 of the body 320 formed by the proximal portion 326. In any of the examples described herein, the body 320 may further include a longitudinal axis X, and in such examples, the longitudinal axis X may extend substantially centrally through the central fluid passage of the adapter 304 formed by the substantially cylindrical inner wall 344.

Figure 4:
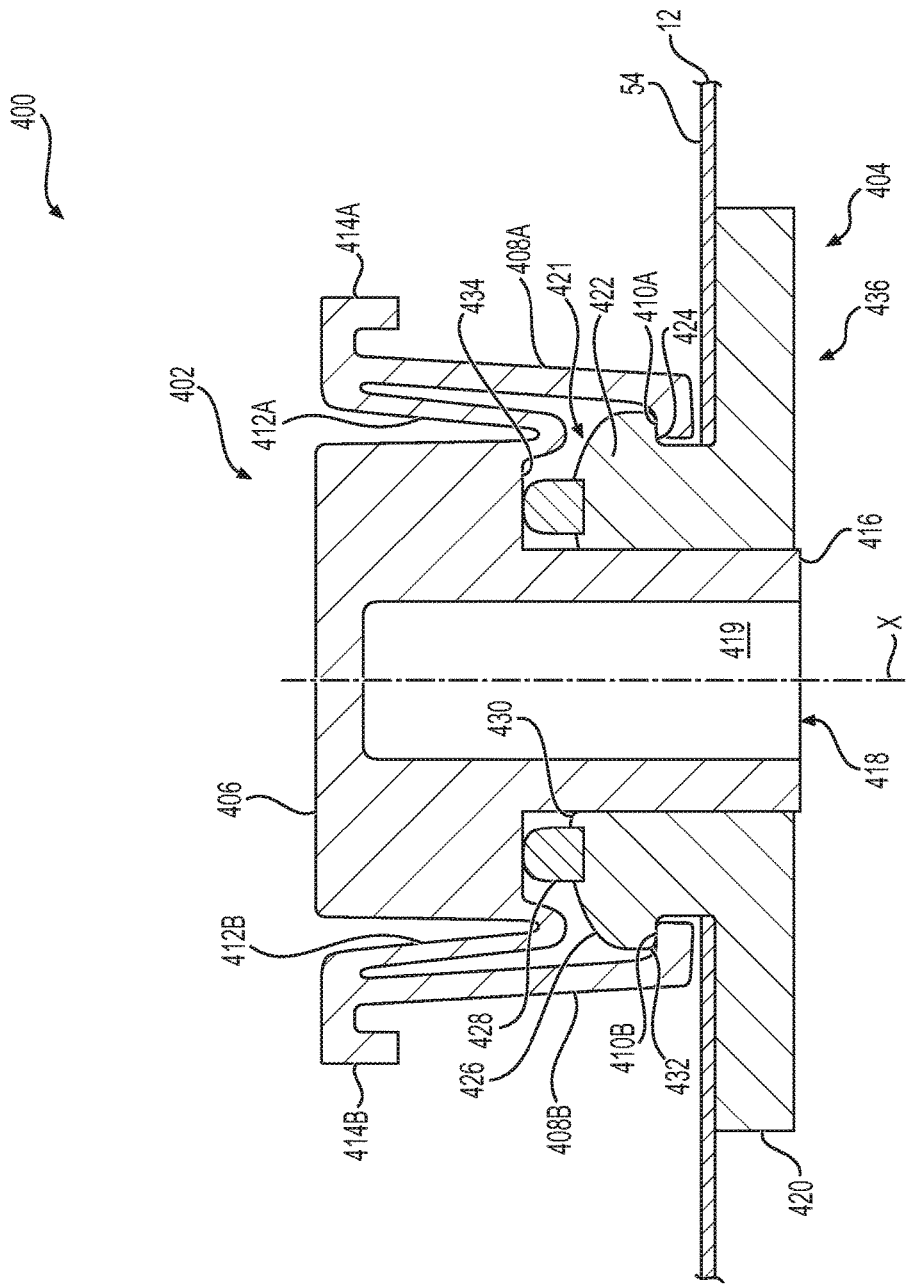
FIG. 4 a cross-sectional view of another example blood pressure cuff adapter and an example fitting removably attached to the adapter.
Figure 4A:
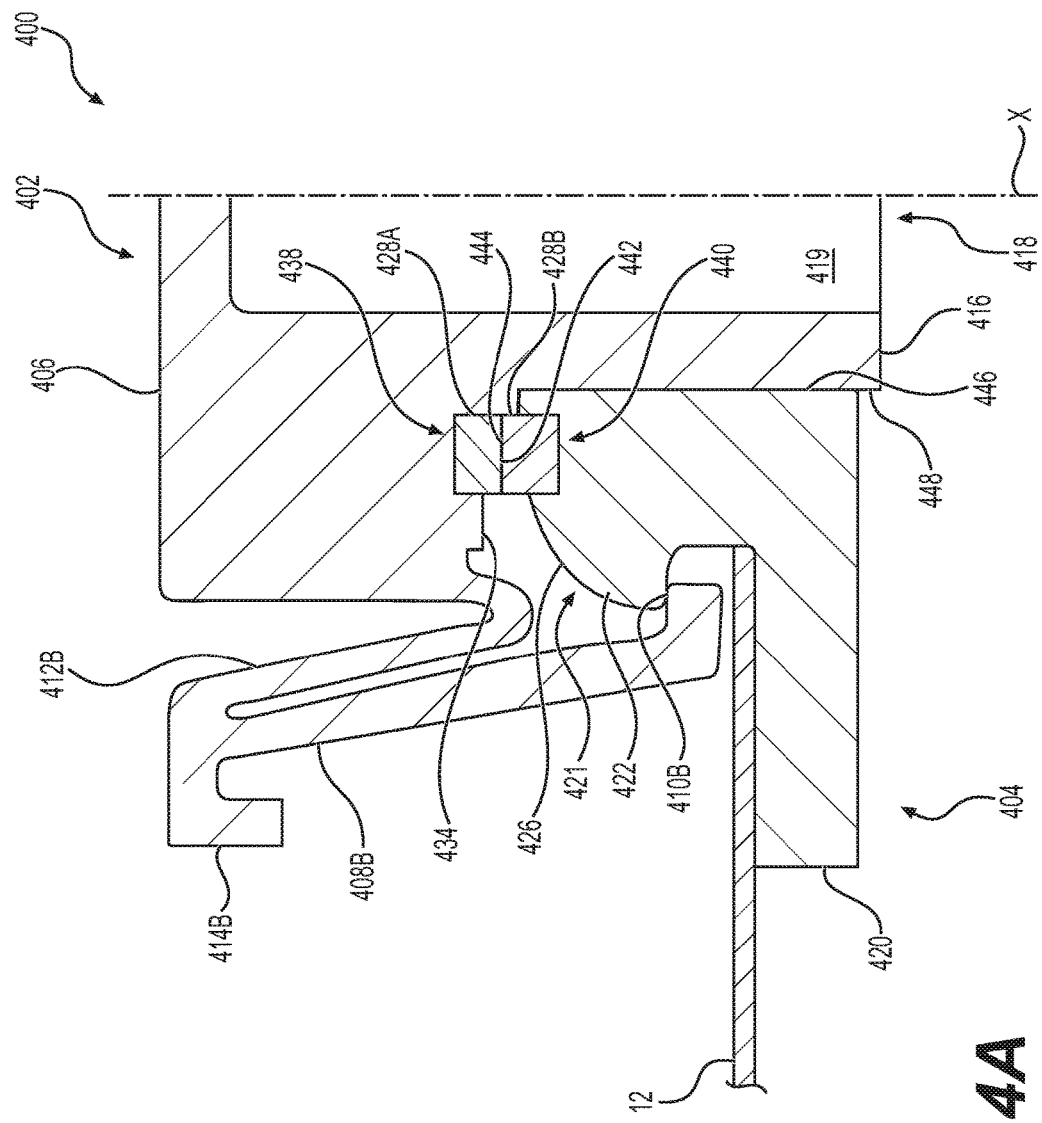
FIG. 4a is a partial cross-sectional view of still another example blood pressure cuff adapter and an example fitting removably attached to the adapter.

As shown in FIGS. 4 and 4a, an example system 400 or other environment of the present disclosure may include a fitting 402 that is substantially similar to the fitting 302, and/or may include a blood pressure cuff adapter 404 that is substantially similar to the blood pressure cuff adapter 304. In such systems 400, the example fitting 402 may be removably attachable to such an adapter 404, and unlike the fitting 302 illustrated in FIG. 3, the fitting 402 may include a pair of stands 412a, 412b movably connecting respective arms 408a, 408b of the fitting 402 to a body 406 of the fitting 402. The fitting 402 and/or the adapter 404 may include various structures and/or other components configured to assist in forming a removable connection therebetween, and one or more such components may also assist in forming a substantially fluid-tight seal between the fitting 402 and the adapter 404 when the fitting 402 is removably attached to the adapter 404. In example embodiments, any of the structures, functions, and/or other aspects of the various fittings described herein may be included in the fitting 402. Likewise, any of the structures, functions, and/or other aspects of the various adapters described herein may be included in the adapter 404. Further, one or more of the structures, functions, and/or features of the fitting 402, and/or of the adapter 404, may be incorporated into any of the fittings or adapters of the present disclosure.

In the example system 400, various components of the fitting 402 may be substantially similar to corresponding components of the fitting 302, and various components of the adapter 404 may be substantially similar to corresponding components of the adapter 304. For example, the fitting 402 may include a substantially rigid body 406, and one or more arms 408a, 408b extending from the body 406. The first and second arms 408a, 408b may also include respective shelves 410a, 410b formed at respective distal ends of the arms 408a, 408b. In such examples, the arm 408a may be movably connected to the body 406 via a stand 412a extending from the body 406, and the arm 408b may be movably connected to the body 406 via a stand 412b extending from the body 406. As can be seen from FIG. 4, the first and second shelves 410a, 410b may extend substantially perpendicularly from the respective arms 408a, 408b. In particular, such first and second shelves 410a, 410b may include one or more surfaces (e.g., a top surface, a bottom surface opposite the top surface, a side surface, etc.), extending substantially perpendicularly from the respective arms 408a, 408b, and such surfaces may be configured to mate with a corresponding surface of the adapter 404 in order to removably attach the fitting 402 to the adapter 404.

At least one of the body 406, stands 412a, 412b, arms 408a, 408b, shelves 410a, 410b, and/or other components of the fitting 402 may be made from any of the materials described above with respect to the body 48. In any such examples, the shape, size, materials, and/or other configuration of the stands 412a, 412b may provide for movement of the corresponding arms 408a, 408b and/or shelves 410a, 410b relative to the body 406 when force is applied to respective grips 414a, 414b associated with the stands 412a, 412b. Such movement may enable the fitting 402 to be removably attached to the blood pressure cuff adapter 404, and may also enable the fitting 402 to be detached from the adapter 404.

The fitting 402 may also include one or more extensions, passages, and/or other like channels 416 extending from the body 406. In some examples, the channel 416 may extend substantially along the longitudinal axis Z (FIG. 2) of the fitting 402, and the longitudinal axis Z may extend substantially centrally through the channel 416. The channel 416 may form an opening 418 configured to permit the passage of air or other fluids into the cuff 12 via the fitting 402, and/or to otherwise fluidly connect the fitting 402 with the cuff 12, when the fitting 402 is removably attached to the adapter 404. The fitting 402 may further include a central fluid passage 419 extending at least partially through the body 406. For example, the channel 416 may form at least part of the central fluid passage 419 of the fitting 402, and the longitudinal axis Z (FIG. 2) may extend substantially centrally through at least part of the central passage 419. In such examples, the opening 418 of the channel 416 may comprise an opening of the central passage 419.

As noted above with respect to the adapter 50 of FIG. 2, the adapter 404 may include a substantially rigid body 420 that is at least partly connected to the cuff 12. For example, the body 420 may include a distal portion 421 extending outwardly from the outer surface 54 of the cuff 12. The body 420 may also include a proximal portion 436 embedded within the cuff 12 and/or extending inwardly from the outer surface 54. In some examples, a top surface of the proximal portion 436 may extend at least partly along and/or may be connected to an inner surface of the cuff 12 disposed opposite the outer surface 54. The body 420 of the adapter 404 may be made from any of the materials described above with respect to, for example, the fitting 42. In some examples, the adapter 404 may be made from more than one such material. For example, one or more components or other parts of the distal portion 421 may be made from a first material, and one or more components or other parts of the proximal portion 436 may be made from a second material different from the first material. As noted above with respect to the adapter 50 of FIG. 2, in such examples, the use of such first and second materials may result in the various components or other parts of the body 420 having different rigidities, durabilities, sealing characteristics, and/or other properties.

The distal portion 421 of the adapter 404 may include an annular ring 422 having a top surface 426 and a ridge 424 disposed opposite the top surface 426. The ridge 424 may comprise at least part of a bottom surface of the ring 422. In such examples, at least part of the ridge 424 and/or at least another part of the bottom surface of the ring 422 may be configured to mate with the shelves 410a, 410b of the fitting 402 to assist in retaining the fitting 402 and/or otherwise removably attaching the fitting 402 to the adapter 404. In some examples, at least part of the ridge 424 and/or at least another part of the bottom surface of the ring 422 may extend substantially perpendicular to a longitudinal axis X of the body 420. Additionally, the adapter 404 may include a substantially cylindrical sidewall extending from the ridge 424 to the top surface of the proximal portion 436. Such a sidewall may space the ridge 424 from the top surface of the proximal portion 436 such that the shelves 410a, 410b of the fitting 402 may have room to mate with the ridge 424 beneath the ring 422.

The top surface 426 of the ring 422 may be substantially convex, substantially concave, substantially curved, substantially tapered, and/or any other configuration in order to assist in removably attaching the fitting 402 to the adapter 404. In some examples, the top surface 426 of the ring 422 may comprise a convex surface extending radially away from the longitudinal axis X of the body 420 from a distal end 430 of the top surface 426 to a proximal end 432 of the top surface 426. In such examples, the curved top surface 426 may comprise a camming surface along which at least part of the arms 408a, 408b and/or other components of the fitting 402 may slide as the fitting 402 is removably attached to the adapter 404.

The system 400 may also include one or more O-rings, gaskets, and/or other seals configured to form a substantially fluid-tight seal between the fitting 402 and the adapter 404 when the fitting 402 is removably attached to the adapter 404. For example, at least one seal 428 (FIG. 4) may be attached to, adhered to, embedded substantially within, and/or otherwise connected to either an outer surface 434 of the fitting 402 or to the top surface 426 of the ring 422 to facilitate forming such a fluid-tight seal. In the example system 400 of FIG. 4, at least part (e.g., a base) of the seal 428 may be disposed within an annular groove formed by the top surface 426 of the ring 422. In such examples, the seal 428 may engage the outer surface 434 of the fitting 402 proximate a perimeter and/or outer wall of the channel 416 to form a substantially fluid-tight seal with the fitting 402 when the fitting 402 is removably attached to the adapter 404. Alternatively, the seal 428 may be attached to, adhered to, embedded substantially within, and/or otherwise connected to the outer surface 434 of the fitting 402, and may be configured to engage the top surface 426 of the adapter 404 to form such a substantially fluid-tight seal.

As shown in the partial cross-section of FIG. 4a, in an alternative example a first seal 428a may be attached to, adhered to, embedded substantially within, formed integrally with, and/or otherwise connected to the outer surface 434 of the fitting 402, and a second seal 428b may be attached to, adhered to, embedded substantially within, formed integrally with, and/or otherwise connected to the top surface 426 of the ring 422. In such embodiments, the first seal 428a may be configured to engage contact, interlock, and/or otherwise mate with the second seal 428b when the fitting 402 is removably attached to the adapter 402, thereby forming such a fluid-tight seal. In the example system 400 of FIG. 4a, at least part (e.g., a base 438) of the first seal 428a may be disposed within an annular groove formed by the outer surface 434 of the fitting 402, and at least part (e.g., a base 440) of the second seal 428b may be disposed within a similar annular groove formed by the top surface 426 of the ring 422. In such examples, the first seal 428a may include a sealing surface 442 disposed opposite the base 438, and the second seal 428b may include a sealing surface 444 opposite the base 440. Accordingly, the sealing surface 442 of the first seal 428a may engage contact, interlock, and/or otherwise mate with the sealing surface 444 of the second seal 428b when the fitting 402 is removably attached to the adapter 402 to form a fluid-tight seal therewith.

Further, the body 420 of the adapter 404 may also include a central opening (as shown more clearly in FIG. 2) at least partially formed by an inner wall 446 (FIG. 4a) of the body 420. In such examples, the longitudinal axis X of the body 420 may extend substantially centrally through the central fluid passage of the adapter 404 formed by the substantially cylindrical inner wall 446 of the adapter 404. The central opening, inner wall 446, and central fluid passage of the adapter 404 may be substantially similar to the central opening, inner wall 344, and central fluid passage described above with respect to FIG. 3. In such examples, a substantially cylindrical outer wall 448 of the channel 416 may be disposed adjacent and/or at least partly in contact with the inner wall 446 of the adapter 404 when the fitting 402 is removably attached to the adapter 404.

Figure 5:
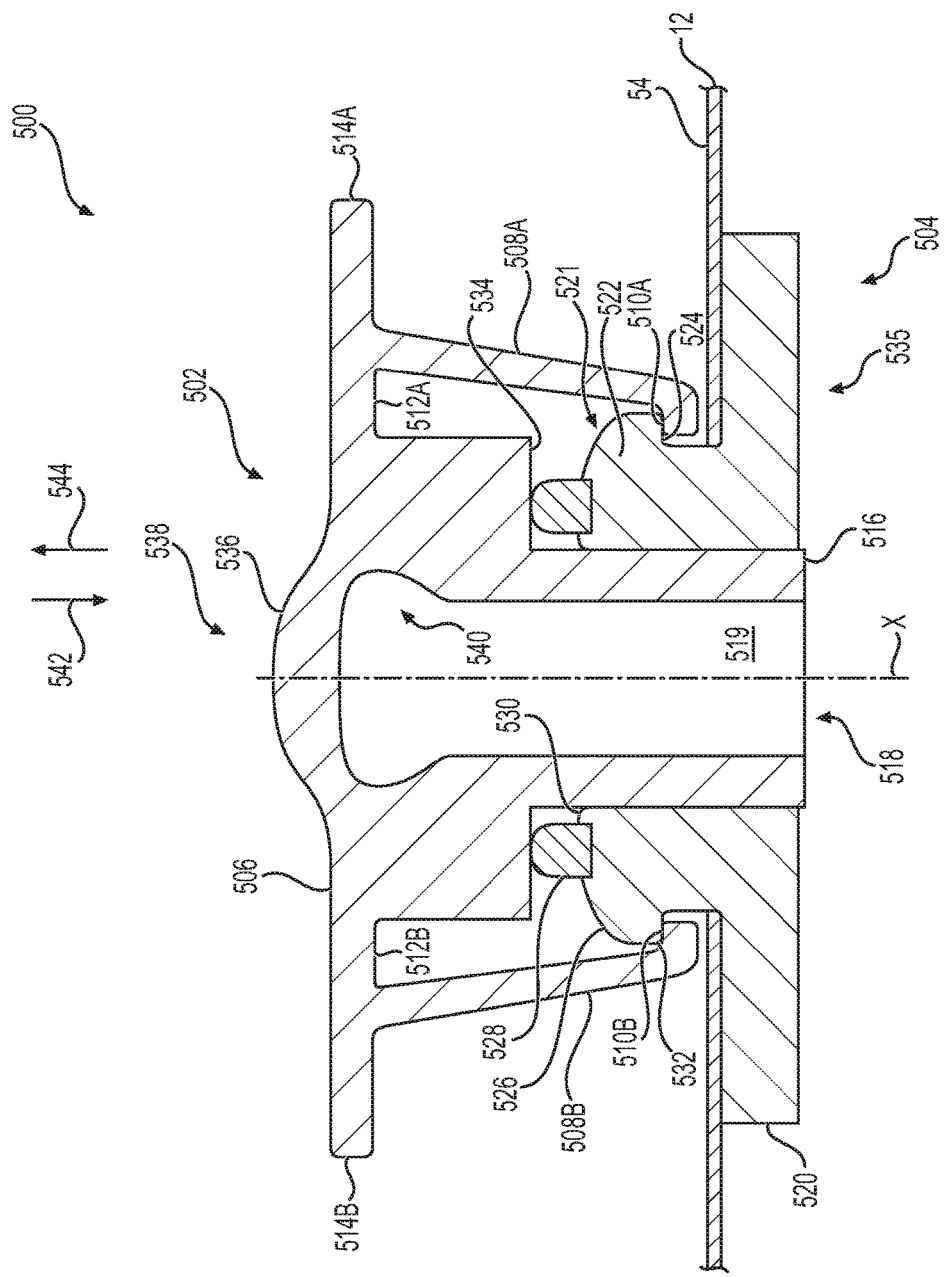
FIG. 5 is cross-sectional view of yet another example blood pressure cuff adapter and an example fitting removably attached to the adapter.

As shown in FIG. 5, an example system 500 or other environment of the present disclosure may include a fitting 502 that is substantially similar to the fitting 402, and/or may include a blood pressure cuff adapter 504 that is substantially similar to the blood pressure cuff adapter 404. In such systems 500, the example fitting 502 may be removably attachable to such an adapter 504, and in such a system 500, the stands 412a, 412b described above with respect to FIG. 4 may be omitted. Instead, the fitting 502 may include a pair of arms extending from the body of the fitting 502, and the fitting 502 may also include a relatively flexible diaphragm at a substantially central top portion of the body. Applying a downward force to the diaphragm while applying an upward force to one or more grips associated with the arms may assist in removably attaching the fitting 502 to the adapter 504 and/or detaching the fitting 502 from the adapter 504. In example embodiments, any of the structures, functions, and/or other aspects of the various fittings described herein may be included in the fitting 502. Likewise, any of the structures, functions, and/or other aspects of the various adapters described herein may be included in the adapter 504. Further, one or more of the structures, functions, and/or features of the fitting 502, and/or of the adapter 504, may be incorporated into any of the fittings or adapters of the present disclosure.

In the example system 500, various components of the fitting 502 may be substantially similar to corresponding components of the fitting 402, and various components of the adapter 504 may be substantially similar to corresponding components of the adapter 404. For example, the fitting 502 may include a substantially rigid body 506, and one or more arms 508a, 508b extending from the body 506. The first and second arms 508a, 508b may also include respective shelves 510a, 510b formed at respective distal ends of the arms 508a, 508b. In the embodiment of FIG. 5, the arms 508a, 508b may be movably connected to the body 506 via a direct connection with the body 506 and/or via one or more posts 512a, 512b or other pieces of material extending substantially laterally from the body 506 to proximal portions of the respective arms 508a, 508b. As can be seen from FIG. 5, the first and second shelves 510a, 510b may extend substantially perpendicularly from the respective arms 508a, 508b. In particular, such first and second shelves 510a, 510b may include one or more surfaces (e.g., a top surface, a bottom surface opposite the top surface, a side surface, etc.), extending substantially perpendicularly from the respective arms 508a, 508b, and such surfaces may be configured to mate with a corresponding surface of the adapter 504 in order to removably attach the fitting 502 to the adapter 504.

At least one of the body 506, posts 512a, 512b, arms 508a, 508b, shelves 510a, 510b, and/or other components of the fitting 502 may be made from any of the materials described above with respect to the body 48. In any such examples, the shape, size, materials, and/or other configuration of the posts 512a, 512b may provide for movement of the corresponding arms 508a, 508b and/or shelves 510a, 510b relative to the body 506 when force is applied to respective grips 514a, 514b connected to the arms 508a, 508b. For example, the fitting 502 may include a diaphragm 536 disposed at a substantially central top portion 538 of the body 506. In such examples, the diaphragm 536 may comprise a relatively thin portion of the body 506, and the location, thickness, and/or other configurations of the diaphragm 536 may enable the body 506 to flex when a downward force in the direction of arrow 542 is applied to the diaphragm 536. In such examples, the body 506 may also include a substantially rounded, substantially hollow internal portion 540 disposed opposite the top portion 538. Such a substantially hollow internal portion 540 may be configured to increase the flexibility of the body 506. In particular, the substantially hollow internal portion 540 may increase the distance and/or degree to which the body 506 flexes when a downward force in the direction of arrow 542 is applied to the diaphragm 536. In use, a healthcare practitioner may apply an upward force in the direction of arrow 544 to one or both of the grips 514a, 514b while, at the same time, applying a downward force to the diaphragm 536 in the direction of arrow 542. The application of one or more such forces may cause one or both of the shelves 510a, 510b to move laterally away from a central longitudinal axis Z (FIG. 2) of the fitting 502. Such movement may enable the fitting 502 to be removably attached to the blood pressure cuff adapter 504, and may also enable the fitting 502 to be detached from the adapter 504. It is understood that, in an alternate embodiment, the grips 514a, 514b may be replaced with a substantially annular, substantially circular, and/or substantially disc-shaped structure substantially surrounding the diaphragm 536 and configured to receive the upward force described above in the direction of arrow 544.

The fitting 502 may also include one or more extensions, passages, and/or other like channels 516 extending from the body 506. In some examples, the channel 516 may extend substantially along the longitudinal axis Z (FIG. 2) of the fitting 502, and the longitudinal axis Z may extend substantially centrally through the channel 516. The channel 516 may form an opening 518 configured to permit the passage of air or other fluids into the cuff 12 via the fitting 502, and/or to otherwise fluidly connect the fitting 502 with the cuff 12, when the fitting 502 is removably attached to the adapter 504. The fitting 502 may further include a central fluid passage 519 extending at least partially through the body 506. For example, the channel 516 and/or the substantially hollow internal portion 540 may form at least part of the central fluid passage 519 of the fitting 502, and the longitudinal axis Z (FIG. 2) may extend substantially centrally through at least part of the central passage 519. In such examples, the opening 518 of the channel 516 may comprise an opening of the central passage 519.

As noted above with respect to the adapter 50 of FIG. 2, the adapter 504 may include a substantially rigid body 520 that is at least partly connected to the cuff 12. For example, the body 520 may include a distal portion 521 extending outwardly from the outer surface 54 of the cuff 12. The body 520 may also include a proximal portion 535 embedded within the cuff 12 and/or extending inwardly from the outer surface 54. In some examples, a top surface of the proximal portion 535 may extend at least partly along and/or may be connected to an inner surface of the cuff 12 disposed opposite the outer surface 54. The body 520 of the adapter 504 may be made from any of the materials described above with respect to, for example, the fitting 42. In some examples, the adapter 504 may be made from more than one such material. For example, one or more components or other parts of the distal portion 521 may be made from a first material, and one or more components or other parts of the proximal portion 535 may be made from a second material different from the first material. As noted above with respect to the adapter 50 of FIG. 2, in such examples, the use of such first and second materials may result in the various components or other parts of the body 520 having different rigidities, durabilities, sealing characteristics, and/or other properties.

The distal portion 521 of the adapter 504 may include an annular ring 522 having a top surface 526 and a ridge 524 disposed opposite the top surface 526. The ridge 524 may comprise at least part of a bottom surface of the ring 522. In such examples, at least part of the ridge 524 and/or at least another part of the bottom surface of the ring 522 may be configured to mate with the shelves 510a, 510b of the fitting 502 to assist in retaining the fitting 502 and/or otherwise removably attaching the fitting 502 to the adapter 504. In some examples, at least part of the ridge 524 and/or at least another part of the bottom surface of the ring 522 may extend substantially perpendicular to a longitudinal axis X of the body 520. Additionally, the adapter 504 may include a substantially cylindrical sidewall extending from the ridge 524 to the top surface of the proximal portion 535. Such a sidewall may space the ridge 524 from the top surface of the proximal portion 535 such that the shelves 510a, 510b of the fitting 502 may have room to mate with the ridge 524 beneath the ring 522.

The top surface 526 of the ring 522 may be substantially convex, substantially concave, substantially curved, substantially tapered, and/or any other configuration in order to assist in removably attaching the fitting 502 to the adapter 504. In some examples, the top surface 526 of the ring 522 may comprise a convex surface extending radially away from the longitudinal axis X of the body 520 from a distal end 530 of the top surface 526 to a proximal end 532 of the top surface 526. In such examples, the curved top surface 526 may comprise a camming surface along which at least part of the arms 508a, 508b and/or other components of the fitting 502 may slide as the fitting 502 is removably attached to the adapter 504.

The system 500 may also include one or more O-rings, gaskets, and/or other seals 528 configured to form a substantially fluid-tight seal between the fitting 502 and the adapter 504 when the fitting 502 is removably attached to the adapter 504. For example, at least one seal 528 may be attached to, adhered to, embedded substantially within, and/or otherwise connected to either an outer surface 534 of the fitting 502 or to the top surface 526 of the ring 522 to facilitate forming such a fluid-tight seal. In the example system 500 of FIG. 5, at least part (e.g., a base) of the seal 528 may be disposed within an annular groove formed by the top surface 526 of the ring 522. In such examples, the seal 528 may engage the outer surface 534 of the fitting 502 proximate a perimeter and/or outer wall of the channel 516 to form a substantially fluid-tight seal with the fitting 502 when the fitting 502 is removably attached to the adapter 504. Alternatively, the seal 528 may be attached to, adhered to, embedded substantially within, and/or otherwise connected to the outer surface 534 of the fitting 502, and may be configured to engage the top surface 526 of the adapter 504 to form such a substantially fluid-tight seal.

Further, the body 520 of the adapter 504 may also include a central opening (as shown more clearly in FIG. 2) at least partially formed by an inner wall of the body 520. In such examples, the longitudinal axis X of the body 520 may extend substantially centrally through the central fluid passage of the adapter 504 formed by the substantially cylindrical inner wall of the adapter 504. The central opening, inner wall, and central fluid passage of the adapter 504 may be substantially similar to the central opening, inner wall 344, and central fluid passage described above with respect to FIG. 3.

As shown in FIGS. 6a and 6b, an example system 600 or other environment of the present disclosure may include a fitting 602 that is configured to be removably attached to a blood pressure cuff adapter 604 by movement of the fitting 602 in a first direction substantially parallel to the top surface 54 of the cuff 12. In such examples, the fitting 602 may also be configured to be detached from the adapter 604 by moving the fitting 602 in a second direction substantially parallel to the top surface 54 of the cuff opposite the first direction. In example embodiments, any of the structures, functions, and/or other aspects of the various fittings described herein may be included in the fitting 602. Likewise, any of the structures, functions, and/or other aspects of the various adapters described herein may be included in the adapter 604. Further, one or more of the structures, functions, and/or features of the fitting 602, and/or of the adapter 604, may be incorporated into any of the fittings or adapters of the present disclosure.

In the example system 600, various components of the fitting 602 may be substantially similar to corresponding components of, for example, the fitting 402, and various components of the adapter 604 may be substantially similar to corresponding components of, for example, the adapter 404. For example, the fitting 602 may include a substantially rigid body 606, and one or more arms 608a, 608b extending from the body 606. The first and second arms 608a, 608b may also include respective shelves 610a, 610b formed at respective distal ends of the arms 608a, 608b. In the embodiment of FIGS. 6a and 6b, the arms 608a, 608b may be movably connected to the body 606 via a direct connection with the body 606 and/or via one or more posts 612a, 612b or other pieces of material extending substantially laterally from the body 606 to the respective arms 608a, 608b. As can be seen from at least FIG. 6a, the first and second shelves 610a, 610b may extend substantially perpendicularly from the respective arms 608a, 608b. In particular, such first and second shelves 610a, 610b may include one or more surfaces (e.g., a top surface, a bottom surface opposite the top surface, a side surface, etc.), extending substantially perpendicularly from the respective arms 608a, 608b, and such surfaces may be configured to mate with a corresponding surface of the adapter 604 in order to removably attach the fitting 602 to the adapter 604.

At least one of the body 606, posts 612a, 612b, arms 608a, 608b, shelves 610a, 610b, and/or other components of the fitting 602 may be made from any of the materials described above with respect to the body 48. In any such examples, the shape, size, materials, location, and/or other configuration of the posts 612a, 612b may provide for movement of the corresponding arms 608a, 608b and/or shelves 610a, 610b relative to the body 606 when force is applied to respective grips 614a, 614b associated with the arms 608a, 608b. For example, a healthcare practitioner may apply an inward force (e.g., in a direction toward the body 606 of the fitting 602) to one or both of the grips 614a, 614b. The application such an inward force to the grip 614a may cause the arm 608a to pivot about the post 612a, thereby causing the shelf 610a to move laterally away from the body 606 and/or a central longitudinal axis of the fitting 602. Likewise, the application such an inward force to the grip 614b may cause the arm 608b to pivot about the post 612b, thereby causing the shelf 610b to move laterally away from the body 606 and/or a central longitudinal axis of the fitting 602. Such movement of the shelves 610a, 610b may enable the fitting 602 to be removably attached to the blood pressure cuff adapter 604 when the fitting 602 is moved in a first direction of arrow 644 substantially parallel to the top surface 54 of the cuff 12. Similarly, such movement of the shelves 610a, 610b may enable the fitting 602 to be detached from the adapter 604 when the fitting 602 is moved in a second direction of arrow 644 opposite the first direction and substantially parallel to the top surface 54 of the cuff 12.

The fitting 602 may also include one or more extensions, passages, and/or other like channels 616 extending from the body 606. In some examples, the channel 616 may extend substantially along the longitudinal axis of the fitting 602, and the longitudinal axis may extend substantially centrally through the channel 616. The channel 616 may form an opening 618 configured to permit the passage of air or other fluids into the cuff 12 via the fitting 602, and/or to otherwise fluidly connect the fitting 602 with the cuff 12, when the fitting 602 is removably attached to the adapter 604. The fitting 602 may further include a central fluid passage 619 extending at least partially through the body 606. For example, the channel 616 may form at least part of the central fluid passage 619 of the fitting 602, and the longitudinal axis of the fitting 602 may extend substantially centrally through at least part of the central passage 619. In such examples, the opening 618 of the channel 616 may comprise an opening of the central passage 619.

As noted above with respect to the adapter 50 of FIG. 2, the adapter 604 may include a substantially rigid body 620 that is at least partly connected to the cuff 12. For example, the body 620 may include a distal portion 621 extending outwardly from the outer surface 54 of the cuff 12. The body 520 may also include a proximal portion 636 embedded within the cuff 12 and/or extending inwardly from the outer surface 54. In some examples, a top surface of the proximal portion 636 may extend at least partly along and/or may be connected to an inner surface of the cuff 12 disposed opposite the outer surface 54. As shown in FIG. 6b, the body 620 may include a first wall 636 extending substantially parallel to the top surface 54 of the cuff 12 and/or to the top surface of the proximal portion 635. The body 620 may also include a second wall 638 opposite and extending substantially parallel to the first wall 636. In such examples, the body 620 may further include a pair of sidewalls extending from the first wall 636 to the second wall 638, and side surfaces 624a, 624b (e.g., outer surfaces 624am 624b of the body 620) of such sidewalls are illustrated in at least FIG. 6a. Additionally, the body 620 may include a third wall 640 extending substantially perpendicular to the top surface 54 of the cuff 12 and/or to the top surface of the proximal portion 635. The body 620 may also include a fourth wall 642 opposite and extending substantially parallel to the third wall 640. In some examples, the body 620 may further include a pair of sidewalls extending from the third wall 640 to the fourth wall 642.

In any of the examples described herein, the body 620 may also include a first longitudinal axis X extending substantially centrally through a first section of the distal portion 621 formed, at least in part, by the first and second walls 636, 638. For example, the first and second walls 636, 638 may extend substantially parallel to the first longitudinal axis X, and the first and second walls 636, 638 may define at least part of a first central fluid passage 630 of the distal portion 621. The body 620 may also include a second longitudinal axis Y extending substantially centrally through a second section of the distal portion 621 formed, at least in part, by the third and fourth walls 640, 642. For example, the third and fourth walls 640, 642 may extend substantially parallel to the second longitudinal axis Y, and the third and fourth walls 640, 642 may define at least part of a second central fluid passage 631 of the distal portion 621. In such examples, the first longitudinal axis X may extend substantially perpendicular to the second longitudinal axis Y. Further, the first fluid passage 630 of the adapter 620 may be fluidly connected to the second fluid passage 631 of the adapter 620. In such examples, the first longitudinal axis X may extend substantially parallel to the top surface 54 of the cuff 12, and may extend substantially centrally through the first central passage 630. Additionally, the second longitudinal axis Y may extend substantially perpendicular to the top surface 54 of the cuff 12, and may extend substantially centrally through the second central passage 631.

The body 620 of the adapter 604 may be made from any of the materials described above with respect to, for example, the fitting 42. In some examples, the adapter 604 may be made from more than one such material. For example, one or more components or other parts of the distal portion 621 may be made from a first material, and one or more components or other parts of the proximal portion 635 may be made from a second material different from the first material. As noted above with respect to the adapter 50 of FIG. 2, in such examples, the use of such first and second materials may result in the various components or other parts of the body 620 having different rigidities, durabilities, sealing characteristics, and/or other properties.

The distal portion 621 of the adapter 604 may include a ring 622 disposed at an open end of the distal portion 621. In such examples, the ring 622 may form an opening of the first central passage 630, and the ring 622 may be formed, at least in part, by distal ends of the first wall 636, the second wall 638, and the sidewalls extending from the first wall 636 to the second wall 638. The ring 622, and the opening formed thereby, may be shaped, sized, and/or otherwise configured to allow at least part of the channel 616 to pass therethrough when the fitting 602 is removably attached to the adapter 604. In such examples, the channel 616 may pass through the ring 622 and/or the opening, and at least part of the channel 616 may be disposed within the first central passage 630 of the adapter 604 when the fitting 602 is removably attached to the adapter 604. In such examples, the system 600 may also include one or more O-rings, gaskets, and/or other seals 628 configured to form a substantially fluid-tight seal between the fitting 602 and the adapter 604 when the fitting 602 is removably attached to the adapter 604. For example, at least one seal 628 may be attached to, adhered to, embedded substantially within, and/or otherwise connected to either an outer surface 634 of the fitting 602 or to a corresponding distal and/or other outer surface of the ring 622 to facilitate forming such a fluid-tight seal. In the example system 600, at least part (e.g., a base) of the seal 628 may be disposed within a groove formed by the distal and/or other outer surface of the ring 622. In such examples, the seal 628 may engage the outer surface 634 of the fitting 602 proximate a perimeter and/or outer wall of the channel 616 to form a substantially fluid-tight seal with the fitting 602 when the fitting 602 is removably attached to the adapter 604. Alternatively, the seal 628 may be attached to, adhered to, embedded substantially within, and/or otherwise connected to the outer surface 634 of the fitting 602, and may be configured to engage the distal and/or other outer surface of the ring 622 to form such a substantially fluid-tight seal.

The body 620 of the adapter 604 may also include a first ridge 624a formed on the side surface 626a (e.g., the outer surface of the first sidewall extending from the first wall 636 to the second wall 638) of the distal portion 621, and a second ridge 624b formed on the side surface 626b (e.g., the outer surface of the second sidewall extending from the first wall 636 to the second wall 638) of the distal portion 621. The first ridge 624a may be configured to mate with the first shelf 610a of the fitting 602 to assist in retaining the fitting 602 and/or otherwise removably attaching the fitting 602 to the adapter 604. Likewise, the second ridge 624b may be configured to mate with the second shelf 610b of the fitting 602 to assist in retaining the fitting 602 and/or otherwise removably attaching the fitting 602 to the adapter 604. In some examples, at least part of the first ridge 624a may extend substantially perpendicular to the side surface 626a of the body 620, and at least part of the second ridge 624b may extend substantially perpendicular to the side surface 626b of the body 620. As shown in FIG. 6a, at least one of the ridges 624a, 624b may include corresponding camming surfaces 648a, 648b extending at an angle (e.g., an acute angle) from the side surfaces 626a, 626b of the body 620 to ends of the respective ridges 624a, 624b. Such camming surfaces 648a, 648b may be shaped, sized, located, and/or otherwise configured such that at least part of the arms 608a, 608b and/or other components of the fitting 602 may slide along the camming surfaces 648a, 648b as the fitting 602 is removably attached to the adapter 604. For example, in other embodiments such camming surfaces 648a, 648b may be substantially convex, substantially concave, substantially curved, substantially tapered, and/or any other configuration in order to assist in removably attaching the fitting 602 to the adapter 604.

As shown in FIGS. 7a-7e, in some example systems 700 or other embodiments of the present disclosure a fitting 702 and/or a blood pressure cuff adapter 704 may include one or more features or other structural components configured to assist a healthcare practitioner in aligning the fitting 702 with the adapter 704 as the fitting 702 is being removably attached to the adapter 704. In example embodiments, any of the structures, functions, and/or other aspects of the various fittings described herein may be included in the fitting 702. Likewise, any of the structures, functions, and/or other aspects of the various adapters described herein may be included in the adapter 704. Further, one or more of the structures, functions, and/or features of the fitting 702, and/or of the adapter 704, may be incorporated into any of the fittings or adapters of the present disclosure.

In the example system 700, various components of the fitting 702 may be substantially similar to corresponding components of, for example, the fitting 402, and various components of the adapter 704 may be substantially similar to corresponding components of, for example, the adapter 704. For example, the fitting 702 may include a substantially rigid body 706, and one or more arms 708a, 708b extending from the body 706. The first and second arms 708a, 708b may also include respective shelves 710a, 710b formed at respective distal ends of the arms 708a, 708b. In such examples, the arm 708a may be movably connected to the body 706 via a stand 712a extending from the body 706, and the arm 708b may be movably connected to the body 706 via a stand 712b extending from the body 706. As can be seen in at least FIG. 7a, the first and second shelves 710a, 710b may extend substantially perpendicularly from the respective arms 708a, 708b. In particular, such first and second shelves 710a, 710b may include one or more surfaces (e.g., a top surface, a bottom surface opposite the top surface, a side surface, etc.), extending substantially perpendicularly from the respective arms 708a, 708b, and such surfaces may be configured to mate with a corresponding surface of the adapter 704 in order to removably attach the fitting 702 to the adapter 704.

At least one of the body 706, stands 712a, 712b, arms 708a, 708b, shelves 710a, 710b, and/or other components of the fitting 702 may be made from any of the materials described above with respect to the body 48. In any such examples, the shape, size, materials, and/or other configuration of the stands 712a, 712b may provide for movement of the corresponding arms 708a, 708b and/or shelves 710a, 710b relative to the body 706 when force is applied to respective grips 714a, 714b associated with the stands 712a, 712b. Such movement may enable the fitting 702 to be removably attached to the blood pressure cuff adapter 704, and may also enable the fitting 702 to be detached from the adapter 704.

The fitting 702 may also include one or more extensions, passages, and/or other like channels 716 extending from the body 706. In some examples, the channel 716 may extend substantially along the longitudinal axis Z (FIG. 2) of the fitting 702, and the longitudinal axis Z may extend substantially centrally through the channel 716. The channel 716 may form an opening 718 configured to permit the passage of air or other fluids into the cuff 12 via the fitting 702, and/or to otherwise fluidly connect the fitting 702 with the cuff 12, when the fitting 702 is removably attached to the adapter 704. The fitting 702 may further include a central fluid passage 719 extending at least partially through the body 706. For example, the channel 716 may form at least part of the central fluid passage 719 of the fitting 702, and the longitudinal axis Z (FIG. 2) may extend substantially centrally through at least part of the central passage 719. In such examples, the opening 718 of the channel 716 may comprise an opening of the central passage 719.

As noted above with respect to the adapter 50 of FIG. 2, the adapter 704 may include a substantially rigid body 720 that is at least partly connected to the cuff 12. For example, the body 720 may include a distal portion 721 extending outwardly from the outer surface 54 of the cuff 12. The body 720 may also include a proximal portion 719 embedded within the cuff 12 and/or extending inwardly from the outer surface 54. In some examples, a top surface of the proximal portion 719 may extend at least partly along and/or may be connected to an inner surface of the cuff 12 disposed opposite the outer surface 54. The body 720 of the adapter 704 may be made from any of the materials described above with respect to, for example, the fitting 42. In some examples, the adapter 704 may be made from more than one such material. For example, one or more components or other parts of the distal portion 721 may be made from a first material, and one or more components or other parts of the proximal portion 719 may be made from a second material different from the first material. As noted above with respect to the adapter 50 of FIG. 2, in such examples, the use of such first and second materials may result in the various components or other parts of the body 720 having different rigidities, durabilities, sealing characteristics, and/or other properties.

The distal portion 721 of the adapter 704 may include an annular ring 722 having a top surface 726 and a ridge 724 disposed opposite the top surface 726. The ridge 724 may comprise at least part of a bottom surface of the ring 722. In such examples, at least part of the ridge 724 and/or at least another part of the bottom surface of the ring 722 may be configured to mate with the shelves 710a, 710b of the fitting 702 to assist in retaining the fitting 702 and/or otherwise removably attaching the fitting 702 to the adapter 704. In some examples, at least part of the ridge 724 and/or at least another part of the bottom surface of the ring 722 may extend substantially perpendicular to a longitudinal axis X of the body 720. Additionally, the adapter 704 may include a substantially cylindrical sidewall extending from the ridge 724 to the top surface of the proximal portion 719. Such a sidewall may space the ridge 724 from the top surface of the proximal portion 719 such that the shelves 710a, 710b of the fitting 702 may have room to mate with the ridge 724 beneath the ring 722.

The top surface 726 of the ring 722 may be substantially convex, substantially concave, substantially curved, substantially tapered, and/or any other configuration in order to assist in removably attaching the fitting 702 to the adapter 704. In some examples, the top surface 726 of the ring 722 may comprise a convex surface extending radially away from the longitudinal axis X of the body 720 from a distal end 730 of the top surface 726 to a proximal end 732 of the top surface 726. In such examples, the curved top surface 726 may comprise a camming surface along which at least part of the arms 708a, 708b and/or other components of the fitting 702 may slide as the fitting 702 is removably attached to the adapter 704.

In example embodiments, the ring 722 may also include a groove 728 extending at least partly (and, in some examples, completely) around the longitudinal axis X, and being shaped, sized, located, and/or otherwise configured to accept a member 734 and/or other structural feature of the adapter 702. As shown in at least FIG. 7a, such a member 734 may extend (e.g., substantially perpendicularly) from an outer surface 736 of the fitting 702 disposed opposite and/or facing the top surface 726 when the fitting 702 is removably attached to the adapter 704. The member 734 may comprise a shaft, pin, rod, rib, ring, flange, detent, and/or other extension of the body 706, and the member 734 may be useful in laterally and/or otherwise aligning the fitting 702 with the adapter 704 when removably attaching the fitting 702 to the adapter 704. For example, the groove 728 and the member 734 may be positioned and/or otherwise configured such that disposing at least part of the member 734 within the groove 728 when removably attaching the fitting 702 to the adapter 704 may cause the longitudinal axis Z of the fitting 702 (FIG. 2) to be collinear with the longitudinal axis X of the adapter 704. The member 734 may be substantially cylindrical, substantially cube-shaped, substantially V-shaped, substantially arcuate, substantially annular, and/or any other shape to assist in aligning the fitting 702 with the adapter 704. Additionally, in any of the example embodiments described herein the member 734 may be shaped, sized, dimensioned, located, and/or otherwise configured to minimize and/or substantially eliminate lateral movement of the fitting 702 relative to the adapter 704 when the fitting 702 is removably attached to the adapter 704. In any such examples, the member 734 may be shaped, sized, dimensioned, located, and/or otherwise configured to provide additional rigidity, support, and/or stability to the removable connection between the fitting 702 and the adapter 704. Further, in any of the example embodiments described herein having a member and a groove, the member (e.g., the member 734) may alternatively comprise an extension and/or other component of the adapter (e.g., the adapter 704), and in such embodiments the groove (e.g., the groove 728) may be formed by and/or may comprise a component of the fitting (e.g., the fitting 702). Additionally, in any of the embodiments described herein having a member and a groove, the member (e.g., the member 734) may comprise a plurality of members (e.g., a plurality of arcuate segments, etc.) spaced substantially circumferentially about, for example, the longitudinal axis Z (FIG. 2) of the fitting 702. Further, while FIG. 7a illustrates the groove 728 being disposed on and/or formed by the top surface 726, in other examples, the groove 728 may be disposed on, disposed proximate, and/or formed by a radially outermost portion of the ring 722.

In any of the embodiments herein, a first component of the fitting 702 may be configured to mechanically interlock with (e.g., a snap-fit, a friction fit, a meshing, and/or any other type of interlock) a corresponding second component of the adapter 704. For example, in some embodiments a component of the member 734 may form a snap-fit and/or other interlocking fit with the groove 728 of the adapter 704. In other embodiments, at least part of the channel 716 may interlock with at least part of the portion 719 of the adapter 704 when the fitting 702 is removably attached to the adapter 704.

The system 700 may also include one or more O-rings, gaskets, and/or other seals 737 configured to form a substantially fluid-tight seal between the fitting 702 and the adapter 704 when the fitting 702 is removably attached to the adapter 704. For example, at least one seal 737 may be attached to, adhered to, embedded substantially within, disposed adjacent to, and/or otherwise connected to a substantially cylindrical inner wall 738 of the adapter 704 to facilitate forming such a fluid-tight seal. In such examples, the seal 737 may engage an outer wall 740 of the channel 716 (e.g., an outer surface of the outer wall 740) to form a substantially fluid-tight seal with the fitting 702 when the fitting 702 is removably attached to the adapter 704.

Figure 7A:
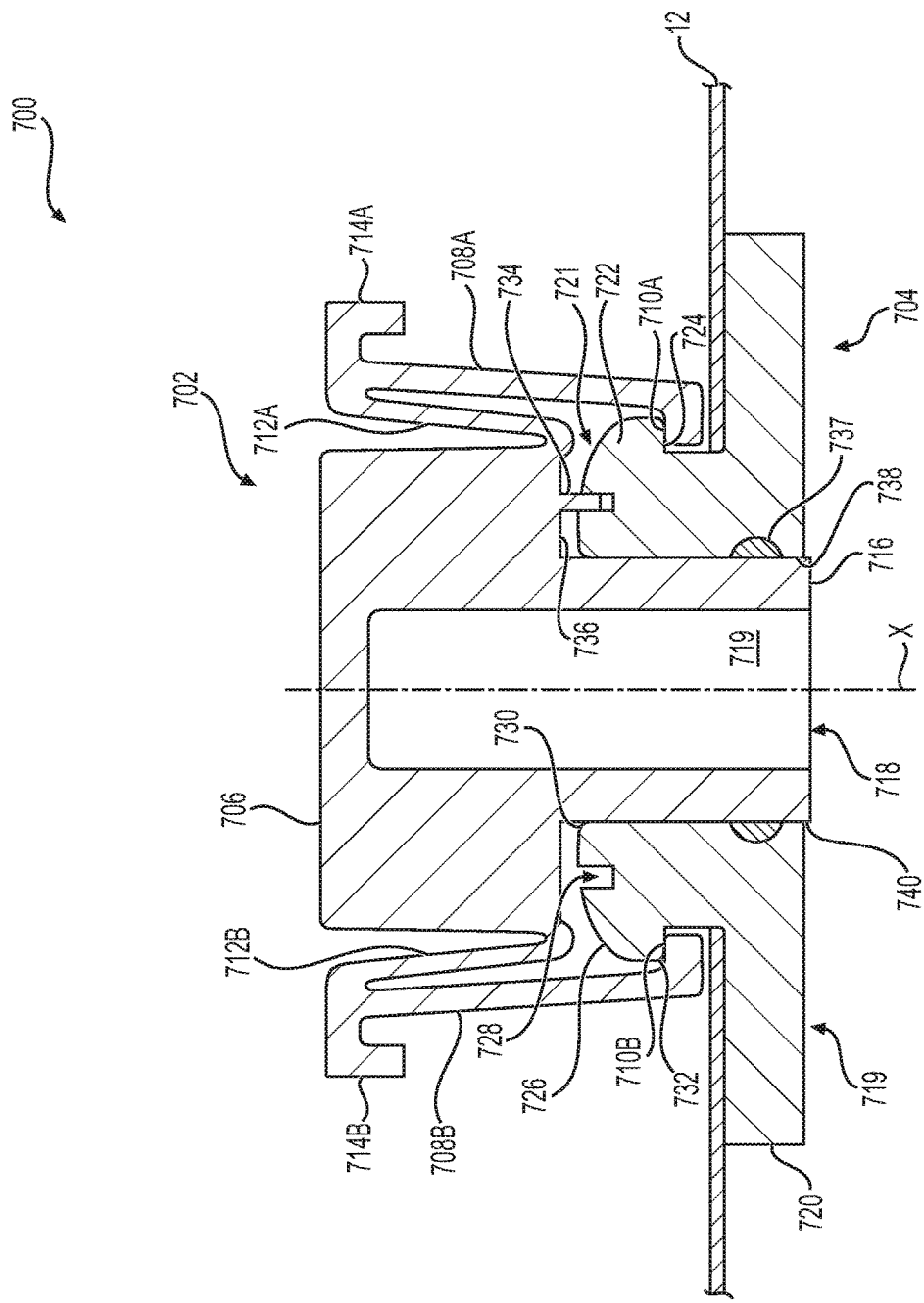
FIG. 7a is cross-sectional view of another example blood pressure cuff adapter and an example fitting removably attached to the adapter.

As shown in at least FIG. 7b, the adapter 704 may also include a central opening 742 at least partially formed by a surface of the inner wall 738. In such examples, the longitudinal axis X (FIG. 7a) of the body 720 may extend substantially centrally through a central fluid passage of the adapter 704 formed by the substantially cylindrical inner wall 738. The central opening 742, inner wall 738, and central fluid passage of the adapter 704 may be substantially similar to the central opening, inner wall 344, and central fluid passage described above with respect to FIG. 3. Further, as shown in the top view of FIG. 7b, in some examples the groove 728 may be disposed on the top surface 726 between (e.g., substantially centrally between) the proximal end 732 and the distal end 730 of the top surface 726. Additionally, in some examples the groove 728 may include at least one detent 744 configured to contact the member 734 when the fitting 702 is removably attached to the adapter 704. It is understood that in at least the systems described herein with respect to FIGS. 1-5, 7a-7e, and 10, the fitting may be rotatable about the longitudinal axis X of the adapter 704 in the clockwise direction of arrow 746 and in the counter clockwise direction of arrow 748. In such examples, the one or more detents 744 disposed within the groove 728 may be shaped, sized, located, and/or otherwise configured to contact the member 734 as the fitting 702 is rotated about the longitudinal axis X of the adapter 704. The one or more detents 744 may be substantially dome-shaped, substantially ramp-shaped, and/or any other shape to assist in at least partially restricting rotation of the fitting 702 about the longitudinal axis X of the adapter 704 when the member 734 contacts the one or more detents 744.

As shown in at least FIG. 7c, in some examples the groove 728 may include at least one wall 750 extending substantially parallel to the longitudinal axis X. In such examples, the wall 750 may prohibit 360 degree rotation of the fitting 702 about the longitudinal axis X of the adapter 704 when the fitting 704 is removably attached to the adapter 702. For example, the wall 750 may block rotation of the fitting 702 about the longitudinal axis X of the adapter 704 when the member 734 contacts the wall 750. Although the example embodiment of FIG. 7c illustrates a single wall 750 disposed within the groove 728, in further examples, two or more walls 750 may be disposed the groove 728. In any of the examples described herein, the one or more walls 750 may have a width and/or a height substantially equal to a corresponding width and/or height of the groove 728.

Figure 7D:
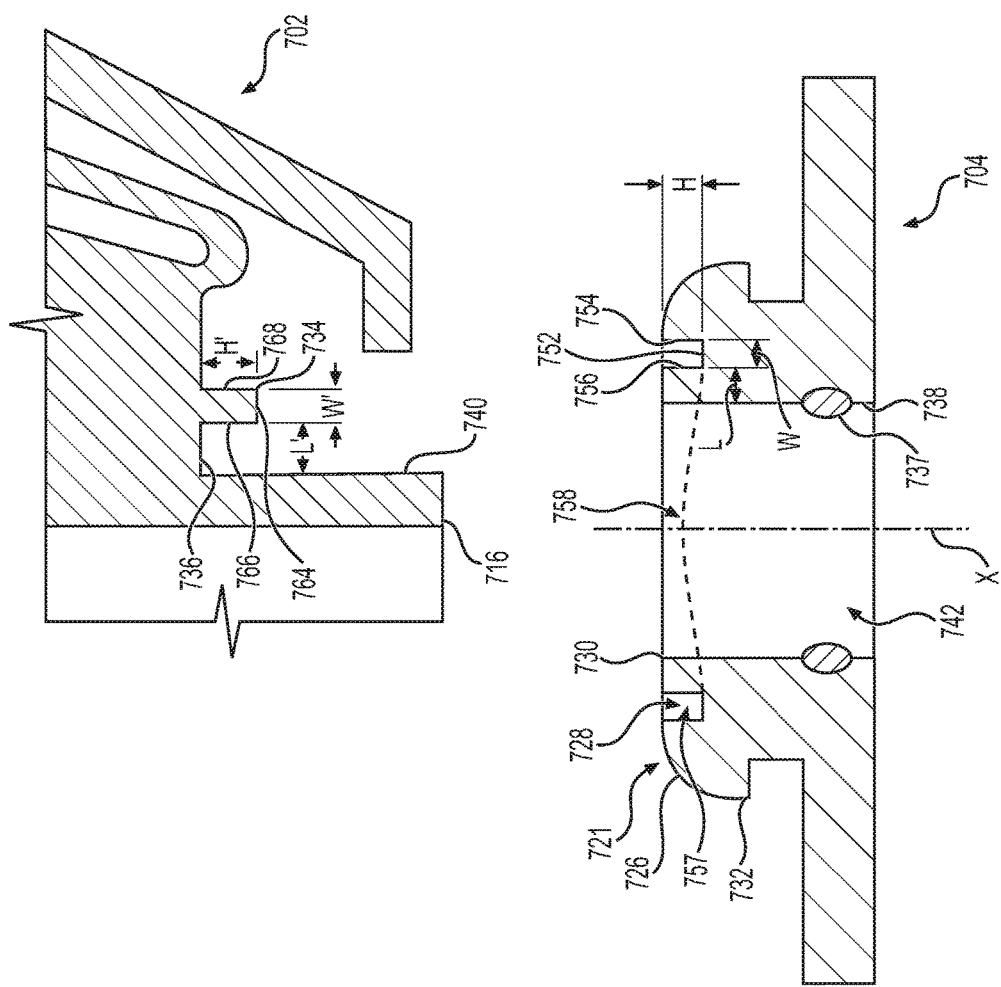
FIG. 7d is a cross-sectional view of an example blood pressure cuff adapter and a partial cross-sectional view of an example fitting.

The cross-sectional view of FIG. 7d illustrates portions of the fitting 702 and the adapter 704 in more detail. For example, as noted above, the groove 728 may have any desired width W and/or height H in order to accommodate the member 734. For example, the groove 728 may include a base 752, a first sidewall 754 extending substantially perpendicularly from the base 752, and a second sidewall 756 opposite the first sidewall 754 and extending substantially perpendicularly from the base 752. In such examples, the first and second sidewalls 754, 756 may extend from the base 752 to the top surface 726, and the height H of the groove 728 may comprise either a height H of the first sidewall 754 or a height H of the second sidewall 756. In any of the examples described herein, one or more of the detents 744 described above may be disposed on the base 752, the first sidewall 754, or the second sidewall 756.

In some examples, the height H of the groove 728 may be substantially constant. In other examples, on the other hand, the groove 728 may have a variable height H along at least a portion of the groove 728. For example, as shown in FIG. 7d the base 752 of the groove 728 may have at least one trough 757 and at least one peak 758. In such examples, the trough 757 may comprise a first portion of the groove 728 having the largest height H, and the peak 758 may comprise a second portion of the groove 728 having the smallest height H. For instance, in such examples the peak 758 formed by the base 752 may be disposed axially closer to the top surface 726 of the ring 722 than the trough 757 formed by the base 752. In such examples, the variability in the height H of the groove 728 (e.g., the decrease in height H from the trough 757 to the peak 758) may assist the user in detaching the fitting 702 from the adapter 704. For example, the member 734 may slidably engage and/or otherwise move substantially along the base 752 as the fitting 702 is rotated about the longitudinal axis X of the adapter 704. In such examples, engagement between the member 734 and the base 752 as the member 734 moves from a first location proximate the trough 757 to a second location proximate the peak 758 may assist in moving the fitting 702 in an upward direction away from the adapter 704. Such movement may assist a healthcare practitioner in detaching the fitting 702 from the adapter 704.

In such examples, the member 734 may also be shaped, sized, and/or otherwise configured to assist a healthcare practitioner in detaching the fitting 702 from the adapter 704. For example, the member 734 may include a base 764, a first sidewall 766 extending substantially perpendicularly from the base 764, and a second sidewall 768 opposite the first sidewall 766 and extending substantially perpendicularly from the base 764. In such examples, the first and second sidewalls 766, 768 may extend from the base 764 to the outer surface 736. The member 734 may also have a height H' substantially equal to the height H of the groove 728, and a width W' substantially equal to the width W of the groove 728. It is understood that in some examples, the height H' may be marginally less than the height H, and the width W' may be marginally less than the width W to minimize and/or substantially eliminate friction and/or resistance caused by the member 734 contacting one or both of the sidewalls 754, 756. Further, the sidewall 756 of the groove 728 may be disposed a distance L from the inner wall 738, and the sidewall 766 may be disposed a distance L' from the outer wall 740 of the channel 716 substantially equal to the distance L.

As shown in FIG. 7e, in further examples, the fitting 702 may include one or more sensors configured to determine a distance between at least part of the fitting 702 and a corresponding part of the adapter 704. Additionally or alternatively, in some examples the one or more sensors may be configured to read information from a corresponding component of the adapter 704 and/or otherwise assist in identifying the adapter 704. For example, the fitting 702 may include a capacitance sensor, a proximity sensor, a light sensor, RFID sensor, a barcode reader, and/or any other sensor 762 connected thereto. In some examples, the sensor 762 may be disposed on, embedded substantially within, and/or otherwise connected to the member 734, such as at a distal end of the member 734. In such examples, the fitting 704 may include a corresponding conductor, layer of reflective paint or ink, RFID tag, barcode, and/or other feature 760. In such examples, the feature 760 may be disposed anywhere on and/or within the adapter 704 such that the feature 760 is located at least partly within a field of view of the sensor 762 when the fitting 702 is removably attached to the adapter 704. For example, in embodiments in which the sensor 762 is disposed on embedded substantially within, and/or otherwise connected to the member 734, such as at a distal end of the member 734, the feature 760 may be disposed on embedded substantially within, and/or otherwise connected to the base 752 of the groove 728 or at least one of the sidewalls 754, 756. Further, although FIG. 7e illustrates the sensor 762 being connected to the fitting 702 and the feature 760 being connected to the adapter 704, in other examples, this configuration may be reversed such that the sensor 762 is connected to the adapter 704 and the feature 760 is connected to the fitting 702.

In any of the examples described herein, the sensor 762 may be operably connected to and/or otherwise in communication with the controller 20 described above. For example, the sensor 762 may be configured to determine, among other things, a distance between (e.g., a proximity) the distal end of the member 734 and the base 752 of the groove 728. In such examples, various cuffs 12 may include adapters 704 having grooves 728 of respective known heights H based on a desired application, desired intended use (e.g., child, adult, bariatric patient, elderly patient, etc.), and/or desired fitting 702 with which the particular cuff 12 should be used. For example, a cuff 12 manufactured by an example first manufacturer may be tuned and/or otherwise designed to be used with fittings 702 manufactured by the same first manufacturer. Accordingly, the groove 728 of an adapter 704 connected to such an example cuff 12 may have a known height H that is saved in the memory 24 associated with the controller 20. In examples in which a corresponding fitting 702 manufactured by the same first manufacturer is removably attached to the adapter 704, the sensor 762 may determine such a known height H and/or a corresponding known distance between (e.g., a proximity) the distal end of the member 734 and the base 752 of the groove 728, and may send a signal including such information to the controller 20. Upon receipt of the signal, the controller 20 may compare such information to one or more known values corresponding to approved fittings 702 manufactured by the first manufacturer, and the controller 20 may identify a match based on such a comparison. In response, the controller 20 may cause a flow control device 770 operably connected to the controller 20 to inflate and/or deflate the cuff 12 according to standard operating flow rates and/or cuff pressures.

On the other hand, in examples in which a fitting 702 manufactured by a second manufacturer (different from the first manufacturer of the cuff 12) is removably attached to the adapter 704, the sensor 762 may determine a different height H and/or a different distance between the distal end of the member 734 and the base 752 of the groove 728. The sensor 762 may send a signal including such information to the controller 20, and the controller 20 may compare such information to one or more known values corresponding to approved fittings 702 manufactured by the first manufacturer, and the controller 20 may determine that no match exists based on such a comparison. In response, the controller 20 may prohibit the flow control device 770 from inflating the cuff 12 or may cause the flow control device 770 to inflate and/or deflate the cuff 12 with significantly reduced (e.g., undesirably low) operating flow rates and/or cuff pressures. In this way, the sensor 762 and the feature 760 illustrated in.

FIG. 7e may be useful in preventing the use of fittings 702 that do not match or correspond with a cuff having a particular adapter 704. In such examples the sensor 762 and the feature 760 illustrated in FIG. 7e may also be useful in preventing the use of cuffs 12 having adapters 704 that do not match or correspond with the particular fittings 702.

In the same way, the height H described above, the width and/or inner diameter of the groove 728, an outer diameter of the adapter 704, and/or any other characteristics of the cuff 12 may be read, sensed, and/or otherwise determined by the sensor 762, and such characteristics may be used to determine whether an age appropriate cuff 12 is being used. As noted above, in some examples the sensor 762 may comprise an RFID reader, and in such examples, such characteristics may be read by the sensor 762 reading a corresponding RFID tag or other feature 760 disposed within the groove 728. For example, in situations in which an adult cuff is being used on an adolescent or child patient, the controller 20 may determine (based on one or more signals from the sensor 762) that an age inappropriate cuff 12 is currently being used. Such signals may indicate that, for example, a sensed height H, width, and/or inner diameter of the groove 728 does not match a known height H, width, and/or inner diameter of a groove corresponding to an acceptable cuff (e.g., an adolescent cuff) for the particular patient. In response, the controller 20 may prohibit the flow control device 770 from inflating the cuff 12 or may cause the flow control device 770 to inflate and/or deflate the cuff 12 with significantly reduced (e.g., undesirably low) operating flow rates and/or cuff pressures. It is also understood that the location of the groove 728 (e.g., the radial distance between the longitudinal axis X and one or more sidewalls of the groove 728) may also be sensed by the sensor 762 in a similar manner, and such a location may also be used to determine whether the cuff 12 was manufactured by such a first manufacturer and/or whether the cuff 12 is appropriate for the age, demographics, or other characteristics of the patient.

In any of the examples described herein, the fitting 702 and/or the adapter 704 may be made, at least in part, from a substantially transparent or substantially translucent urethane or other such polymer. For example, the fitting 702 may be made from a substantially translucent urethane, and may include one or more light-emitting diodes (LEDs) or other light sources operably connected to the controller 20. In such examples, the sensor 762 may be configured to determine whether a particular adapter 704 of a cuff matches or corresponds with a particular fitting 702. If such an appropriate match is found, the one or more LEDs may be controlled by the controller 20 to generate a first visual response (e.g., lighting up green or some other color) indicative of the match. If such an appropriate match is not found, the one or more LEDs may be controlled by the controller 20 to generate a second visual response (e.g., lighting up red or some other color) indicative that such a match was not found.

Further, in some examples the sensor 762 and/or one or more additional sensors operably connected to the adapter 704, the cuff 12, and/or the fitting 702 may be configured to determine an inflation pressure of the cuff 21, whether a leak is occurring, and/or other similar information. In any of the examples described herein, such sensors may provide one or more signals to the controller 20 indicating such information, and the controller 20 may control the one or more LEDs to provide a visual response (e.g., blink, remain on, illuminate a desired color, etc.) based at least in part on such information. For example, the one or more LEDs may be used to indicate that the cuff 12 has been inflated to a pressure above a minimum pressure threshold, that the cuff 12 has been inflated to a pressure above a maximum pressure threshold, that the cuff 12 has a leak, that the cuff 12 has been left unattended for longer than a maximum time threshold, that an improper cuff 12 is being used, and/or other conditions.

In examples in which the controller 20 determines, based at least in part on such signals from the one or more sensors, that the cuff 12 has been inflated to an inflation pressure above a maximum threshold, the controller 20 may control a valve (e.g., a poppet valve, solenoid valve, etc.) fluidly connected to the cuff 12 to at least partly open in order to decrease the inflation pressure of the cuff. In alternative embodiments, the controller 12 may control the flow control device 770 to reduce the inflation pressure of the cuff 12 to a desired level.

As shown in FIGS. 7f and 7g, in still further examples at least part of the ring 722 may be configured to mate with at least a portion of the member 734 to assist in, among other things, stabilizing the removable connection between the fitting 702 and the adapter 704. For example, as shown in FIG. 7f a radially inner portion of the ring 722 may be removed to form a groove 728. In such examples, the groove 728 may include a base 752 having a length L and extending substantially perpendicularly from the inner wall 738 of the adapter 704. In particular, the base 752 may extend radially outwardly from the inner wall 738. The groove 728 may also include a radially outermost sidewall 754 extending substantially perpendicularly from the base 752. For example, the sidewall 754 may extend axially from the base 752 to the top surface 726 of the ring 722. In such examples, the sidewall 754 may mate with and/or otherwise at least partially engage a radially outermost surface of the member 734 when the fitting 702 is removably attached to the adapter 704. Such engagement between the sidewall 754 and the radially outermost surface of the member 734 may assist in minimizing and/or substantially eliminating lateral movement of the fitting 702 relative to the adapter 704 when the fitting 702 is removably attached to the adapter 704.

Alternatively, as shown in FIG. 7g a radially outer portion of the ring 722 may be removed. In such examples, a groove formed in the ring 722 may include a base 752 extending substantially perpendicularly relative to the inner wall 738 of the adapter 704. Such a groove may also include a radially innermost sidewall 756 extending substantially perpendicularly from the base 752. For example, the sidewall 756 may extend axially from the base 752 to the top surface 726 of the ring 722, and the sidewall 756 may be disposed a radial distance L from the inner wall 738. In such examples, the sidewall 756 may mate with and/or otherwise at least partially engage a radially innermost surface of the member 734 when the fitting 702 is removably attached to the adapter 704. Such engagement between the sidewall 756 and the radially innermost surface of the member 734 may assist in minimizing and/or substantially eliminating lateral movement of the fitting 702 relative to the adapter 704 when the fitting 702 is removably attached to the adapter 704.

In still further examples, at least part of the adapter may be rotatable relative to the cuff 12. In some examples, such rotation may be about a rotational axis that extends substantially perpendicular to the top surface 54 of the cuff. Additionally or alternatively, such rotation may be about a rotational axis that extends substantially parallel to the top surface 54 of the cuff. For example, as shown in FIGS. 8a and 8b, an example system 800 or other environment of the present disclosure may include a fitting 802 that is configured to be removably attached to a blood pressure cuff adapter 804 by movement of the fitting 802 in a first direction substantially parallel to the top surface 54 of the cuff 12. In such examples, the fitting 802 may also be configured to be detached from the adapter 804 by moving the fitting 802 in a second direction substantially parallel to the top surface 54 of the cuff opposite the first direction. As will be described below, such an adapter 804 may include one or more hinges configured to facilitate rotation of at least part of the adapter 804, relative to the cuff 12, while the fitting is removably attached to the adapter 804. In example embodiments, any of the structures, functions, and/or other aspects of the various fittings described herein may be included in the fitting 802. Likewise, any of the structures, functions, and/or other aspects of the various adapters described herein may be included in the adapter 804. Further, one or more of the structures, functions, and/or features of the fitting 802, and/or of the adapter 804, may be incorporated into any of the fittings or adapters of the present disclosure.

In the example system 800, various components of the fitting 802 may be substantially similar to corresponding components of, for example, the fitting 602, and various components of the adapter 804 may be substantially similar to corresponding components of, for example, the adapter 604. For example, the fitting 802 may include a substantially rigid body 806, and one or more arms 808a, 808b extending from the body 806. The first and second arms 808a, 808b may also include respective shelves 810a, 810b formed at respective distal ends of the arms 808a, 808b. In the embodiment of FIGS. 8a and 8b, the arms 808a, 808b may be movably connected to the body 806 via a direct connection with the body 806 and/or via one or more posts (not shown) or other pieces of material extending substantially laterally from the body 806 to the respective arms 808a, 808b. As can be seen from at least FIG. 8a, the first and second shelves 810a, 810b may extend substantially perpendicularly from the respective arms 808a, 808b. In particular, such first and second shelves 810a, 810b may include one or more surfaces (e.g., a top surface, a bottom surface opposite the top surface, a side surface, etc.), extending substantially perpendicularly from the respective arms 808a, 808b, and such surfaces may be configured to mate with a corresponding surface of the adapter 804 in order to removably attach the fitting 802 to the adapter 804.

At least one of the body 806, arms 808a, 808b, shelves 810a, 810b, and/or other components of the fitting 802 may be made from any of the materials described above with respect to the body 48. In any such examples, the arms 808a, 808b and/or shelves 810a, 810b may be moveable relative to the body 806 when force is applied to respective grips 814a, 814b associated with the arms 808a, 808b. For example, a healthcare practitioner may apply an inward force (e.g., in a direction toward the body 806 of the fitting 802) to one or both of the grips 814a, 814b. The application such an inward force to the grip 814a may cause the arm 808a to pivot relative to, for example, a first sidewall of the fitting 802, thereby causing the shelf 810a to move laterally away from the body 806 and/or a central longitudinal axis of the fitting 802. Likewise, the application such an inward force to the grip 814b may cause the arm 608b to pivot relative to, for example, a second sidewall of the fitting 802 opposite the first sidewall, thereby causing the shelf 810b to move laterally away from the body 806 and/or a central longitudinal axis of the fitting 802. Such movement of the shelves 810a, 810b may enable the fitting 802 to be removably attached to the blood pressure cuff adapter 804 when the fitting 802 is moved in a first direction of arrow 842 substantially parallel to the top surface 54 of the cuff 12. Similarly, such movement of the shelves 810a, 810b may enable the fitting 802 to be detached from the adapter 804 when the fitting 802 is moved in a second direction of arrow 844 opposite the first direction and substantially parallel to the top surface 54 of the cuff 12.

The fitting 802 may also include one or more extensions, passages, and/or other like channels 816 extending from the body 806. In some examples, the channel 816 may extend substantially along the longitudinal axis of the fitting 802, and the longitudinal axis may extend substantially centrally through the channel 816. The channel 816 may form an opening 818 configured to permit the passage of air or other fluids into the cuff 12 via the fitting 802, and/or to otherwise fluidly connect the fitting 802 with the cuff 12, when the fitting 802 is removably attached to the adapter 804. The fitting 802 may further include a central fluid passage 819 extending at least partially through the body 806. For example, the channel 816 may form at least part of the central fluid passage 819 of the fitting 802, and the longitudinal axis of the fitting 802 may extend substantially centrally through at least part of the central passage 819. In such examples, the opening 818 of the channel 816 may comprise an opening of the central passage 819.

As noted above with respect to the adapter 50 of FIG. 2, the adapter 804 may include a substantially rigid body 820 that is at least partly connected to the cuff 12. For example, the body 820 may include a distal portion 821 extending outwardly from the outer surface 54 of the cuff 12. The body 820 may also include a proximal portion 836 embedded within the cuff 12 and/or extending inwardly from the outer surface 54. In some examples, a top surface of the proximal portion 836 may extend at least partly along and/or may be connected to an inner surface of the cuff 12 disposed opposite the outer surface 54. As shown in FIG. 8b, the body 820 may include a hinge 825 rotatably connecting the distal portion 821 to the proximal portion 836. In particular, the hinge 825 may enable the distal portion 821 to be rotated about a rotational axis R of the hinge 825 and relative to the proximal portion 836. In such examples, the distal portion 821 may include a central longitudinal axis X and the proximal portion 836 may include a central longitudinal axis Y extending substantially perpendicular to, and coplanar with, the longitudinal axis X. In such examples, the rotational axis R may extend substantially perpendicular to the plane in which the axes X and Y are disposed. For example the hinge 825 may enable the distal portion 821 to rotate, about the rotational axis R, in the clockwise direction of arrow 838 and in the counterclockwise direction of arrow 840.

In any of the examples described herein, the longitudinal axis X may extend substantially centrally through a section of the distal portion 821 formed, at least in part, by first, second, third, and fourth walls 846, 848, 850, 852 of the distal portion 821. For example, the first wall 846 may extend substantially parallel to the second wall 848, and the third wall 850 may extend substantially parallel to the fourth wall 852. Together, the first, second, third, and fourth walls 846, 848, 850, 852 may define at least part of a first central fluid passage 831 of the distal portion 821. The proximal portion 836 may also include one or more walls similar to the first, second, third, and fourth walls 846, 848, 850, 852 (e.g., a substantially cylindrical wall 854), and the longitudinal axis Y may extend substantially centrally through a section of the proximal portion 836 formed, at least in part, by the one or more walls of the proximal portion 836. For example, the one or more walls of the proximal portion 836 may define at least part of a central fluid passage 830 of the proximal portion 836. In such examples, the fluid passage 831 of the distal portion 821 may be fluidly connected to the fluid passage 830 of the proximal portion 836 via, for example, a central fluid passage 829 of the hinge 225. In such examples, the first longitudinal axis X may extend substantially parallel to the top surface 54 of the cuff 12, and may extend substantially centrally through the central passage 831. Additionally, the longitudinal axis Y may extend substantially perpendicular to the top surface 54 of the cuff 12, and may extend substantially centrally through the central passage 830.

The body 820 of the adapter 804 may be made from any of the materials described above with respect to, for example, the fitting 42. In some examples, the adapter 804 may be made from more than one such material. For example, one or more components or other parts of the distal portion 821 may be made from a first material, and one or more components or other parts of the proximal portion 836 may be made from a second material different from the first material. As noted above with respect to the adapter 50 of FIG. 2, in such examples, the use of such first and second materials may result in the various components or other parts of the body 820 having different rigidities, durabilities, sealing characteristics, and/or other properties.

The distal portion 821 of the adapter 804 may include a ring 822 disposed at an open end of the distal portion 821. In such examples, the ring 822 may form an opening 823 of the central passage 831, and the ring 822 may be formed, at least in part, by distal ends of the first, second, third, and fourth walls 846, 848, 850, 852. The ring 822, and the opening 823 formed thereby, may be shaped, sized, and/or otherwise configured to allow at least part of the channel 816 to pass therethrough when the fitting 802 is removably attached to the adapter 804. In such examples, the channel 816 may pass through the ring 822 and/or the opening 823, and at least part of the channel 816 may be disposed within the central passage 831 of the adapter 804 when the fitting 802 is removably attached to the adapter 804. In such examples, the system 800 may also include one or more O-rings, gaskets, and/or other seals 828 configured to form a substantially fluid-tight seal between the fitting 802 and the adapter 804 when the fitting 802 is removably attached to the adapter 804. For example, at least one seal 828 may be attached to, adhered to, embedded substantially within, and/or otherwise connected to either an outer surface 834 of the fitting 802 or to a corresponding distal and/or other outer surface of the ring 822 to facilitate forming such a fluid-tight seal. In the example system 800, the seal 828 may be connected to the ring 828, and the seal 628 may engage the outer surface 834 of the fitting 802 proximate a perimeter and/or outer wall of the channel 816 to form a substantially fluid-tight seal with the fitting 802 when the fitting 802 is removably attached to the adapter 804. Alternatively, the seal 828 may be attached to, adhered to, embedded substantially within, and/or otherwise connected to the outer surface 834 of the fitting 802, and may be configured to engage the distal and/or other outer surface of the ring 822 to form such a substantially fluid-tight seal.

The body 820 of the adapter 804 may also include a first ridge 824a formed on an inner surface 826 of the wall 852, and within the central passage 831. The body 820 may also include a second ridge 824b formed on an inner surface of the wall 850 opposite the inner surface 826, and within the central passage 831. The first ridge 824a may be configured to mate with the first shelf 810a of the fitting 802, when the arm 808a and/or the first shelf 810a are disposed at least partly within the central passage 831, to assist in retaining the fitting 802 and/or otherwise removably attaching the fitting 802 to the adapter 804. Likewise, the second ridge 824b may be configured to mate with the second shelf 810b of the fitting 802, when the arm 808b and/or the second shelf 810b are disposed at least partly within the central passage 831, to assist in retaining the fitting 802 and/or otherwise removably attaching the fitting 802 to the adapter 804. In some examples, at least part of the first ridge 824a may extend substantially perpendicular to the inner surface 826 of the wall 852, and at least part of the second ridge 824b may extend substantially perpendicular to the inner surface of the wall 850 opposite the inner surface 826. As shown in FIG. 8a, at least one of the ridges 824a, 824b may include corresponding camming surfaces extending at an angle (e.g., an acute angle) from the inner surfaces of the walls 850, 852 to ends of the respective ridges 824a, 824b. Such camming surfaces may be shaped, sized, located, and/or otherwise configured such that at least part of the arms 808a, 808b and/or other components of the fitting 802 may slide along the camming surfaces as the fitting 802 is removably attached to the adapter 804. For example, in other embodiments such camming surfaces may be substantially convex, substantially concave, substantially curved, substantially tapered, and/or any other configuration in order to assist in removably attaching the fitting 802 to the adapter 804.

Figure 9:
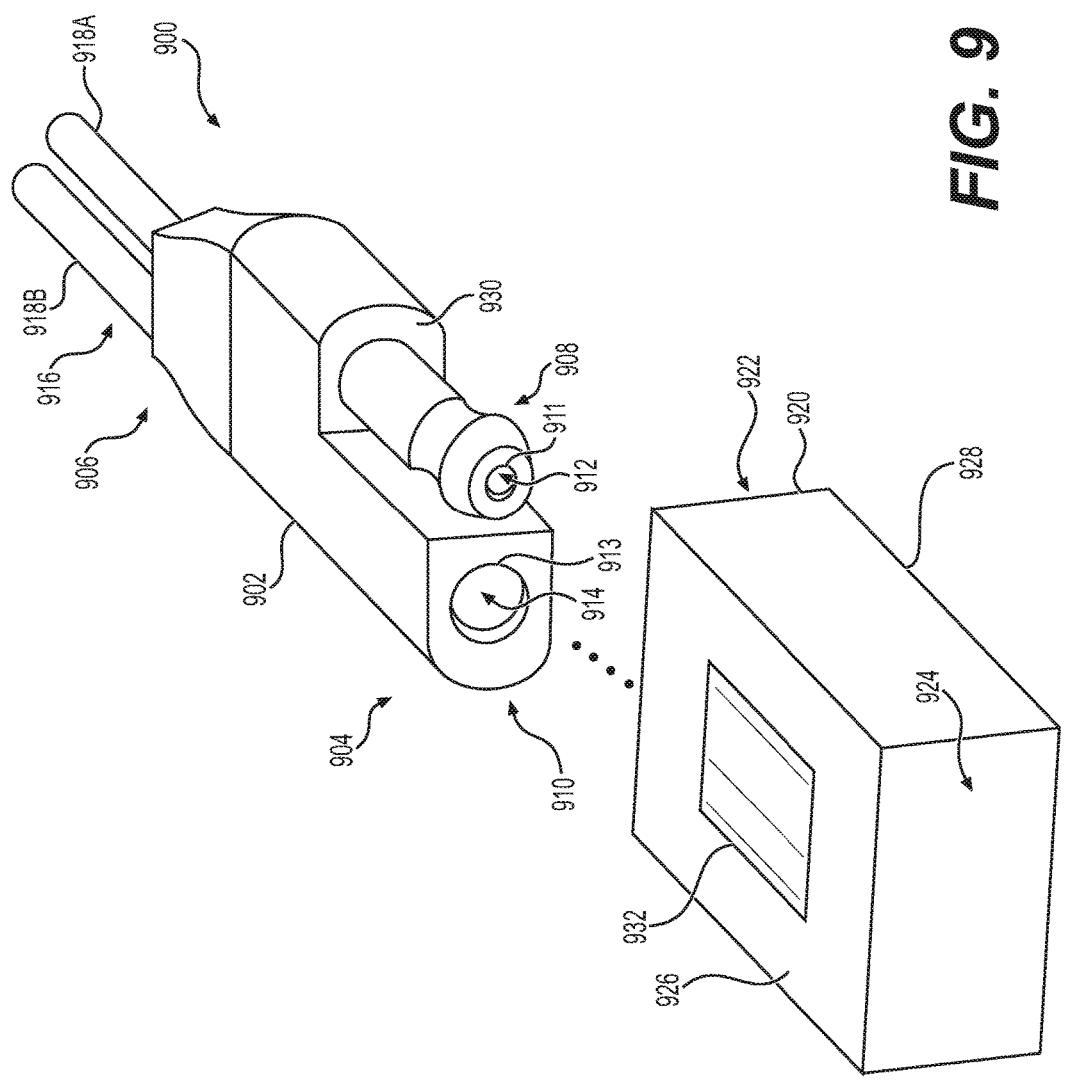
FIG. 9 is an isometric view of still another example blood pressure cuff adapter and an example fitting.

FIG. 9 illustrates still another example system 900 of the present disclosure including a fitting 902 configured to facilitate transmission of pressurized air or other fluids to an adapter 920 fluidly connected to a blood pressure cuff 12. The fitting 902 may include a distal end 904 configured to mate with the adapter 920, and a proximal end 906 opposite the distal end 904. The distal end 904 may include one or more shafts 908, 910 configured to be inserted, at least in part, into corresponding openings formed by a distal end 922 of the adapter 920. For example, the first shaft 908 may comprise a barb-like connector or any other such fluid connector extending from an outer wall 930 of the fitting 902. The first shaft 908 may include a distal opening 911, and the opening 911 may comprise a distal opening of a central fluid passage 912 of the first shaft 908. Similarly, the second shaft 910 may include a distal opening 913, and the opening 913 may comprise a distal opening of a central fluid passage 914 of the second shaft 910. In such examples, one or more sections of tubing 916 may be connected to the fitting 902 at the proximal end 906. For example, tubing 916 having first and second separate conduit sections 918a, 918b may be fluidly connected to the fitting 902 at the proximal end 906. The fitting 902 may comprise separate respective fluid passages configured to transfer fluid received from the separate conduit sections 918a, 918b to the cuff 12 and/or to the adapter 920.

In such examples, the adapter 920 may include a distal end 922 and a proximal end 924 opposite the distal end 922. The fitting 902 may be removably attached to the adapter 920 by inserting at least part of the distal end 904 into corresponding opening(s) formed by the distal end 922 of the adapter 920. For example, in some embodiments the adapter 920 may include a female port or other like opening (not shown) at the distal end 922 configured to accept and/or otherwise mate with the male first shaft 908. Additionally, in such embodiments the adapter 920 may include a male shaft or other like member (not shown) at the distal end 922 configured to extend into the opening 913 and/or otherwise mate with the second shaft 910. In some examples, the outer wall 930 of the fitting 902 may abut a corresponding outer wall of the distal end 922 when the fitting 902 is removably attached to the adapter 920. The adapter 920 may also include a top surface 926 and a bottom surface 928 opposite the top surface 926. In such examples, the bottom surface 928 may mate with and/or may be otherwise connected to a corresponding surface of the cuff 12. Further, the adapter 920 may include one or more connection devices 932 operable to assist in removably attaching and detaching the fitting 902 from the adapter 920.

Figure 10:
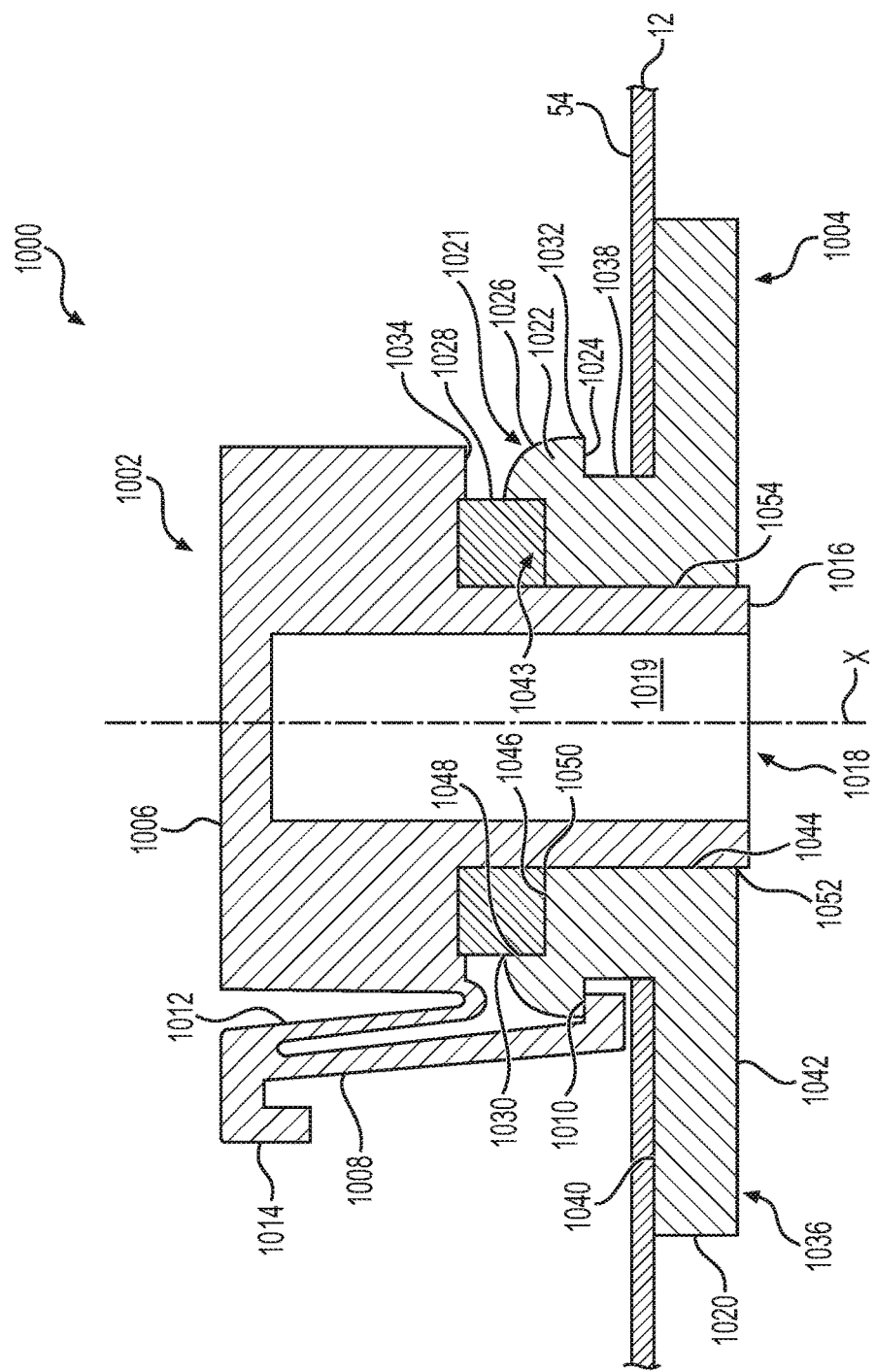
FIG. 10 is a cross-sectional view of a further example blood pressure cuff adapter and an example fitting removably attached to the adapter.
Figure 10A:
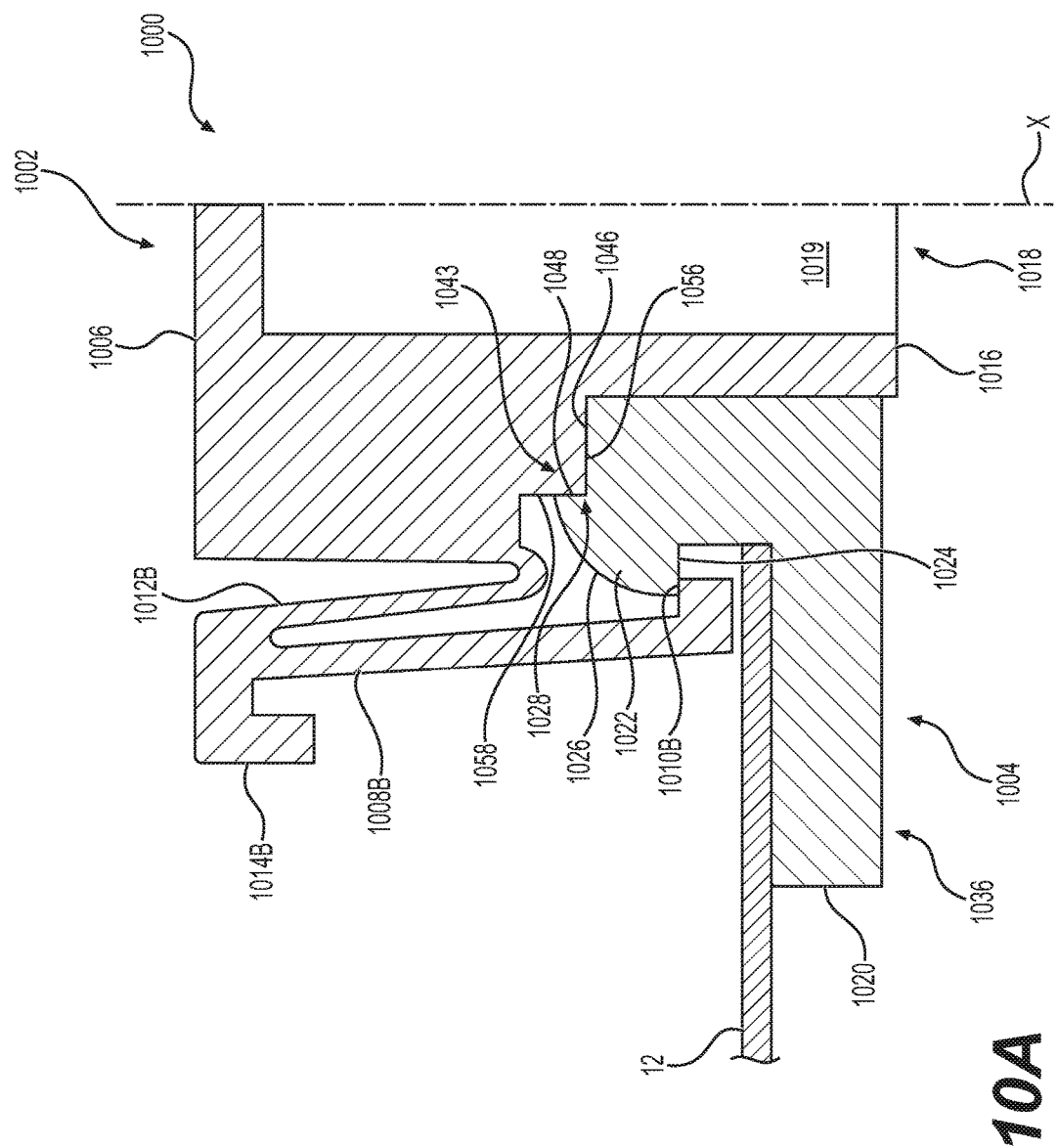
FIG. 10a is a partial cross-sectional view of still another example blood pressure cuff adapter and an example fitting removably attached to the adapter.

As shown in FIGS. 10 and 10a, another example system 1000 or other environment may include a fitting 1002 and/or a blood pressure cuff adapter 1004, and in such systems, the example fitting 1002 may include one or more arms or other connection devices configured to assist in removably attaching the fitting 1002 to the adapter 1004. Such example systems may also include a groove and/or other structure configured to mate with an annular seal, and the interaction between the groove and the seal may assist in retaining the fitting 1002 removably attached to the adapter 1004. In example embodiments, any of the structures, functions, and/or other aspects of the various fittings described herein may be included in the fitting 1002. Likewise, any of the structures, functions, and/or other aspects of the various adapters described herein may be included in the adapter 1004. Further, one or more of the structures, functions, and/or features of the fitting 1002, and/or of the adapter 1004, may be incorporated into any of the fittings or adapters of the present disclosure.

In the example system 1000, the fitting 1002 may include a substantially rigid body 1006, and a single arm 1008 extending from the body 1006. The arm 1008 may also include a shelf 1010 formed at a distal end of the arm 1008. The arm 1008 may be movably connected to the body 1006 via at least one stand 1012 extending from the body 1006. As can be seen from FIG. 10, the shelf 1010 may extend substantially perpendicularly from the arm 1008. In particular, the shelf 1010 may include one or more surfaces (e.g., a top surface, a bottom surface opposite the top surface, a side surface, etc.), extending substantially perpendicularly from the arm 1008, and such surfaces may be configured to mate with a corresponding surface of the adapter 1004 in order to removably attach the fitting 1002 to the adapter 1004.

At least one of the body 1006, stand 1012, arm 1008, shelf 1010, and/or other components of the fitting 1002 may be made from any of the materials described above with respect to the body 48. In any such examples, the shape, size, materials, and/or other configuration of the stand 1012 may provide for movement of the shelf 1010 relative to the body 1006 when force is applied to a grip 1014 associated with the stand 1012. Such movement may enable the fitting 1002 to be removably attached to the blood pressure cuff adapter 1004, and may also enable the fitting 1002 to be detached from the adapter 1004. As can be understood from the partial cross-sectional view shown in FIG. 10*a*, in further examples, the fitting 1002 may include more than one arm, shelf, stand, grip, and/or other components. For example, the fitting 1002 of.

FIG. 10*a* may include a first arm 1008*a* (not shown) and a second arm 1008*b*, a first shelf 1010*a* (not shown) and a second shelf 1010*b*, a first stand 1012*a* (not shown) and a second stand 112*b*, a first grip 1014*a* (not shown) and a second grip 1014*b*, etc. Additionally, as will be described below, the system 1000 may also include a seal, and a groove configured mate with the seal. Disposing the seal at least partially within the groove when removably attaching the fitting 1002 to the adapter 1004 may assist in removably attaching the fitting 1002 to the adapter 1004. Disposing the seal at least partially within the groove when removably attaching the fitting 1002 to the adapter 1004 may also form a substantially fluid-tight seal between the fitting 1002 and the adapter 1004.

The fitting 1002 may also include one or more extensions, passages, and/or other like channels 1016 extending from the body 1006. In some examples, the channel 1016 may extend substantially along the longitudinal axis Z (FIG. 2) of the fitting 1002, and the longitudinal axis Z may extend substantially centrally through the channel 1016. The channel 1016 may form an opening 1018 configured to permit the passage of air or other fluids into the cuff 12 via the fitting 1002, and/or to otherwise fluidly connect the fitting 1002 with the cuff 12, when the fitting 1002 is removably attached to the adapter 1004. The fitting 1002 may further include a central fluid passage 1019 extending at least partially through the body 1006. For example, the channel 1016 may form at least part of the central fluid passage 1019, and the longitudinal axis Z (FIG. 2) may extend substantially centrally through at least part of the central passage 1019. In such examples, the opening 1018 of the channel 1016 may comprise an opening of the central passage 1019.

As noted above with respect to the adapter 50 of FIG. 2, the adapter 1004 may include a substantially rigid body 1020 that is at least partly connected to the cuff 12. For example, the body 1020 may include a distal portion 1021 extending outwardly from the outer surface 54 of the cuff 12. The body 1020 may also include a proximal portion 1036 embedded within the cuff 12 and/or extending inwardly from the outer surface 54. In some examples, a top surface 1040 of the proximal portion 1036 may extend at least partly along and/or may be connected to an inner surface of the cuff 12 disposed opposite the outer surface 54. The proximal portion 1036 may also include a bottom surface 1042 opposite the top surface 1040 and disposed substantially within, for example, an inflated portion of the cuff 12. The body 1020 of the adapter 1004 may be made from any of the materials described above with respect to, for example, the fitting 42. In some examples, the adapter 1004 may be made from more than one such material. For example, one or more components or other parts of the distal portion 1021 may be made from a first material, and one or more components or other parts of the proximal portion 1036 may be made from a second material different from the first material. As noted above with respect to the adapter 50 of FIG. 2, in such examples, the use of such first and second materials may result in the various components or other parts of the body 1020 having different rigidities, durabilities, sealing characteristics, and/or other properties. In any of the embodiments described herein, including the example embodiments shown in FIGS. 10 and 10*a*, the fitting 1002 may also be made from more than one material. For example, one or more portions of the body 1006 may be made from a first material, and a seal, at least one stand 1012, at least one arm 1008, and/or other component of the fitting 1002 may be made from a second material different from the first material.

The distal portion 1021 of the adapter 1004 may include an annular ring 1022 having a top surface 1026 and a ridge 1024 disposed opposite the top surface 1026. The ridge 1024 may comprise at least part of a bottom surface of the ring 1022. In such examples, at least part of the ridge 1024 and/or at least another part of the bottom surface of the ring 1022 may be configured to mate with the shelf 1010 of the fitting 1002 to assist in retaining the fitting 1002 and/or otherwise removably attaching the fitting 1002 to the adapter 1004. In some examples, at least part of the ridge 1024 and/or at least another part of the bottom surface of the ring 1022 may extend substantially perpendicular to a longitudinal axis X of the body 1020. Additionally, the adapter 1004 may include a substantially cylindrical sidewall 1038 extending from the ridge 1024 to the top surface 1040 of the proximal portion 1036. Such a sidewall 1038 may space the ridge 1024 from the top surface 1040 such that the shelf 1010 of the fitting 1002 may have room to mate with the ridge 1024 beneath the ring 1022.

The top surface 1026 of the ring 1022 may be substantially convex, substantially concave, substantially curved, substantially tapered, and/or any other configuration in order to assist in removably attaching the fitting 1002 to the adapter 1004. In some examples, the top surface 1026 of the ring 1022 may comprise a convex surface extending radially away from the longitudinal axis X of the body 1020 from a distal end 1030 of the top surface 1026 to a proximal end 1032 of the top surface 1026. In such examples, the curved top surface 1026 may comprise a camming surface along which at least part of the arm 1008 and/or other components of the fitting 1002 may slide as the fitting 1002 is removably attached to the adapter 1004.

The system 1000 may also include one or more O-rings, gaskets, and/or other seals 1028 configured to form a substantially fluid-tight seal between the fitting 1002 and the adapter 1004 when the fitting 1002 is removably attached to the adapter 1004. For example, at least one seal 1028 may be attached to, adhered to, embedded substantially within, formed integrally with, and/or otherwise connected to either an outer surface 1034 of the fitting 1002 or to one or more portions of an annular groove 1043 formed by the ring 1026 to facilitate forming such a fluid-tight seal. As shown in FIG. 10, the seal 1028 may be connected to a portion of the outer surface 1034, and in some examples, at least part of the seal 1028 may be recessed and/or otherwise disposed in a groove formed by the outer surface and substantially surrounding the channel 1016. Alternatively, as shown in FIG. 10*a*, the seal 1028 may be embedded within and/or formed integrally with the body 1006 of the fitting 1002. In such examples, the seal 1028 may comprise a portion of the body 1006 configured to mate with the groove 1043 so as to form a substantially fluid-tight seal with the groove 1043 and/or other portions of the adapter 1004 (e.g., with the ring 1022) when the fitting 1002 is removably attached to the adapter 1004. In such examples, the seal 1028 may be formed from a first material (e.g., a first urethane and/or other polymer having a relatively low durometer), and at least part of the body 1006 may be formed from a second material (e.g., a second urethane and/or other polymer having a durometer higher than the first material) different from the first material.

In further example embodiments, the body 1006 shown in FIG. 10*a* may be formed from a single material. In such examples, at least the ring 1022 of the adapter 1004 may be formed from a first material (e.g., a first urethane and/or other polymer having a relatively low durometer), and the body 1006 may be formed from a second material (e.g., a second urethane and/or other polymer having a durometer higher than the first material) different from the first material. In such examples, a portion of the body 1006 may be configured to mate with the groove 1043 so as to form a substantially fluid-tight seal with the groove 1043 and/or other portions of the adapter 1004 (e.g., with the ring 1022) when the fitting 1002 is removably attached to the adapter 1004.

In the example system 1000 of FIGS. 10 and 10*a*, the groove 1043 may be formed, at least in part, by the top surface 1026 of the ring 1022, and the groove 1043 may comprise a base 1046 extending substantially perpendicular to the longitudinal axis X, and a sidewall 1048 extending substantially parallel to the longitudinal axis X. In such examples, the sidewall 1048 may extend distally from the base 1046 to the distal end 1030 of the top surface 1026.

Further, as shown in at least FIG. 10 the adapter 1004 may include a substantially cylindrical inner wall 1044 having a proximal end 1052 at the bottom surface 1042 of the proximal portion 1036, and a distal end 1050 at the base 1046 of the groove 1043. In such examples, the base 1046 may extend radially from the distal end 1050 of the inner wall 1044 to the sidewall 1048. In such examples, at least part (e.g., a base 1056) of the seal 1028 may be disposed within the groove 1043 when the fitting 1002 is removably attached to the adapter 1004. For example, in embodiments in which the seal 1028 is connected to the fitting 1002 (e.g., the embodiment of FIG. 10) or in which the seal 1028 is formed integrally with the fitting 1002 (FIG. 10*a*), the base 1056 of the seal 1028 may mate with and/or otherwise contact at least part of the base 1046 when the fitting 1002 is removably attached to the adapter 1004. Similarly, in such embodiments a radially outermost sidewall 1058 of the seal 1028 may mate with and/or otherwise contact at least part of the sidewall 1048 when the fitting 1002 is removably attached to the adapter 1004. Alternatively, in embodiments in which the seal 1028 is formed integrally with and/or connected to the adapter 1004, the base 1056 of the seal 1028 may be connected to the base 1046 of the groove 1043. Further, in such embodiments at least part of the radially outermost sidewall 1058 of the seal 1028 may be connected to the sidewall 1048 of the groove 1043. In such examples, the seal 1028 may engage the outer surface 1034 of the fitting 1002 and/or an outer surface 1054 of the channel 1016 to form a substantially fluid-tight seal with the fitting 1002. Such engagement may also assist in removably attaching the fitting 1002 to the adapter 1004. For example, the flexible seal 1028 may have an inner diameter that is substantially equal to or nominally less than an outer diameter of the outer surface 1054. Accordingly, the seal 1028 may apply a retention force to the outer surface 1054 in a radially inward direction when the channel 1016 is inserted within the adapter 1004. Such a retention force may assist in removably attaching the fitting 1002 to the adapter 1004.

In still further examples, in the embodiment shown in FIG. 10, the seal 1028 may be attached to, adhered to, embedded substantially within, and/or otherwise connected to the outer surface 1034 of the fitting 1002 (as described above) and/or to the outer surface 1054 of the channel 1016. For example, as noted above with respect to FIG. 10 a top portion of the seal 1028 may be connected to a groove formed by the outer surface 1034 of the fitting 1002. Further, at least part of a sidewall of the seal 1028 (e.g., a radially inner sidewall of the seal 1028 shown in FIG. 10) may be connected to and/or disposed on the outer surface 1054 of the channel 1016. In such examples, the seal 1028 may engage the sidewall 1048 and/or the base 1046 of the groove 1043 formed by the adapter 1004 to form a substantially fluid-tight seal with the adapter 1004. Such engagement may also assist in removably attaching the fitting 1002 to the adapter 1004. For example, the flexible seal 1028 may have an outer diameter that is substantially equal to or nominally greater than a diameter of the groove 1043 formed by the sidewall 1048. Accordingly, the seal 1028 may apply a retention force to the sidewall 1048 in a radially outward direction when the channel 1016 is inserted within the adapter 1004. Such a retention force may assist in removably attaching the fitting 1002 to the adapter 1004. In the embodiment shown in FIG. 10, the seal 1028 may comprise a primary seal configured to mate with at least a portion of the fitting 1002 (e.g., the outer surface 1034), and the annular ring 1022 may comprise a secondary seal that is also configured to mate with at least a portion of the fitting 1002 (e.g., the outer surface 1054 of the channel 1016 and/or the outer surface 1034. In such examples, the seal 1028 and/or the ring 1022 may be shaped, sized, located, and/or otherwise configured to increase the stability of the removable connection between the adapter 1004 and the fitting 1002.

Further, the body 1020 of the adapter 1004 may also include a central opening (as shown more clearly in FIG. 2)

at least partially formed by the wall 1044 of the body 1020. For example, the inner wall 1044 may define a central fluid passage of the adapter 1004 configured to accept air or other fluids delivered to the cuff 12 via the fitting 1002. In such examples, the inner wall 1044 may have any shape, size, diameter, and/or other configuration such that the inner wall 1044 may accept at least part of the channel 1016 therein. For example, at least part of the channel 1016 may pass through the central opening of the inner wall 1044, proximate the distal end 1030 of the top surface 1026, when the fitting 1002 is removably attached to the adapter 1004. In such examples, the longitudinal axis X may extend substantially centrally through the central fluid passage of the adapter 1004 formed by the substantially cylindrical inner wall 1044.

As shown in FIG. 11, still another example system 1100 or other environment may include a fitting 1102 and/or a blood pressure cuff adapter 1104, and in such systems, the example fitting 1102 may be configured to mate with the adapter 1104 by moving the fitting 1102 in a direction substantially perpendicular to a central longitudinal axis X of the adapter 1104 and/or in a direction substantially parallel to a top surface of the cuff 12 to which the adapter 1104 is connected. Such example fittings 1102 may include a groove and/or other structure configured to assist in securing the fitting 1102 to the adapter 1104 when the fitting 1102 is removably attached to the adapter 1104. In example embodiments, any of the structures, functions, and/or other aspects of the various fittings described herein may be included in the fitting 1102. Likewise, any of the structures, functions, and/or other aspects of the various adapters described herein may be included in the adapter 1104. Further, one or more of the structures, functions, and/or features of the fitting 1102, and/or of the adapter 1104, may be incorporated into any of the fittings or adapters of the present disclosure.

In the example system 1100, the fitting 1102 may include a substantially rigid body 1106, and the body 1106 may be substantially cylindrical and/or any other shape configured to assist in mating the fitting 1102 with the adapter 1104. The body 1106 may include, for example, a pocket 1108 shaped, sized, and/or otherwise configured to accept at least part of the adapter 1104 therein and to form a substantially fluid-tight seal with the adapter 1104. As shown in FIG. 11, the pocket 1108 may be formed, at least in part, by an inner sidewall 1110 of the body 1106. The pocket 1108 may also be formed, at least in part, by a ceiling 1112 of the body 1106 extending substantially perpendicular to the inner sidewall 1110. In such examples, the pocket 1108 may include an opening at a distal end of the body 1106 configured to accept at least part of the adapter 1104 when the fitting 1102 is removably attached to the adapter 1104. In particular, the opening of the pocket 1108 may enable the fitting 1102 to be mated with the adapter 1104 by moving the fitting 1102 in a direction substantially perpendicular to the central longitudinal axis X of the adapter 1104 and/or in a direction substantially parallel to a top surface of the cuff 12 to which the adapter 1104 is connected. The body 1106 may also include an outer top surface 1114 opposite the ceiling 1112, and an inner bottom surface 1116 opposite the top surface 1114. In such examples, the bottom surface 1116 may be disposed proximate and/or adjacent to the top surface of the cuff 12 when the fitting 1102 is removably attached to the adapter 1104.

In some examples, the body 1106 may also include a substantially circumferential groove 1118. For example, the groove 1118 may comprise a channel or other like structure formed by the inner sidewall 1110 and extending at least partially circumferentially around a central longitudinal axis (not shown) of the fitting 1102. The groove 1118 may include any width, height, depth, and/or other configuration/structure to assist in removably attaching the fitting 1102 with the adapter 1104. For example, as will be described below, the adapter 1104 may include a distal portion having a ring and a ridge, and in such embodiments the groove 1118 may be configured to accept at least part of the distal portion therein when the fitting 1102 is removably attached to the adapter 1104. Further, while the opening of the pocket 1108 may enable the fitting 1102 to be mated with the adapter 1104 by moving the fitting 1102 in a direction substantially perpendicular to the central longitudinal axis X of the adapter 1104 and/or in a direction substantially parallel to a top surface of the cuff 12, the groove 1118 may be substantially annular and/or any other configuration so as to enable rotation of the fitting 1102 about the longitudinal axis X when the fitting 1102 is removably attached to the adapter 1104.

As shown in FIG. 11, the adapter 1104 may include a substantially rigid body 1120 that is at least partly connected to the cuff 12. For example, the body 1120 may include a distal portion 1121 extending outwardly from the outer surface of the cuff 12. The body 1120 may also include a proximal portion 1136 embedded within the cuff 12 and/or extending inwardly from the outer surface of the cuff 12. In some examples, a top surface of the proximal portion 1136 may extend at least partly along and/or may be connected to an inner surface of the cuff 12. The body 1120 of the adapter 1104 may be made from any of the materials described above with respect to, for example, the fitting 42. In some examples, the adapter 1104 may be made from more than one such material. For example, one or more components or other parts of the distal portion 1121 may be made from a first material, and one or more components or other parts of the proximal portion 1136 may be made from a second material different from the first material.

The distal portion 1121 of the adapter 1104 may include an annular ring 1122 having a top surface 1126 and a ridge 1124 disposed opposite the top surface 1126. The ridge 1124 may comprise at least part of a bottom surface of the ring 1122. In such examples, at least part of the ridge 1124 and/or at least another part of the bottom surface of the ring 1122 may be configured to mate with the groove 1118 of the fitting 1102 (e.g., a bottom surface, bottom wall, bottom flange, bottom shelf, etc.) to assist in retaining the fitting 1102 and/or otherwise removably attaching the fitting 1102 to the adapter 1104. In some examples, at least part of the ridge 1124 and/or at least another part of the bottom surface of the ring 1122 may extend substantially perpendicular to the longitudinal axis X of the body 1120. Further, at least part of the ridge 1124 and/or at least part of the ring 1122 may be disposed substantially within the groove 1118 when the fitting 1102 is removably attached to the adapter 1104. Additionally, the adapter 1104 may include a substantially cylindrical sidewall 1138 extending from the ridge 1124 to the top surface of the proximal portion 1136. Such a sidewall 1138 may space the ridge 1124 from the top surface of the proximal portion 1136 such that the groove 1118 of the fitting 1102 may have room to mate with the ridge 1124. In such examples, at least part of the body 1106 (e.g., the bottom surface 1116) may be disposed beneath the ring 1122 when the fitting 1102 is removably attached to the adapter 1104.

The top surface 1126 of the ring 1122 may be substantially convex, substantially concave, substantially curved, substantially tapered, and/or any other configuration in order to assist in removably attaching the fitting 1102 to the adapter 1104. In some examples, the top surface 1126 of the ring 1122 may comprise a convex surface extending radially away from the longitudinal axis X of the body 1120 from a distal end of the top surface 1126 to a proximal end of the top surface 1126.

The system 1100 may also include one or more O-rings, gaskets, and/or other seals 1128 configured to form a substantially fluid-tight seal between the fitting 1102 and the adapter 1104 when the fitting 1102 is removably attached to the adapter 1104. For example, at least one seal 1128 may be attached to, adhered to, embedded substantially within, formed integrally with, and/or otherwise connected to either an outer surface of the fitting 1102 or to one or more portions of an annular groove 1146 formed by the ring 1126 to facilitate forming such a fluid-tight seal. In the example system 1100 of FIG. 11, the groove 1146 may be formed, at least in part, by the top surface 1126 of the ring 1122. In still further embodiments, the seal 1128 may be omitted. In such example embodiments the adapter 1104 (e.g., at least part of the top surface 1126 and/or other portions of the ring 1122) may be made from a first material (e.g., an example urethane or other polymer) having a first durometer. The fitting 1102, on the other hand, may be made from a second material (e.g., an example polymer) having a second durometer that is relatively higher than the first durometer of the first material. In such examples, the relatively lower durometer first material of the adapter 1104 may be configured to form a substantially fluid tight seal with the relatively higher durometer second material when the fitting 1102 is releasable connected to the adapter 1104. In still further embodiments, the fitting 1102 may be made from the relatively lower durometer first material described above and the adapter 1104 may be made from the relatively higher durometer second material described above.

Further, in any of the embodiments of the system 1100 shown in FIG. 11, the fitting 1102 may be shaped, sized, and/or otherwise configured to be installed directly over the top of the adapter 1104 in order to form a removable connection therewith and/or to form a substantially fluid-tight seal therewith. In such examples, the fitting 1102 (e.g., the body 1106 of the fitting 1102) may be substantially cylindrical, and may be configured to form a substantially fluid-tight seal with the seal 1128 and/or with at least part of the ring 1122 when the fitting 1102 is removably connected to the adapter 1104.

Further, as shown in FIG. 11 the adapter 1104 may include a substantially cylindrical inner wall 1144 having a proximal end at a bottom surface of the proximal portion 1036, and a distal end at the top surface 1126 of the ring 1122. In such examples, the inner wall 1144 may form a central opening 1160 of the adapter 1104 extending from the bottom surface of the proximal portion 1036 to the top surface 1126 of the ring 1122. In such examples, the longitudinal axis X may extend substantially centrally through the central opening 1160 formed by the inner wall 1114.

In example embodiments, the body 1106 may also include one or more channels 1150a, 1150b. For example, such channels 1150a, 1150b may be formed, at least in part, by the ceiling 1112 and may extend into the ceiling 1112 at any desired depth. Each channel 1150a, 1150b may be fluidly connected to a respective fluid passage 1152a, 1152b of the body. For example, each fluid passage 1152a, 1152b may be fluidly connected to a respective conduit section 32a, 32b of the tubing 30. As a result, fluid delivered to the body 1106 by the conduit sections 32a, 32b may be passed to the channels 1150a, 1150b by the respective fluid passages 1152a, 1152b, and the channels 1150a, 1150b may pass such fluid to the central opening 1160 of the adapter 1104 when the fitting 1102 is removably attached to the adapter 1104.

Figure 12:
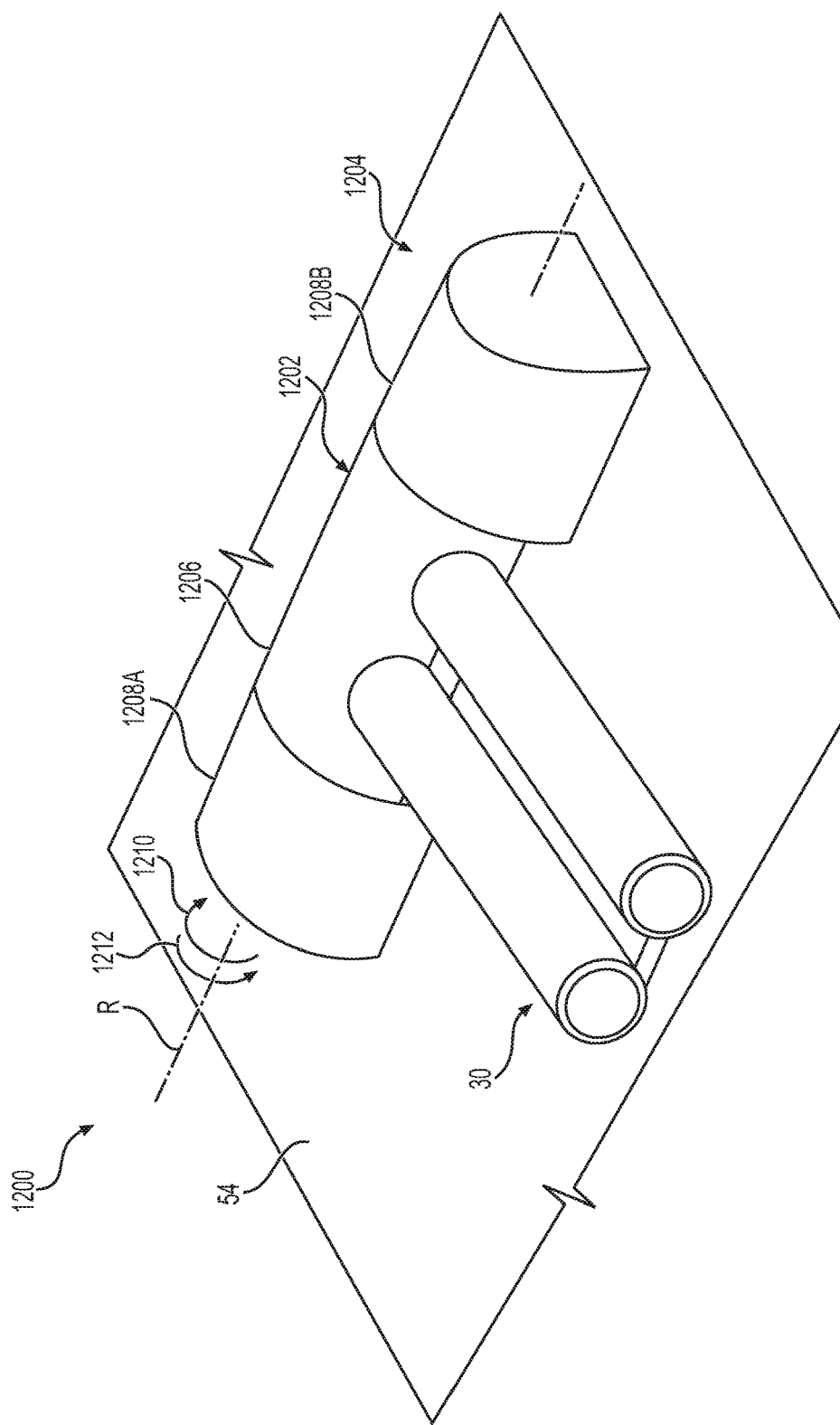
FIG. 12 is an isometric view of still another example blood pressure cuff adapter and an example fitting removably attached to the adapter.

As shown in FIG. 12, yet another example system 1200 or other environment may include a fitting 1202 and/or a blood pressure cuff adapter 1104, and in such systems, the example fitting 1102 may be configured to mate with the adapter 1104 by moving the fitting 1102 in a direction substantially perpendicular to a rotational axis R defined by the adapter 1204. In some examples, the rotational axis R may comprise a central longitudinal axis of the adapter 1104, and the fitting 1202 may be configured to rotate about the rotational axis R when the fitting 1202 is removably attached to the adapter 1204. As shown in FIG. 12, the rotational axis R may extend substantially parallel to a top surface 54 of the cuff 12 to which the adapter 1204 is connected, and the fitting 1202 may have a range of motion about the rotational axis R equal to at least approximately 180 degrees. For example, the fitting 1202 may be rotatable about the rotational axis R in the clockwise direction of arrow 1210 and in the counter-clockwise direction of arrow 1212. It is understood that such an example adapter 1204 may have one or more grooves, channels, pockets, and/or other structures configured to mate with at least part of the fitting 1202, and such structures may assist in removably attaching the fitting 1202 to the adapter 1204. In example embodiments, any of the structures, functions, and/or other aspects of the various fittings described herein may be included in the fitting 1202. Likewise, any of the structures, functions, and/or other aspects of the various adapters described herein may be included in the adapter 1204. Further, one or more of the structures, functions, and/or features of the fitting 1202, and/or of the adapter 1204, may be incorporated into any of the fittings or adapters of the present disclosure.

In the example system 1200, the fitting 1202 may include a substantially rigid body 1206, and the body 1206 may be substantially cylindrical and/or any other shape configured to assist in mating the fifing 1202 with the adapter 1204. The body 1206 may include, for example, one or more pockets, extensions, tabs, pins, channels, and/or other structures (not shown) shaped, sized, and/or otherwise configured to mate with at least part of the adapter 1204 and to form a substantially fluid-tight seal with the adapter 1204. The adapter 1204 and/or the fitting 1202 may also include one or more seals (not shown) similar to one or more of the seals described above, to assist in forming such a substantially fluid-tight seal.

In some examples, the adapter 1204 may include a first portion 1208a and a second portion 1208b disposed opposite the first portion 1208a on the top surface 54. In such examples, the body 1206 of the fitting 1202 may be positioned between the first and second portions 1208a, 1208b when the fitting 1202 is removably attached to the adapter 1204. Further, the first and second portions 1208a, 1208b may include respective fluid passages configured to direct fluid into the cuff 12. In such examples, a first fluid passage of the fitting 1202 may be fluidly connected to a respective fluid passage of the first portion 1208a, and a second fluid passage of the fitting 1202 may be fluidly connected to a respective fluid passage of the second portion 1208b when the fitting 1202 is removably attached to the adapter 1204.

As shown in FIGS. 13a and 13b, a further example system 1300 or other environment of the present disclosure may include a fitting 1302 and/or a blood pressure cuff adapter 1304. In such systems 1300, the example fitting 1302 may be removably attachable to such an adapter 1304, and in such a system 1300, the fitting 1302 may comprise a body 1306 having an upper section 1308 that is relatively flexible and/or malleable. For example, the upper section 1308 may comprise a first portion 1310a and a second portion 1310b opposite the first portion 1310a. As shown in FIG. 13b, at least one of the first and second portions 1310a, 1310b may be deformable to assist in securing the fitting 1302 to the adapter 1304 when the fitting 1302 is removably attached to the adapter 1302. Such a malleable upper section 1308 may also form a substantially fluid-tight seal with at least part of the adapter 1304 when the fitting 1302 is removably attached to the adapter 1304. In such examples, one or more of the seals described above, such as the seal 1328 shown in FIGS. 13a, 13b may be omitted. In example embodiments, any of the structures, functions, and/or other aspects of the various fittings described herein may be included in the fitting 1302. Likewise, any of the structures, functions, and/or other aspects of the various adapters described herein may be included in the adapter 1304. Further, one or more of the structures, functions, and/or features of the fitting 1302, and/or of the adapter 1304, may be incorporated into any of the fittings or adapters of the present disclosure.

In the example system 1300, various components of the fitting 1302 may be substantially similar to corresponding components of the fitting 502, and various components of the adapter 1304 may be substantially similar to corresponding components of the adapter 504. The body 1306 and/or other components of the fitting 1302 may be made from any of the materials described above with respect to the body 48. In any such examples, the shape, size, materials, and/or other configuration of the upper portion 1308 may enable at least one of the first portion 1310a, or the second portion 1310b to mate with a surface of the adapter 1304. Such flexibility and/or malleability of the upper section 1308 may enable the fitting 1302 to be removably attached to the blood pressure cuff adapter 1304.

The fitting 1302 may also include one or more extensions, passages, and/or other like channels 1316 extending from the body 1306. In some examples, the channel 1316 may extend substantially along the longitudinal axis X of the fitting 1302, and the longitudinal axis X may extend substantially centrally through the channel 1316. The channel 1316 may form an opening 1318 configured to permit the passage of air or other fluids into the cuff 12 via the fitting 1302, and/or to otherwise fluidly connect the fitting 1302 with the cuff 12, when the fitting 1302 is removably attached to the adapter 1304. The fitting 1302 may further include a central fluid passage 1319 extending at least partially through the body 1306. For example, the channel 1316 may form at least part of the central fluid passage 1319 of the fitting 1302, and the longitudinal axis X may extend substantially centrally through at least part of the central passage 1319. In such examples, the opening 1318 of the channel 1316 may comprise an opening of the central passage 1319.

With further reference to FIGS. 13a and 13b, the adapter 1304 may include a substantially rigid body that is at least partly connected to the cuff 12. For example, the body may include a distal portion having an annular ring 1322. The ring 1322 may include a top surface 1326 and a ridge 1324 disposed opposite the top surface 1326. The ridge 1324 may comprise at least part of a bottom surface of the ring 1322. In such examples, at least part of the ridge 1324 and/or at least another part of the bottom surface of the ring 1322 may be configured to mate with at least one of the first portion 1310a or the second portion 1310b of the fitting 1302 to assist in retaining the fitting 1302 and/or otherwise removably attaching the fitting 1302 to the adapter 1304. In some examples, at least part of the ridge 1324 and/or at least another part of the bottom surface of the ring 1322 may extend substantially perpendicular to the longitudinal axis X. Additionally, the adapter 1304 may include a substantially cylindrical sidewall extending proximally from the ridge. Such a sidewall may space the ridge 1324 from a proximal portion of the adapter 1304 such that a healthcare professional may mold and/or otherwise form at least one of the first portion 1310a or the second portion 1310b of the fitting 1302 to mate with the ridge 1324 beneath the ring 1322.

The system 1300 may also include one or more O-rings, gaskets, and/or other seals 1328 configured to form a substantially fluid-tight seal between the fitting 1302 and the adapter 1304 when the fitting 1302 is removably attached to the adapter 1304. For example, at least one seal 1328 may be attached to, adhered to, embedded substantially within, and/or otherwise connected to either an outer surface 1334 of the fitting 1302 or to the top surface 1326 of the ring 1322 to facilitate forming such a fluid-tight seal. In the example system 1300, at least part (e.g., a base) of the seal 1328 may be disposed within an annular groove formed by the top surface 1326 of the ring 1322.

In such examples, the seal 1328 may engage the outer surface 1334 of the fitting 1302 proximate a perimeter and/or outer wall of the channel 1316 to form a substantially fluid-tight seal with the fitting 1302 when the fitting 1302 is removably attached to the adapter 1304. Alternatively, the seal 13528 may be attached to, adhered to, embedded substantially within, and/or otherwise connected to the outer surface 1334 of the fitting 1302, and may be configured to engage the top surface 1326 of the adapter 1304 to form such a substantially fluid-tight seal. In still further embodiments, the seal 1328 may be omitted.

As shown in FIGS. 14a-14f, another example system 1400 or other environment may include a fitting 1402 and/or a blood pressure cuff adapter 1404, and in such systems, the example fitting 1402 may include one or more arms or other connection devices configured to assist in removably attaching the fitting 1402 to the adapter 1404. As will be described below, at least some such example systems may also include a groove and/or other structure configured to mate with at least part of a member of the fitting 1402, and the interaction between the groove and the member of the fitting 1402 may assist in aligning and/or stabilizing the fitting 1402 relative to the adapter 1404 when the fitting 1402 is removably attached to the adapter 1404. In example embodiments, any of the structures, functions, and/or other aspects of the various fittings described herein may be included in the fitting 1402. Likewise, any of the structures, functions, and/or other aspects of the various adapters described herein may be included in the adapter 1404. Further, one or more of the structures, functions, and/or features of the fitting 1402, and/or of the adapter 1404, may be incorporated into any of the fittings or adapters of the present disclosure.

In the example system 1400, the fitting 1402 may include a substantially rigid body 1406. As can be understood from the partial cross-sectional views shown in FIGS. 14a-14f, the fitting 1402 may also include one or more arms, shelfs, stands, grips, and/or other components. For example, the fitting 1402 may include a first arm 1408a (not shown) and a second arm 1408b, a first shelf 1410a (not shown) and a second shelf 1410b, a first stand 1412a (not shown) and a second stand 112b, a first grip 1414a (not shown) and a second grip 1414b, etc. In some examples, such components may be substantially similar to and/or the same as the corresponding components of the adapters 700 described above with respect to, for example, FIGS. 7*a*-7*g*. For example, the arms 1408*a*, 1408*b* may include respective shelfs 1410*a*, 1410*b* formed at respective distal ends of the arms 1408*a*, 1408*b*. The arms 1408*a*, 1408*b* may be movably connected to the body 1406 via respective stands 1412*a*, 1412*b* extending from the body 1406. As can be seen from FIGS. 14*a*-14*f*, the shelves 1410*a*, 1410*b* may extend substantially perpendicularly relative to the longitudinal axis X. In particular, the respective shelves 1410*a*, 1410*b* may include one or more surfaces (e.g., a top surface, a bottom surface opposite the top surface, a side surface, etc.), extending substantially perpendicularly relative to a central longitudinal axis X of the adapter 1410, and such surfaces may be configured to mate with respective corresponding surfaces of the adapter 1404 in order to removably attach the fitting 1402 to the adapter 1404 as described above.

Additionally, the system 1400 may include one or more O-rings, gaskets, and/or other seals 1437 configured to form a substantially fluid-tight seal between the fitting 1402 and the adapter 1404 when the fitting 1402 is removably attached to the adapter 1404. Such seals 1437 may be substantially similar to and/or the same as the one or more seals 737 described above with respect to, for example, FIGS. 7*a*-7*g*. For example, the fitting 1402 may include a central channel 1416 defining a central fluid passage of the fitting 1402, and when the fitting 1402 is removably attached to the adapter 1404, a substantially cylindrical outer wall 1440 of the fitting 1402 disposed opposite the channel 1416 may be disposed along, adjacent, and/or at least partly in contact with a corresponding substantially cylindrical inner wall 1438 of the adapter 1404. In such examples, the at least one seal 1437 may be attached to, adhered to, embedded substantially within, disposed adjacent to, and/or otherwise connected to the inner wall 1438 of the adapter 1404 to facilitate forming such a fluid-tight seal. In particular, the seal 1437 may engage the outer wall 1440 to form a substantially fluid-tight seal with the fitting 1402 when the fitting 1402 is removably attached to the adapter 1404.

With continued reference to FIGS. 14*a*-14*f*, and as described above with respect to at least the adapter 1404 of FIGS. 7*a*-7*g*, the adapter 1404 of the system 1400 may include a substantially rigid body that is at least partly connected to a cuff 12. For example, the body of the adapter 1404 may include a distal portion 1421 extending outwardly from an outer surface of the cuff 12. The body of the adapter 1404 may also include a proximal portion embedded within the cuff 12 and/or extending inwardly from the outer surface of the cuff 12. The distal portion 1421 of the adapter 1404 may include an annular ring 1422 having a top surface 1426 and a ridge 1424 disposed opposite the top surface 1426. The ridge 1424 may comprise at least part of a bottom surface of the ring 1422. In such examples, at least part of the ridge 1424 and/or at least another part of the bottom surface of the ring 1422 may be configured to mate with the shelves 1410*a*, 1410*b* of the fitting 1402 to assist in retaining the fitting 1402 and/or otherwise removably attaching the fitting 1402 to the adapter 1404. In some examples, at least part of the ridge 1424 and/or at least another part of the bottom surface of the ring 1422 may extend substantially perpendicular to the longitudinal axis X of the adapter 1404. Additionally, the adapter 1404 may include a substantially cylindrical sidewall extending proximally from the ridge 1424. Such a sidewall may space the ridge 1424 from, for example, the top surface of the cuff 12 such that the shelves 1410*a*, 1410*b* of the fitting 1402 may have room to mate with the ridge 1424 beneath the ring 1422.

Figure 14A:
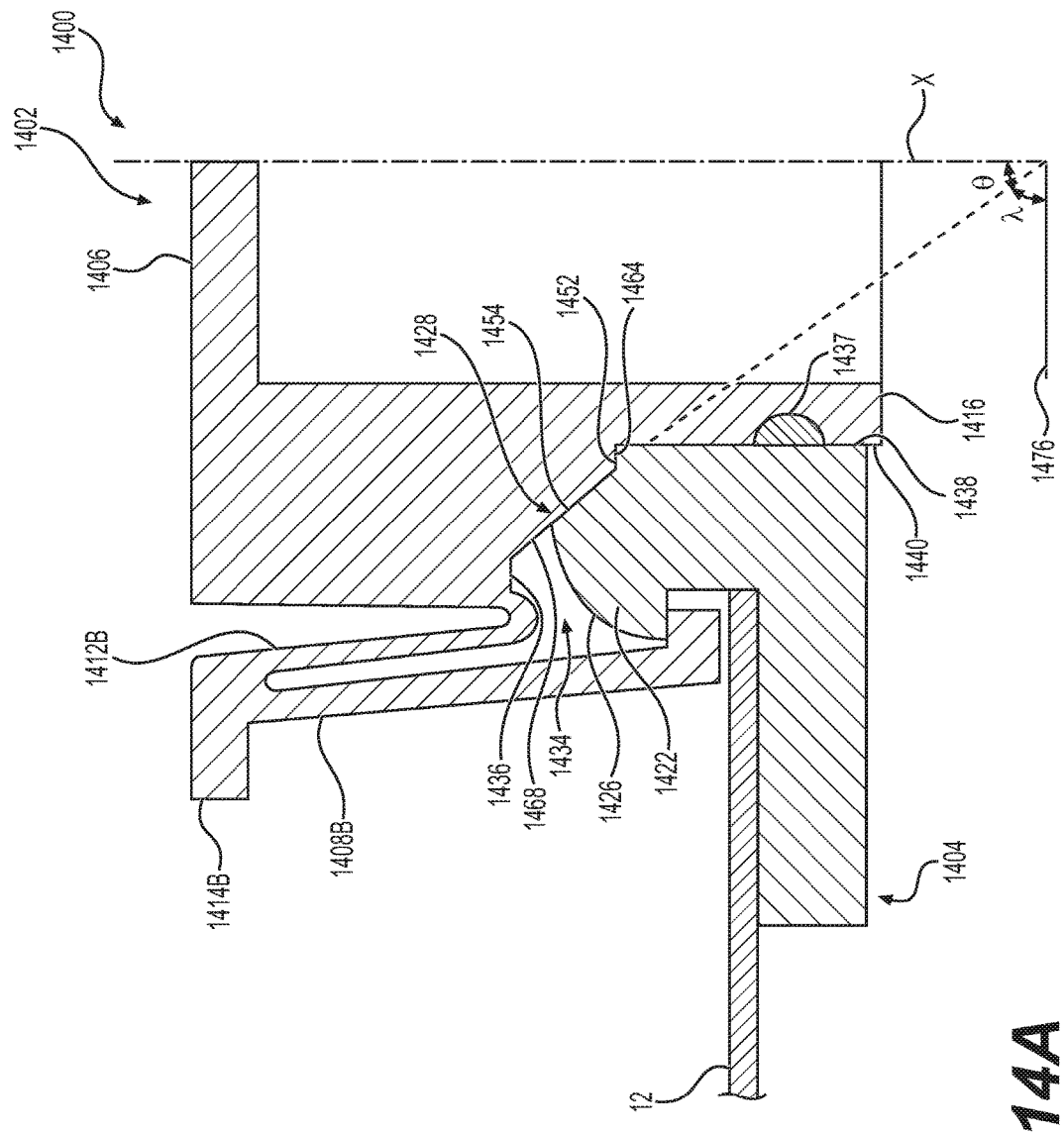
FIG. 14a is a partial cross-sectional view of an example blood pressure cuff adapter and an example fitting removably attached to the adapter.

With reference to at least FIG. 14*a*, in some examples the system 1400 may include an adapter 1404 having an annular groove 1428, and a fitting 1402 having one or more protruding members 1434 configured to at least partly engage the groove 1428 when the fitting 1402 is releasably attached to the adapter 1404. For example, similar to the adapter 1404 described with respect to FIGS. 7*a*-7*g*, in example embodiments, the ring 1422 of the adapter 1404 may include a groove 1428 extending at least partly (and, in some examples, completely) around (e.g., concentrically) the longitudinal axis X, and being shaped, sized, located, and/or otherwise configured to accept the member 1434 and/or other structural feature of the adapter 1402. As shown in at least FIG. 14*a*, such a member 1434 may extend distally (e.g., in a direction toward the cuff 12 when the fitting 1402 is removably attached to the adapter 1404) from an outer surface 1436 of the fitting 1402 disposed opposite and/or facing the top surface 1426 when the fitting 1402 is removably attached to the adapter 1404. In some examples, the member 1434 may comprise a shaft, pin, rod, tab, rib, ring, ridge, flange, and/or other extension of the body 1406 protruding from the outer surface 1436, and the member 1434 may be useful in laterally and/or otherwise aligning the fitting 1402 with the adapter 1404 when removably attaching the fitting 1402 to the adapter 1404. In particular, as shown in FIG. 14*a*, in some examples the member 1434 may comprise one or more tabs, ribs, rings, ridges, flanges, and/or other structures extending distally from the outer surface 1436, and having at least one surface that tapers radially inwardly from the outer surface 1436 toward the outer wall 1440. For example, the member 1434 may comprise at least one rib, tab, or other such structure including a radially outermost sidewall 1468. The sidewall 1468 may extend from a proximal end of the member 1434 (e.g., proximate or at the outer surface 1436) to a distal end of the member 1434, and the sidewall 1468 may taper radially inwardly from the proximal end of the member 1434 to the distal end of the member 1434.

The sidewall 1468 may be substantially planar, substantially concave, substantially convex, and/or any other shape or configuration, and such a configuration may match a configuration of a corresponding portion of the groove 1428. For instance, the member 1434 may also include a base 1464 disposed at the distal end thereof, and the groove 1428 may include a base 1452 and a radially outermost sidewall 1454 extending proximally from the base 1452. For example, the sidewall 1454 may extend proximally from the base 1452 to the top surface 1426 of the ring 1422. In such examples, the sidewall 1454 may mate with and/or otherwise at least partially engage the radially outermost sidewall 1468 of the member 1434 when the fitting 1402 is removably attached to the adapter 1404. Similarly, in some examples the base 1452 may mate with and/or otherwise at least partially engage the base 1464 of the member 1434 when the fitting 1402 is removably attached to the adapter 1404. Such engagement between the member 1434 and the groove 1428 may assist in minimizing and/or substantially eliminating lateral movement of the fitting 1402 relative to the adapter 1404 when the fitting 1402 is removably attached to the adapter 1404. In any such examples, the member 1434 may be shaped, sized, dimensioned, located, and/or otherwise configured to provide additional rigidity, support, and/or stability to the removable connection between the fitting 1402 and the adapter 1404, while still facilitating rotation of the fitting 1402 relative to the adapter 1404.

In such examples, the groove 1428 and the member 1434 may be positioned and/or otherwise configured such that disposing at least part of the member 1434 within the groove 1428 when removably attaching the fitting 1402 to the adapter 1404 may cause the longitudinal axis Z of the fitting 1402 (FIG. 2) to be collinear with the longitudinal axis X of the adapter 1404. Moreover, the sidewall 1468 of the member 1434 and the sidewall 1454 of the groove 1428 may be disposed at complimentary angles relative to, for example, the longitudinal axis X to facilitate such a mating relationship. For instance, the sidewall 1454 of the groove 1428 may be disposed at an acute included angle α relative to the longitudinal axis X. In such examples, the sidewall 1468 of the member 1434 may be disposed at a complimentary acute included angle A. Such an example relationship is shown in FIG. 14*a* with respect to an axis 1476 extending perpendicular to the longitudinal axis X.

Figure 14B:
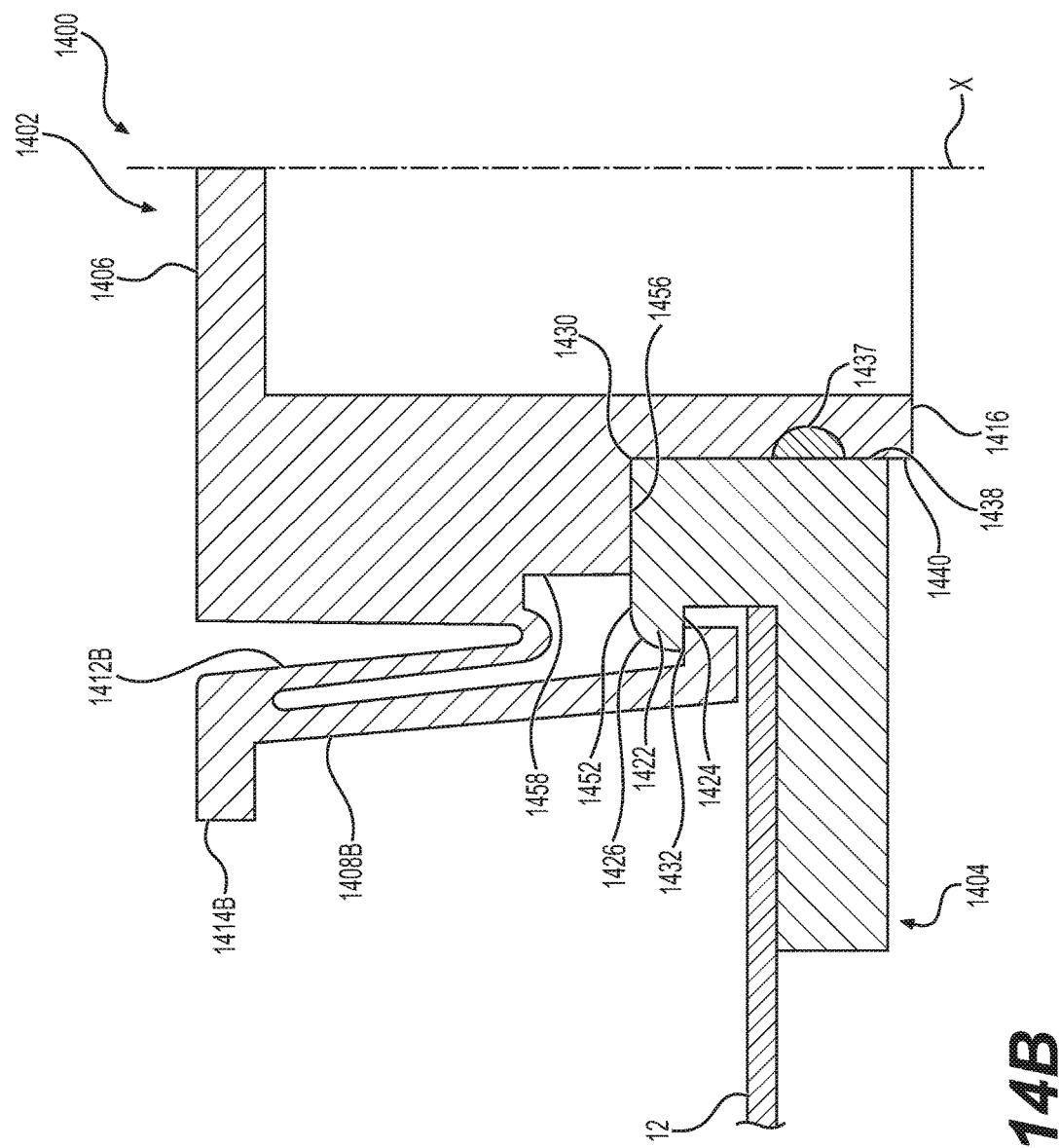
FIG. 14b is a partial cross-sectional view of another example blood pressure cuff adapter and an example fitting removably attached to the adapter.

With reference to at least FIG. 14*b*, in some examples the system 1400 may include an adapter 1404 in which the annular groove 1428 described above with respect to FIG. 14*a* has been omitted. For example, as shown in FIG. 14*b*, an example system 1400 may include a fitting 1402 and an adapter 1404 that are substantially similar to the fitting 1402 and adapter 1404 described above with respect to FIG. 14*a*. As shown in FIG. 14*b*, however, in some embodiments the top surface 1426 of the ring 1422 may terminate at a substantially planar surface (e.g., a base 1452). In such examples, the fitting 1402 may also include a corresponding substantially planar base 1456 configured to contact, engage, and/or otherwise mate with the base 1452 when the fitting 1402 is removably attached to the adapter 1404. In such examples, the base 1456 of the fitting 702 may comprise a substantially planar, substantially annular surface extending radially away from the outer surface 1440. In some examples, the fitting 1402 may also include one or more additional sidewalls 1458 extending substantially parallel to the sidewall 1440. In any such examples, the base 1456 may extend between the sidewall 1440 and the sidewall 1458. In some examples, the base 1456 may extend from the sidewall 1440 to the sidewall 1458. In any such examples, the base 1452 of the adapter 704 may comprise a substantially planar annular surface, and the base 1456 may contact, engage, and/or otherwise mate with at least part of the base 1452 when the fitting 1402 is removably attached to the adapter 1404.

Figure 14C:
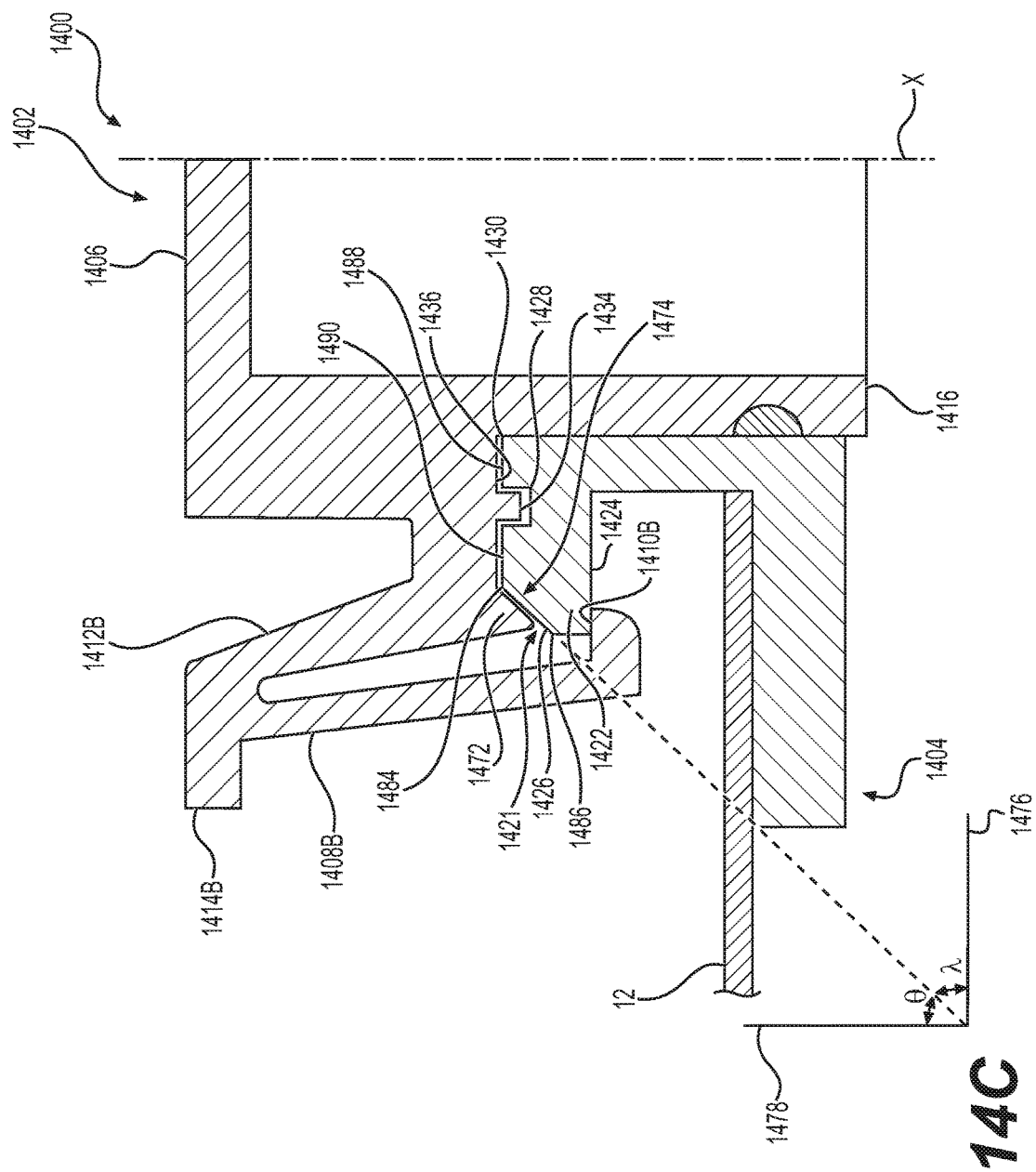
FIG. 14c is a partial cross-sectional view of still another example blood pressure cuff adapter and an example fitting removably attached to the adapter.

With reference to at least FIG. 14*c*, in some examples the system 1400 may include an adapter 1404 having an annular groove 1428, and a fitting 1402 having one or more protruding members 1434 configured to at least partly engage (e.g., at least partly extend into, at least partly contact, at least partly slidably engage, etc.) the groove 1428 when the fitting 1402 is releasably attached to the adapter 1404. For example, similar to the adapter 1404 described with respect to FIGS. 7*a*-7*g*, in example embodiments, the ring 1422 of the adapter 1404 may include a groove 1428 extending at least partly (and, in some examples, completely) around (e.g., concentrically) the longitudinal axis X, and being shaped, sized, located, and/or otherwise configured to accept the member 1434 and/or other structural feature of the adapter 1402. As shown in at least FIG. 14*c*, such a member 1434 may extend distally (e.g., in a direction toward the cuff 12 when the fitting 1402 is removably attached to the adapter 1404) from an outer surface 1436 of the fitting 1402 disposed opposite and/or facing the top surface 1426 when the fitting 1402 is removably attached to the adapter 1404. As described above with respect to FIG. 14*a*, in some examples, the member 1434 may comprise a shaft, pin, rod, tab, rib, ring, ridge, flange, and/or other extension of the body 1406 protruding from the outer surface 1436, and the engagement between the member 1434 and the groove 1428 may assist in laterally and/or otherwise aligning the fitting 1402 with the adapter 1404 when removably attaching the fitting 1402 to the adapter 1404. While FIG. 14*c* illustrates the groove 1428 and the member 1434 being spaced radially from, for example, a radially innermost end 1430 of the top surface 1426, in other examples the member 1434, groove 1428, ring 1422, and/or other components of the fitting 1402 and/or of the adapter 1404 may be disposed and/or configured substantially as described above with respect to FIG. 7*f*, 10*a*, 14*a*, and/or one or more other embodiments of the present disclosure. For example, in some embodiments the groove 1428 and the member 1434 shown in FIG. 14*c* may be configured substantially the same as the corresponding groove 728 and member 734 described above with respect to FIG. 7*f*.

Moreover, as shown in FIG. 14*c*, in addition to the groove 1428, the ring 1422 of the adapter 1404 may also include one or more surfaces, sections, and/or other modified portions 1474 configured to accept and/or otherwise engage with a corresponding additional member 1472 of the fitting 1402. In some examples, such a modified portion 1474 of the ring 1422 may comprise an additional groove, channel, notch, indentation, hole, or other portion of the ring 1422 that, relative to the ring 722 and/or the substantially convex top surface 726 shown in FIG. 7*a*, has been omitted (e.g., via a molding process) or removed (e.g., via a mechanical or other removal process) from the ring 1422. In such examples, the additional groove, channel, notch, indentation, hole, or other modified portion 1474 of the ring 1422 may be substantially annular, may extend (at least partially) circumferentially around the longitudinal axis X, and/or may otherwise be configured similar to the groove 1428 to facilitate rotation of the fitting 1402 relative to the adapter 1404. Further, in the embodiment of FIG. 14*c* the modified portion 1474 of the ring 1422 may be formed and/or disposed between the groove 1428 and the radially innermost end 1430 of the top surface 1426. Additionally or alternatively, the modified portion 1474 of the ring 1422 may be formed by and/or disposed on a portion of the ring 1422 radially outward of the groove 1428. For example, at least part of the modified portion 1474 may be formed and/or disposed between the groove 1428 and a radially outermost end of the top surface 1426.

As shown in FIG. 14*c*, in some examples the modified portion 1474 of the ring 1422 may comprise a substantially planar portion of the top surface 1426. Alternatively, in other embodiments the modified portion 1474 of the ring 1422 may comprise a substantially curved, substantially concave, and/or substantially convex surface or portion of the ring 1422. Further, as shown in FIG. 14*c*, in some examples at least a portion 1490 of the top surface 1426 may extend radially inwardly from the modified portion 1474, and such a portion 1490 of the top surface 1426 may extend substantially perpendicular to the longitudinal axis X. For example, such a portion 1490 of the top surface 1426 may extend radially inward from a first end 1484 (e.g., a radially innermost end) of the modified portion 1474 to a radially outermost sidewall of the groove 1428 and/or to the radially innermost end 1430 of the top surface 1426. Alternatively, as shown in the embodiment of FIG. 14*e*, in other examples the top surface 1426 may be substantially planar and may extend substantially linearly from a radially innermost end 1430 of the top surface 1426 to a radially outermost end 1432 of the top surface 1426. In the example of FIG. 14*e*, the groove 1428 may be spaced radially from the radially innermost end 1430 by any desired distance. In still further embodiments, the groove 1428 and the member 1434 illustrated in at least FIG. 14*e* may be omitted.

In any of the examples described herein, the groove 1428 may include a radially innermost sidewall radially spaced from the radially innermost end 1430 of the top surface 1426 by at least a portion 1488 of the top surface 1426. In such examples, the substantially planar surface, curved surface, and/or other surface of the modified portion 1474 may include a first end 1484 (e.g., a radially innermost end) disposed at a location on the top surface 1426 radially spaced from the groove 1428 (e.g., radially spaced from a radially outermost sidewall of the groove 1428 disposed opposite the radially innermost sidewall of the groove 1428). Additionally, in such examples the substantially planar surface, curved surface, and/or other surface of the modified portion 1474 may include a second end 1486 (e.g., a radially outermost end) disposed proximate a radially outermost end of the top surface 1426.

Additionally, in any of the examples described herein the shape, size, location, orientation, and/or other configuration of the modified portion 1474 may match a configuration of the additional member 1472 of the fitting 1402. For instance, as shown in FIGS. 14*c* and 14*e*, the additional member 1472 of the fitting 1402 may comprise a substantially planar portion of the outer surface 1436. Alternatively, in other embodiments the additional member 1472 may comprise a substantially curved, substantially concave, and/or substantially convex surface or portion of the outer surface 1436 opposite and facing the modified portion 1474. In such examples, the additional member 1472 may mate with and/or otherwise at least partially engage the modified portion 1474 when the fitting 1402 is removably attached to the adapter 1404. Such engagement between the additional member 1472 and the modified portion 1474 may assist in minimizing and/or substantially eliminating lateral movement of the fitting 1402 relative to the adapter 1404 when the fitting 1402 is removably attached to the adapter 1404. Such engagement may also provide additional rigidity, support, and/or stability to the removable connection between the fitting 1402 and the adapter 1404, while still facilitating rotation of the fitting 1402 relative to the adapter 1404. Such engagement may also cause the longitudinal axis Z of the fitting 1402 (FIG. 2) to be collinear with the longitudinal axis X of the adapter 1404.

Further, as shown in FIGS. 14*c* and 14*e*, the additional member 1472 and the modified portion 1474 may be disposed at complimentary angles relative to, for example, the longitudinal axis X when the fitting 1402 is removably attached to the adapter 1404. For instance, the portion of the top surface 1426 forming the modified portion 1474 may be disposed at an acute included angle α relative to an axis 1478 that extends parallel to the longitudinal axis X. In such examples, the portion of the outer surface 1436 forming the additional member 1472 may be disposed at a complimentary acute included angle A relative to an axis 1476 that extends perpendicular to the axis 1478 and the longitudinal axis X.

Further, it is understood that in some embodiments the additional member 1472 may include and/or comprise one or more pins, flanges, detents, and/or other extensions, and in such embodiments the portion of the top surface 1426 forming the modified portion 1474 may include one or more grooves, channels, dimples, indents, and/or other structures configured to accept such extensions. In still further embodiments, it is understood that the groove 1428 may be formed by the fitting 1402 and the member 1434 may be formed by the adapter 1404.

Figure 14D:
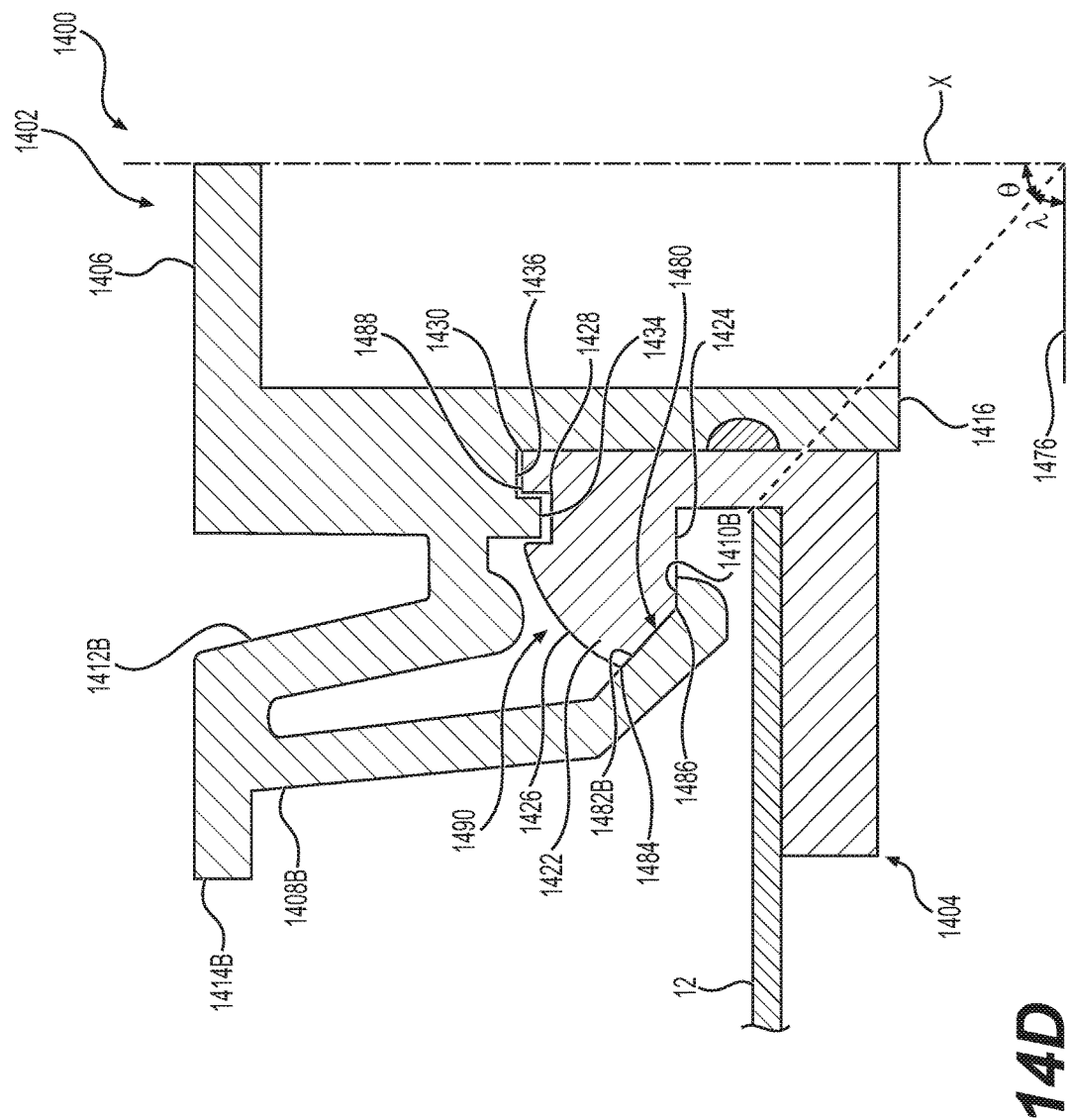
FIG. 14d is a partial cross-sectional view of another example blood pressure cuff adapter and an example fitting removably attached to the adapter.
Figure 14E:
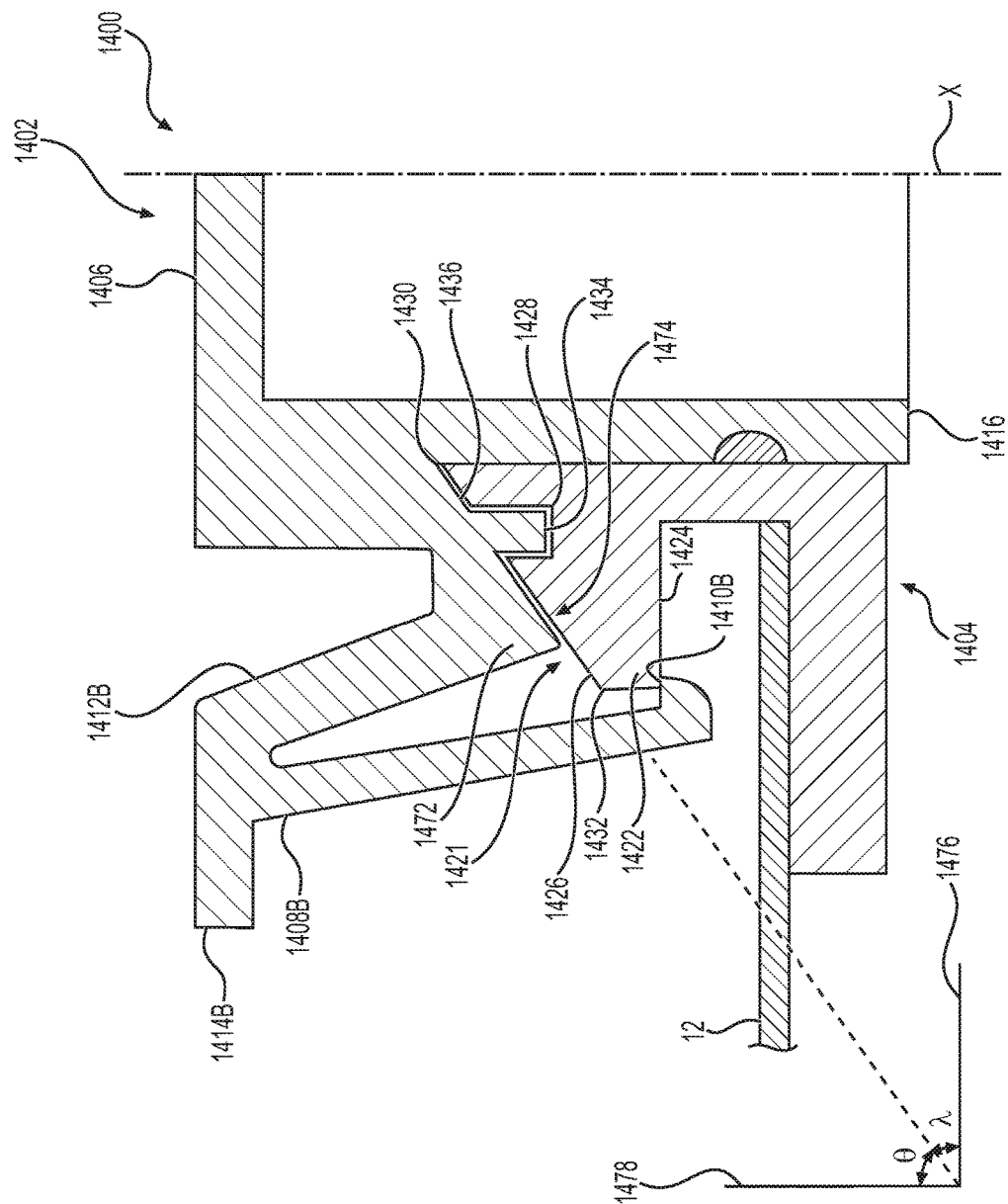
FIG. 14e is a partial cross-sectional view of yet another example blood pressure cuff adapter and an example fitting removably attached to the adapter.

With reference to at least FIG. 14*d*, and substantially similar to the embodiment described above with respect to FIG. 14*c*, in some examples the system 1400 may include an adapter 1404 having an annular groove 1428, and a fitting 1402 having one or more protruding members 1434 configured to at least partly engage (e.g., at least partly extend into, at least partly contact, at least partly slidably engage, etc.) the groove 1428 when the fitting 1402 is releasably attached to the adapter 1404. For example, similar to the adapter 1404 described with respect to FIG. 14*c*, in example embodiments, the ring 1422 of the adapter 1404 shown in FIG. 14*d* may include a groove 1428 extending at least partly (and, in some examples, completely) around (e.g., concentrically) the longitudinal axis X, and being shaped, sized, located, and/or otherwise configured to accept the member 1434 and/or other structural feature of the adapter 1402. In such embodiments, the member 1434 and/or other components of the fitting 1402 shown in FIG. 14*d* may be substantially similar to and/or the same as the corresponding components of the fitting 1402 described above with respect to FIG. 14*c*, and the groove 1428 and/or other components of the adapter 1404 may be substantially similar to and/or the same as the corresponding components of the adapter 1404 described above with respect to FIG. 14*c*.

In some embodiments, as shown in FIG. 14*d*, in addition to the groove 1428, the ring 1422 of the adapter 1404 may also include one or more surfaces, sections, and/or other modified portions 1480 configured to accept and/or otherwise engage with a corresponding additional member of the fitting 1402. In the example shown in the partial cross-section of FIG. 14*d*, the fitting 1402 may include a first arm 1408*a* (not shown) and a second arm 1408*b* opposite the first arm 1408*a*. In such examples, a shelf 1410*a* (not shown) and/or other radially inwardly facing surface or portion of the first arm 1408*a* may form a first additional member 1482*a* (not shown) of the fitting 1402, and a shelf 1410*b* and/or other radially inwardly facing surface or portion of the second arm 1408*b* may form a second additional member 1482*b* of the fitting 1402. As shown in FIG. 14*d*, in such examples the modified portion 1480 of the ring 1422 may be formed by and/or may comprise a surface and/or other portion of the ring 1422 disposed opposite the top surface 1426 and/or disposed on a radially outwardly facing portion of the ring 1422. In particular, in such examples, the modified portion 1480 may at least partly face the top surface of the cuff 12.

In some examples, the modified portion 1480 of the ring 1422 shown in FIG. 14*d* may comprise an additional groove, channel, notch, indentation, hole, or other portion of the ring 1422 that, relative to the ring 722 and/or the substantially planar bottom surface or ridge 724 shown in FIG. 7*a*, has been omitted (e.g., via a molding process) or removed (e.g., via a mechanical or other removal process) from the ring 1422. In such examples, the additional groove, channel, notch, indentation, hole, or other modified portion 1480 of the ring 1422 shown in FIG. 14*d* may be substantially annular, may extend (at least partially) circumferentially around the longitudinal axis X, and/or may otherwise be configured similar to the groove 1428 to facilitate rotation of the fitting 1402 relative to the adapter 1404.

As shown in FIG. 14*d*, in some examples the modified portion 1480 of the ring 1422 may comprise a substantially planar surface and/or other portion of the ring 1422 extending distally and radially inwardly between and/or from the top surface 1426 to the ridge 1424. Alternatively, in other embodiments the modified portion 1480 of the ring 1422 may comprise a substantially curved, substantially concave, and/or substantially convex surface or portion of the ring 1422.

In any of the examples described herein, the groove 1428 may include a radially innermost sidewall that is radially spaced from a radially innermost end (e.g., the radially innermost end 1430 described above with respect to FIG. 14c) of the top surface 1426 by a portion 1488 of the top surface 1426. In such examples, the substantially planar surface, curved surface, and/or other surface of the modified portion 1480 may include a first end 1484 (e.g., a radially outermost end) disposed proximate, adjacent, and/or at a radially outermost end of the top surface 1426. Further, in such examples the substantially planar surface, curved surface, and/or other surface of the modified portion 1480 may include a second end 1486 (e.g., a radially innermost end) disposed proximate, adjacent, and/or at a radially outermost end of the ridge 1424. In such examples, the first end 1484 of the modified portion 1480 may be radially spaced from a radially outermost sidewall of the groove 1428 by an additional portion 1490 of the top surface 1426.

Additionally, in any of the examples described herein the shape, size, location, orientation, and/or other configuration of the modified portion 1480 may match a configuration of the first and second additional members 1482a, 1482b of the fitting 1402. For instance, the first and second additional members 1482a, 1482b may comprise substantially planar surfaces of the respective arms 1408a, 1408b. Alternatively, in other embodiments the first and second additional members 1482a, 1482b may comprise substantially curved, substantially concave, and/or substantially convex surfaces or portions of the respective arms 1408a, 1408b. In such examples, the first and second additional members 1482a, 1482b may mate with and/or otherwise at least partially engage the first and second additional members 1482a, 1482b when the fitting 1402 is removably attached to the adapter 1404. Such engagement may assist in minimizing and/or substantially eliminating lateral movement of the fitting 1402 relative to the adapter 1404 when the fitting 1402 is removably attached to the adapter 1404. Such engagement may also provide additional rigidity, support, and/or stability to the removable connection between the fitting 1402 and the adapter 1404, while still facilitating rotation of the fitting 1402 relative to the adapter 1404. Such engagement may also cause the longitudinal axis Z of the fitting 1402 (FIG. 2) to be collinear with the longitudinal axis X of the adapter 1404.

Further, the first and second additional members 1482a, 1482b and the modified portion 1474 may be disposed at complimentary angles relative to, for example, the longitudinal axis X when the fitting 1402 is removably attached to the adapter 1404. For instance, the portion of the ring 1422 forming the modified portion 1480 may be disposed at an acute included angle α relative to the longitudinal axis X. In such examples, the portions of the respective arms 1408a, 1408b forming the first and second additional members 1482a, 1482b may be disposed at respective complimentary acute included angles A relative to the longitudinal axis X and an axis 1476 extending perpendicular to the longitudinal axis X.

Further, it is understood that in some embodiments at least one of the first and second additional members 1482a, 1482b may include and/or comprise one or more pins, flanges, detents, and/or other extensions, and in such embodiments the portion of the ring 1422 forming the modified portion 1480 may include one or more grooves, channels, dimples, indents, and/or other structures configured to accept such extensions.

Figure 14F:
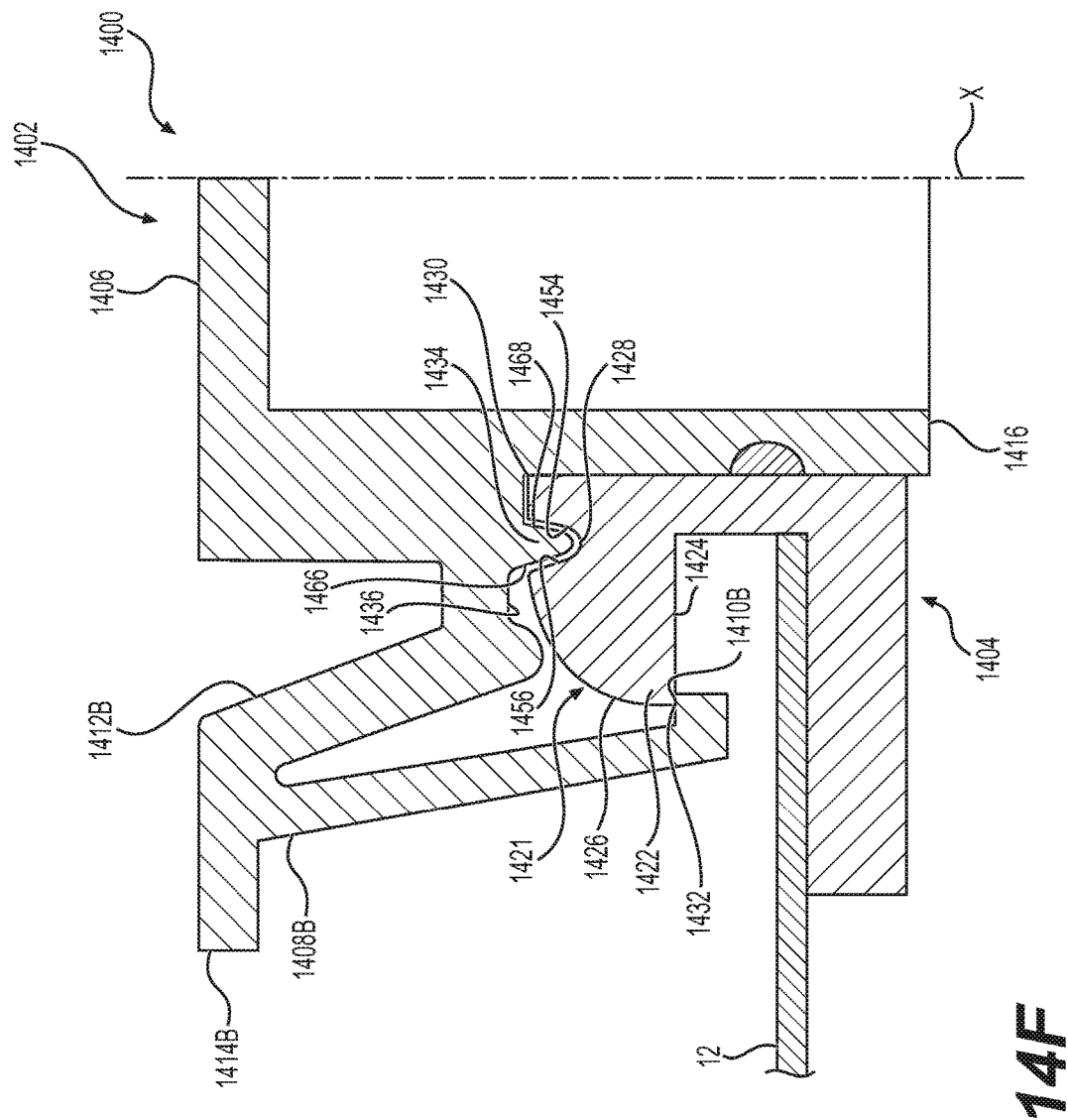
FIG. 14f is a partial cross-sectional view of a further example blood pressure cuff adapter and an example fitting removably attached to the adapter.

Moreover, with reference to at least FIG. 14f, in some examples the system 1400 may include an adapter 1404 having an annular groove 1428, and a fitting 1402 having one or more protruding members 1434 configured to at least partly engage (e.g., at least partly extend into, at least partly contact, at least partly slidably engage, etc.) the groove 1428 when the fitting 1402 is releasably attached to the adapter 1404. For example, similar to the adapter 1404 described with respect to FIGS. 7a-7g, in example embodiments, the ring 1422 of the adapter 1404 may include a groove 1428 extending at least partly (and, in some examples, completely) around (e.g., concentrically) the longitudinal axis X, and being shaped, sized, located, and/or otherwise configured to accept the member 1434 and/or other structural feature of the adapter 1402. As shown in at least FIG. 14f, such a member 1434 may extend distally (e.g., in a direction toward the cuff 12 when the fitting 1402 is removably attached to the adapter 1404) from an outer surface 1436 of the fitting 1402 disposed opposite and/or facing the top surface 1426 when the fitting 1402 is removably attached to the adapter 1404. As described above with respect to FIG. 14a, in some examples, the member 1434 may comprise a shaft, pin, rod, tab, rib, ring, ridge, flange, and/or other extension of the body 1406 protruding from the outer surface 1436, and the engagement between the member 1434 and the groove 1428 may assist in laterally and/or otherwise aligning the fitting 1402 with the adapter 1404 when removably attaching the fitting 1402 to the adapter 1404. Example members 1434 of the present disclosure may have any shape, size, cross-sectional profile and/or other configuration to facilitate such functionality.

For example, FIG. 14f illustrates an embodiment in which the member 1434 comprises a substantially V-shaped cross-section. In such examples, the member 1434 may include a radially outermost sidewall 1466 and a radially innermost sidewall 1468, and the radially outermost sidewall 1466 may extend at an acute included angle relative to the radially innermost sidewall 1468. Moreover, the configuration of the groove 1428 shown in FIG. 14f may substantially match and/or otherwise correspond to the shape, size, cross-sectional profile, location, and/or other configuration of the member 1434. For example, the groove 1428 may include a radially innermost sidewall 1454, and a radially outermost sidewall 1456, and the radially innermost sidewall 1454 may extend at an acute included angle relative to the radially outermost sidewall 1456. In such examples, the radially innermost sidewall 1454 of the groove 1428 may extend substantially parallel to the radially innermost sidewall 1468 of the member 1434 when the fitting 1402 is removably attached to the adapter 1404. Similarly, the radially outermost sidewall 1456 of the groove 1428 may extend substantially parallel to the radially outermost sidewall 1466 of the member 1434 when the fitting 1402 is removably attached to the adapter 1404. Accordingly, in such embodiments at least part of the member 1434 may contact and/or slidably engage the groove 1428 when the fitting 1402 is removably attached to the adapter 1404. Further, in the embodiment of FIG. 14f, at least one of the sidewalls 1454, 1456 of the groove 1428 and/or at least one of the sidewalls 1466, 1468 of the member 1434 may be substantially planar, substantially curved, substantially convex, substantially concave, substantially tapered, and/or any other configuration.

The following clauses describe, alone and/or in combination, example embodiments of the present disclosure:

A: A blood pressure cuff adapter includes a substantially rigid body having a distal portion, a proximal portion, a substantially cylindrical inner wall forming a central opening of the body, the inner wall extending from the distal portion to the proximal portion, and a longitudinal axis extending substantially centrally through the opening, the distal portion including: an annular ring having a top surface and a groove, the groove extending at least partly around the longitudinal axis and being configured to accept a corresponding member of a fitting when the fitting is removably attached to the adapter, and a ridge disposed opposite the top surface, the ridge extending substantially perpendicular to the longitudinal axis; and a seal disposed adjacent to the inner wall, the seal configured to form a substantially fluid-tight seal with the fitting when the fitting is removably attached to the adapter.

B: The blood pressure cuff adapter of clause A, wherein the top surface comprises a convex surface extending radially away from the longitudinal axis from a distal end of the top surface to a proximal end of the top surface, the groove being disposed between the distal end and the proximal end.

C: The blood pressure cuff adapter of any of the above clauses, wherein the member comprises one of a pin, a ring, and an arcuate ring segment extending substantially perpendicularly from an outer surface of the fitting.

D: The blood pressure cuff adapter of any of the above clauses, wherein the groove comprises at least one detent configured to contact the member as the fitting is rotated about the longitudinal axis of the adapter.

E: The blood pressure cuff adapter of any of the above clauses, wherein the groove comprises a base, a first sidewall, and a second sidewall opposite the first sidewall, the at least one detent being disposed on the base.

F: The blood pressure cuff adapter of any of the above clauses, wherein the groove comprises a base having a trough and a peak, the peak being disposed axially closer to the top surface of the ring than the trough.

G: The blood pressure cuff adapter of any of the above clauses, wherein the groove includes a wall prohibiting 360 degree rotation of the fitting about the longitudinal axis when the fitting is removably attached to the adapter.

H: The blood pressure cuff adapter of any of the above clauses, further comprising at least one of an RFID tag, a bar code, or a conductor disposed on a base of the grove.

The blood pressure cuff adapter of any of the above clauses, wherein the groove comprises a base extending radially from the inner wall, and a sidewall extending from the base to the top surface of the ring, the top surface comprising a curved surface extending from the sidewall of the groove.

J: The blood pressure cuff adapter of any of the above clauses, wherein the top surface of the ring extends from the inner wall, and wherein the groove comprises a sidewall extending from the top surface to a base of the groove, the base extending radially from the sidewall to a radially outermost portion of the ring.

K: The blood pressure cuff adapter of any of the above clauses, wherein the member includes a first sidewall disposed at an acute included angle relative to the longitudinal axis, and the groove includes a second sidewall disposed at the acute included angle, wherein the first sidewall slidably engages the second sidewall when the fitting is removably attached to the adapter.

L: The blood pressure cuff adapter of any of the above clauses, wherein the top surface forms a modified portion of the ring disposed radially outward of the groove, the modified portion comprising a substantially planar surface extending at an acute included angle relative to the longitudinal axis, wherein an additional member of the fitting is configured to slidably engage the modified portion of the ring when the fitting is removably attached to the adapter.

M: The blood pressure cuff adapter of any of the above clauses, wherein the modified portion of the ring includes an additional groove, and wherein the additional member of the fitting includes an additional member configured to engage the additional groove when the fitting is removably attached to the adapter.

N: The blood pressure cuff adapter of any of the above clauses, wherein the ring includes a modified portion disposed between the top surface and the ridge, the modified portion comprising a substantially planar surface extending at an acute included angle relative to an axis that is perpendicular to the longitudinal axis, wherein an additional member of the fitting is configured to slidably engage the modified portion of the ring when the fitting is removably attached to the adapter.

O: The blood pressure cuff adapter of any of the above clauses, wherein: the top surface comprises a substantially planar surface extending from a radially innermost end disposed proximate the inner wall to a radially outermost end, the groove is disposed between the radially innermost end and the radially outermost end, and the top surface extends at an acute included angle relative to the longitudinal axis.

P: A blood pressure cuff adapter includes a substantially rigid body having a distal portion, a proximal portion, a substantially cylindrical inner wall forming a central opening of the body, the inner wall extending from the distal portion to the proximal portion, and a longitudinal axis extending substantially centrally through the opening, the distal portion including: an annular ring having a top surface and a groove, the groove extending at least partly around the longitudinal axis and being configured to accept a corresponding member of a fitting when the fitting is removably attached to the adapter, and the top surface forming a modified portion of the ring disposed radially outward of the groove, the modified portion comprising a substantially planar surface extending at an acute included angle relative to the longitudinal axis, and a ridge disposed opposite the top surface, the ridge extending substantially perpendicular to the longitudinal axis; and a seal disposed adjacent to the inner wall, the seal configured to form a substantially fluid-tight seal with the fitting when the fitting is removably attached to the adapter.

Q: The blood pressure cuff adapter of any of the above clauses, the distal portion of the body further including: a substantially cylindrical sidewall extending from the ridge to a top surface of the proximal portion; and a feature disposed proximate the groove, the feature comprising at least one of a layer of reflective paint, a layer of reflective ink, an RFID tag, or a barcode.

R: The blood pressure cuff adapter of any of the above clauses, wherein: the groove includes a radially innermost sidewall radially spaced from a radially innermost end of the top surface; the substantially planar surface of the modified portion includes a first end disposed at a location on the top surface radially spaced from the groove; and the substantially planar surface includes a second end disposed proximate a radially outermost end of the top surface.

S: A blood pressure cuff adapter includes: a substantially rigid body having a distal portion, a proximal portion, a substantially cylindrical inner wall forming a central opening of the body, the inner wall extending from the distal portion to the proximal portion, and a longitudinal axis extending substantially centrally through the opening, the distal portion including: an annular ring having a top surface, a groove extending at least partly around the longitudinal axis and being configured to accept a corresponding member of a fitting when the fitting is removably attached to the adapter, a ridge disposed opposite the top surface, the ridge extending substantially perpendicular to the longitudinal axis, and a modified portion disposed between the top surface and the ridge, the modified portion comprising a substantially planar surface extending at an acute included angle relative to an axis that is perpendicular to the longitudinal axis; and a seal disposed adjacent to the inner wall, the seal configured to form a substantially fluid-tight seal with the fitting when the fitting is removably attached to the adapter.

T: The blood pressure cuff adapter of any of the above clauses, wherein: the groove includes a radially innermost sidewall radially spaced from a radially innermost end of the top surface; the substantially planar surface of the modified portion includes a first end disposed proximate a radially outermost end of the top surface; and the substantially planar surface includes a second end disposed proximate a radially outermost end of the ridge.

The example systems and methods of the present disclosure overcome various deficiencies of known prior art devices. Other embodiments of the present disclosure will be apparent to those skilled in the art from consideration of the specification and practice of the disclosure contained herein. It is intended that the specification and examples be considered as example only, with a true scope and spirit of the present disclosure being indicated by the following claims.

What is claimed is:

1. A blood pressure cuff adapter, comprising:
   a substantially rigid body having a distal portion, a proximal portion, a substantially cylindrical inner wall forming a central opening of the body, the inner wall extending from the distal portion to the proximal portion, and a longitudinal axis extending substantially centrally through the opening, the distal portion including:
      an annular ring having a top surface and a groove, the groove extending at least partly around the longitudinal axis and being configured to accept a corresponding member of a fitting when the fitting is removably attached to the adapter, and
      a ridge disposed opposite the top surface, the ridge extending substantially perpendicular to the longitudinal axis, wherein the groove comprises a base, a first sidewall, a second sidewall opposite the first sidewall, and at least one detent disposed on the base, the at least one detent being configured to contact the member as the fitting is rotated about the longitudinal axis of the adapter; and
   a seal disposed adjacent to the inner wall, the seal configured to form a substantially fluid-tight seal with the fitting when the fitting is removably attached to the adapter.

2. The blood pressure cuff adapter of claim 1, wherein the top surface comprises a convex surface extending radially away from the longitudinal axis from a distal end of the top surface to a proximal end of the top surface, the groove being disposed between the distal end and the proximal end.

3. The blood pressure cuff adapter of claim 1, wherein the member comprises one of a pin, a ring, and an arcuate ring segment extending substantially perpendicularly from an outer surface of the fitting.

4. The blood pressure cuff adapter of claim 1, wherein the base includes a trough and a peak, the peak being disposed axially closer to the top surface of the ring than the trough.

5. The blood pressure cuff adapter of claim 1, wherein the groove includes a wall prohibiting 360 degree rotation of the fitting about the longitudinal axis when the fitting is removably attached to the adapter.

6. The blood pressure cuff adapter of claim 1, further comprising at least one of an RFID tag, a bar code, or a conductor disposed on a base of the groove.

7. The blood pressure cuff adapter of claim 1, wherein a part of the distal portion is made from a first material, and a part of the proximal portion is made from a second material different from the first material.

8. The blood pressure cuff adapter of claim 1, further including a substantially cylindrical sidewall extending from the ridge to a top surface of the proximal portion.

9. The blood pressure cuff adapter of claim 1, wherein the top surface of the ring is one of substantially concave, substantially curved, and substantially tapered.

10. The blood pressure cuff adapter of claim 1, wherein disposing at least part of the member within the groove when the fitting is removably attached to the adapter causes a longitudinal axis of the fitting to be collinear with the longitudinal axis of the adapter.

11. The blood pressure cuff adapter of claim 1, wherein the at least one detent is one of substantially dome-shaped and substantially ramp-shaped.

12. The blood pressure cuff adapter of claim 1, wherein the groove is disposed on the top surface.

13. The blood pressure cuff of claim 12, wherein the top surface includes a distal end and a proximal end, and wherein the groove is disposed between the distal end and the proximal end.

14. A blood pressure cuff adapter, comprising:
   a substantially rigid body having a distal portion, a proximal portion, a substantially cylindrical inner wall forming a central opening of the body, the inner wall extending from the distal portion to the proximal portion, and a longitudinal axis extending substantially centrally through the opening, the distal portion including:
      an annular ring having a top surface and a groove, the groove extending at least partly around the longitudinal axis and being configured to accept a corresponding member of a fitting when the fitting is removably attached to the adapter, and
      a ridge disposed opposite the top surface, the ridge extending substantially perpendicular to the longitudinal axis, wherein the groove includes a wall prohibiting 360 degree rotation of the fitting about the longitudinal axis when the fitting is removably attached to the adapter; and
   a seal disposed adjacent to the inner wall, the seal configured to form a substantially fluid-tight seal with the fitting when the fitting is removably attached to the adapter.

15. The blood pressure cuff adapter of claim 14, wherein the groove comprises at least one detent configured to contact the member when the fitting is removably attached to the adapter.

16. The blood pressure cuff adapter of claim 15, wherein the at least one detent is one of substantially dome-shaped and substantially ramp-shaped.

17. The blood pressure cuff adapter of claim 14, wherein the top surface comprises a convex surface extending radially away from the longitudinal axis from a distal end of the top surface to a proximal end of the top surface, the groove being disposed between the distal end and the proximal end.

18. The blood pressure cuff adapter of claim 14, wherein the top surface of the ring is one of substantially concave, substantially curved, and substantially tapered.

19. The blood pressure cuff adapter of claim 14, wherein the groove is disposed on the top surface.

20. A blood pressure cuff adapter, comprising:
a substantially rigid body having a distal portion, a proximal portion, a substantially cylindrical inner wall forming a central opening of the body, the inner wall extending from the distal portion to the proximal portion, and a longitudinal axis extending substantially centrally through the opening, the distal portion including:
an annular ring having a top surface and a groove, the groove extending at least partly around the longitudinal axis and being configured to accept a corresponding member of a fitting when the fitting is removably attached to the adapter, at least one of an RFID tag, a bar code, or a conductor disposed on a base of the groove, and
a ridge disposed opposite the top surface, the ridge extending substantially perpendicular to the longitudinal axis; and
a seal disposed adjacent to the inner wall, the seal configured to form a substantially fluid-tight seal with the fitting when the fitting is removably attached to the adapter.

21. The blood pressure cuff adapter of claim 20, wherein a height of the groove is variable along at least a portion of the groove.

22. The blood pressure cuff adapter of claim 21, wherein the base extends radially from the inner wall, the groove further comprising a sidewall extending from the base to the top surface of the ring, the top surface comprising a curved surface extending from the sidewall of the groove.

23. The blood pressure cuff adapter of claim 20, wherein the groove includes a sidewall extending substantially perpendicularly from the base.

24. The blood pressure cuff adapter of claim 23, wherein the sidewall extends from the base to the top surface.

25. The blood pressure cuff adapter of claim 20, wherein a sensor is connected to the member, and wherein the at least one of the RFID tag, the bar code, or the conductor is located at least partly within a field of view of the sensor when the fitting is removably attached to the adapter.

26. A blood pressure cuff adapter, comprising:
a substantially rigid body having a distal portion, a proximal portion, a substantially cylindrical inner wall forming a central opening of the body, the inner wall extending from the distal portion to the proximal portion, and a longitudinal axis extending substantially centrally through the opening, the distal portion including:
an annular ring having a top surface and a groove, the groove extending at least partly around the longitudinal axis and being configured to accept a corresponding member of a fitting when the fitting is removably attached to the adapter, wherein the top surface of the ring extends from the inner wall, and wherein the groove comprises a sidewall extending from the top surface to a base of the groove, the base extending radially from the sidewall to a radially outermost portion of the ring, and
a ridge disposed opposite the top surface, the ridge extending substantially perpendicular to the longitudinal axis; and
a seal disposed adjacent to the inner wall, the seal configured to form a substantially fluid-tight seal with the fitting when the fitting is removably attached to the adapter.

27. The blood pressure cuff adapter of claim 26, wherein at least part of the ring is configured to mate with at least a portion of the member, when the fitting is removably attached to the adapter, to assist in stabilizing a removable connection between the fitting and the adapter.

28. The blood pressure cuff adapter of claim 26, wherein engagement between the sidewall and a radially outermost surface of the member assists in substantially eliminating lateral movement of the fitting relative to the adapter when the fitting is removably attached to the adapter.

29. The blood pressure cuff adapter of claim 26, wherein the sidewall extends substantially perpendicularly from the base.

30. The blood pressure cuff adapter of claim 26, wherein the base extends substantially perpendicularly relative to the inner wall.

* * * * *